United States Patent [19]

Furlenmeier et al.

[11] Patent Number: 4,948,898
[45] Date of Patent: Aug. 14, 1990

[54] PROCESS FOR THE MANUFACTURE OF 1-SULPHO-2-OXOAZETIDINE DERIVATIVES

[75] Inventors: André Furlenmeier, Basel; Werner Hofheinz, Bottmingen, both of Switzerland; Christian N. Hubschwerlen, Durmenach, France; Hans P. Isenring, Sissach, Switzerland

[73] Assignee: Hoffmann-La Roche Inc., Nutley, N.J.

[21] Appl. No.: 317,081

[22] Filed: Feb. 28, 1989

Related U.S. Application Data

[60] Continuation of Ser. No. 926,742, Nov. 3, 1986, abandoned, which is a continuation of Ser. No. 852,046, Apr. 14, 1986, Pat. No. 4,652,651, which is a division of Ser. No. 499,595, May 31, 1983, abandoned.

[51] Int. Cl.$^5$ .............. C07D 213/73; C07D 231/12; C07D 233/46; C07D 263/48
[52] U.S. Cl. .................. 546/311; 548/233; 548/337; 548/378; 548/194
[58] Field of Search ............ 548/195, 233, 337, 378; 546/311

[56] References Cited

U.S. PATENT DOCUMENTS

| 4,304,718 | 12/1981 | Kamiya | 540/363 |
| 4,385,181 | 5/1983 | Farge | 544/182 |
| 4,572,801 | 2/1986 | Matsuo | 540/355 |

Primary Examiner—Robert Gerstl
Attorney, Agent, or Firm—George M. Gould; Bernard S. Leon; Alan P. Kass

[57] ABSTRACT

The manufacture of 1-sulpho-2-oxazetidine derivatives of the formula

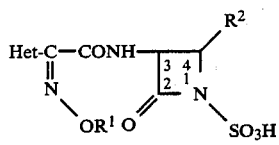

in which Het is an optionally amino-substituted, 5- or 6-membered, aromatic heterocycle containing 1 or 2 nitrogen atoms and optionally also an oxygen or sulphur atom, $R^1$ is hydrogen, lower alkyl, phenyl-lower alkyl, lower alkanoyl, lower alkoxycarbonyl, lower alkenyl-lower alkyl, lower alkoxycarbonyl-lower alkyl, phenyl-lower-alkoxycarbonyl-lower alkyl, nitrophenyl-lower-alkoxycarbonyl-lower alkyl or carboxy-lower alkyl and $R^2$ is hydrogen, lower alkyl, lower alkenyl, lower alkynyl, lower alkoxycarbonyl, lower alkanoyloxy-lower alkyl, lower alkoxycarbonyl-lower alkenyl, hydroxyiminomethyl, lower alkoxyiminomethyl, carbamoyl, carbamoyl-lower alkenyl or carbamoyloxy-lower alkyl, the group $=NOR^1$ being present at least partially in the syn-form, in racemic form or in the form of the 3S-enantiomer, and of readily hydrolyzable esters and pharmaceutically compatible salts of these compounds, by acylating a compound of the formula

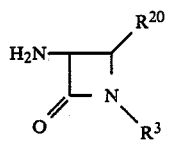

in which $R^{20}$ equals
$R^2$ or can also represent a 2,2-dimethyl-1,3-dioxolan-4-yl group and $R^3$ is hydrogen or sulpho,
or a salt thereof with a thioester of the formula

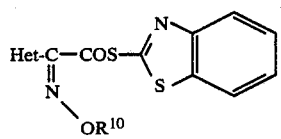

in which Het is as above and $R^{10}$ has any of the values of $R^1$ except carboxy-lower alkyl, and can also represent a tri-lower alkyl-silyl-lower-alkoxycarbonyl-lower alkyl group or a carboxy-lower alkyl group converted into a readily hydrolyzable ester group, and the group $=NOR^{10}$ is present at least partially in the syn-form, and carrying out subsequent steps (N-sulphonation, conversion of $R^{20}$ into $R^2$, $R^{10}$ into $R^1$), some of which are optional.

The invention also provides certain novel products of formula I and benzthiazolyl thioesters of formula III per se and the preparation of the benzthiazolyl thioesters by esterifying corresponding carboxylic acids. Finally, the invention provides a process for the preparation of carboxylic acids in which $R^1$ is t-alkoxycarbonylmethyl.

The compounds of formula I have antimicrobial activity.

5 Claims, No Drawings

PROCESS FOR THE MANUFACTURE OF 1-SULPHO-2-OXOAZETIDINE DERIVATIVES

This application is a continuation of application Ser. No. 06/926,742, filed 11-03-86 now abandoned, which is a continuation, of application Ser. No. 852,046 filed Apr. 14, 1986 U.S. Pat. No. 4,652,651 —Furlenmeier et al.—PROCESS FOR THE MANUFACTURE OF 1-SULPHO-2-OXOAZETIDINE DERIVATIVES, which is a divisional of Ser. No. 499,595 filed May 31, 1983, abandoned.

The present invention is concerned with a process for the manufacture of 1-sulpho-2-oxoazatidine derivatives of the formula

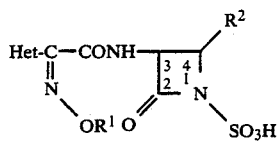    I in which Het is an optionally amino-substituted, 5-or 6-membered, aromatic heterocycle containing 1 or 2 nitrogen atoms and optionally also an oxygen or sulphur atom, $R^1$ is hydrogen, lower alkyl, phenyl-lower alkyl, lower alkanoyl, lower alkoxycaronyl, lower alkenyl-lower alkyl, lower alkoxycarbonyl-lower alkyl, phenyl-lower-alkoxycarbonyl-lower alkyl, nitrophenyl-loweralkoxycarbonyl-lower alkyl cr carboxy-lower alkyl and $R^2$ is hydrogen, lower alkyl, lower alkenyl, lower alkynyl, lower alkoxycarbonyl, lower alkanoyloxy-lower alkyl, lower alkoxycarbonyl-lower alkenyl, hydroxyiminomethyl, lower alkoxyiminomethyl, carbamoyl, carbamoyl-lower alkenyl or carbamoyloxy-lower alkyl, the group $=NOR^1$ being present at least partially in the syn-form,
in racemic form or in the form of the 3S-enantiomer, and of readily hydrolyzable esters and pharmaceutically compatible salts of these compounds.

The heterocycle denoted by "Het" includes all 5-or 6-membered aromatic ring structures which contain 1 or 2 nitrogen atoms and which are optionally substituted by an amino group; for example, pyrazolyl groups such as 2-pyrazol-3-yl, amino-pyridyl groups such as 2-amino-6-pyridyl and amino-midazolyl groups such as 2-amino-4-imidazolyl. They can optionally contain an oxygen atom such as, for example, in the case of amino-cxazolyl groups, for example 2-amino-4-oxazolyl, or a sulphur atom such as, for example, in the case of aminothiadiazolyl groups such as 5-amino-3-(1,2,4-thiadiazolyl) or, especially, in the case of aminothiazolyl groups such as 2-amino-4-thiazolyl.

The term "lower alkyl" alone or in combinations signifies an aliphatic hydrocarbon group which can be straight-chain or branched-chain and which preferably contains up to 7 carbon atoms such as, for example, methyl, ethyl, n-propyl, isopropyl, n-butyl, isobutyl, sec-butyl, t-butyl, n-pentyl, isopentyl, n-hexyl, n-heptyl etc. The term "lower alkoxy" has an analogous significance. The term "lower alkenyl" alone or in combinations signifies an olefinic hydrocarbon group which can be straight-chain or branched-chain and which prefera-
bly contains up to 7 carbon atoms such as, for example, vinyl, allyl, isopropenyl, 2-methallyl, 2-butenyl, 3-butenyl, 2-hexenyl, 2-heptenyl etc. The term "lower alkynyl"signifies an acetylenic hydrocarbon group which can be straight-chain or branched and which preferably contains up to 7 carbon atoms such as, for example, ethynyl, 1-propynyl, 2-propynyl, 2-hexynyl, 2-heptynyl etc. The term "lower alkanoyl" or "lower alkanoyloxy"signifies an aliphatic carboxylic acid residue which preferably contains up to 7 carbon atoms such as, for example, acetyl, propionyl, isobutyryl, acetoxy, propionyloxy and isobutyryloxy.

Preferred groups denoted by $R^1$ are hydrogen, methyl, ethy, isopropyl, benzyl, 2-phenethyl, acetyl, propionyl, methoxycarbonyl, ethoxycarbony, methoxycarbonylmethyl, t-butoxycarbonylmethyl, carboxymethyl, 1-methyl-1-t-butoxycarbonyl-ethyl, 1-methyl-1-benzhydryloxycarbonyl-ethyl, 1-methyl-1-trityloxycarbonyl-ethyl, 1-methyl-1-(p-nitrobenzyloxycarbonyl)-ethyl and 1-methyl-1-carboxyethyl; especially methyl, carboxymethyl and 1-methyl-1-carboxyethyl.

Preferred groups denoted by $R^2$ are methyl, ethyl, n-propyl, vinyl, allyl, ethynyl, 3-acetoxy-n-propyl, methoxycarbonyl, hydroxyiminomethyl, methoxyiminomethyl, 2-ethoxycarbonyl- 1-methylvinyl, carbamoyl, carbamoylvinyl and carbamoyloxymethyl; especially carbamoyl and carbamoxyloxymethyl.

Preferred groups of the formula

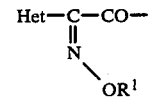

are 2-pyrazol-3-yl-2-methoxyiminoacetyl, 2-(2-amino-4-thiazolyl)-2-methoxyiminoacetyl, 2-(2-amino-4-thiazolyl)-2-(carboxymethoxyimino)-acetyl, 2-(2-amino-4-thiazolyl)-2-(1-methyl-1-methyl-1-carboxyethoxyimino)-acetyl, 2-(2-amino-4-oxazolyl)-2-methoxyiminoacetyl, 2-[5-amino-3-(1,3,4-thiadiazolyl)]-2-methoxyiminoacetyl, 2-(2-amino-4-imidazolyl)-2-methoxyiminoacetyl and 2-(2-amino-6-pyridyl)-2-methoxyiminoacetyl; especially 2-(2-amino-4-thiazolyl)-2-methoxyiminoacetyl, 2-(2-amino-4-thiazolyl)-2-(1-methyl-1-carboxyethoxyimino)-acetyl and 2-(2-amino-4-thiazolyl)-2-(carboxymethoxyimino)-acetyl.

The compounds of formula I can be present in various isomeric forms [e.g. cis, trans; syn (Z-form), anti (E-form); and as the 3S-enantioner]. This also applies to the starting materials referred to hereinafter.

The compounds of formula I can be present as free acids or as betains or also as pharmaceutically compatible salts which are obtained by salt formation with a basic salt former on the free 1-sulpho group or on a carboxy group which may be present in the substituent in the 3-position. Examples of basic salt formers are inorganic cations such as sodium and potassium ions, basic amino acids such as arginine, ornithine, lysine or histidine and polyhydroxyalkylamines such as N-methylglucamine, diethanolmine, triethanolamine etc.

Carboxy groups present in a compound of formula I or salts thereof can be converted by appropriate esterification into readily hydrolyzable ester groups. Such readily hydrolyzable ester groups, which are cleaved in the body into the corresponding free carboxy groups, are, for example, Γ-(lower alkoxy)-lower-alkoxycarbonyl groups such as methoxymethoxycarbonyl and α-methoxyethoxycarbonyl, lower alkylthiomethoxycarbonyl groups such as methylthiomethoxycarbonyl, Γ-(lower alkanoyl)-lower-alkoxycarbonyl groups such as acetoxymethoxycarbonyl, pivaloyloxymethoxycarbonyl and α-pivaloyloxyethoxycarbonyl, α-(lower alkoxycarbonyl)-lower-alkoxycarbonyl groups such as ethoxycarbonyloxymethoxycarbonyl, t-butoxycarbonylmethoxycarbonyl and α-ethoxycarbonyloxyethoxycarbonyl, lactonyl groups such as phthalidyl and thiophthalidyl, or the group of the formula

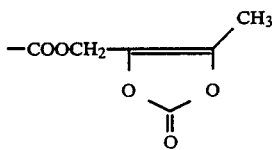

Examples of compounds of formula I which can be manufactured in accordance with the present invention are the end products described in Examples 1–50 hereinafter not only in the form in which they are present in the Examples (3S-enantiomer or racemates), but also in the form of readily hydrolyzable esters and pharmaceutically compatible salts of these compounds.

Especially preferred compounds of formula I are the compounds of the formula

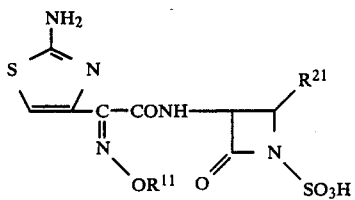

wherein $R^{11}$ is methyl, carboxymethyl or 1-methyl-1-carboxyethyl and $R^{21}$ is carbamoyl or cabamoyloxymethyl,
in racemic form or in the form of the 3S-enantiomer and the corresponding readily hydrolyzable esters and pharmaceutically compatible salts of these compounds.

Especially preferred among these compounds are (3S, 4S)-3-[(Z)-2-(2-amino-4-thiazolyl)-2-[(1-carboxy-1-methylethoxy]-imino]acetamido]-4-carbamoyloxymethyl-2-oxo-1-azetidinesulphonic acid and (3S, 4S)-3-[(Z)-2-(2-amino-4-thiazolyl)-2-[ (carboxymethoxy)imino]acetamido]-4-carbamoyloxymethyl-2-oxo-1-azetidinesulphonic acid and their pharmaceutically compatible salts.

The following are further sub-groups of compounds of formula I:
those in which Het, $R^1$ and $R^2$ are as above, with the proviso that when simultaneously Het is 2-amino-4-thiazolyl and $R^2$ is lower alkyl, lower alkanoyloxy-lower alkyl, carbamoyloxy-lower alkyl, lower alkoxycarbonyl, lower alkoxyiminomethyl or carbamoyl, then $R^1$ is hydrogen, lower alkyl, phenyl-lower alkyl, lower alkanoyl, lower alkoxycarbonyl or lower alkenyl-lower alkyl;
those in which Het, $R^1$ and $R^2$ are as above, with the proviso that when simultaneously Het is 2-amino-4-thiazolyl and $R^2$ is carbamoyloxy-lower alkyl, then $R^1$ is hydrogen, lower alkyl, phenyl-lower alkyl, lower alkanoyl, lower alkoxycarbonyl or lower alkenyl-lower alkyl;
in each case in racemic form or in the form of the 3S-enantiomer, and the corresponding readily hydrolyzable esters and pharmaceutically compatible salts of these compounds.

The compounds of formula I and their readily hydrolyzable esters and pharmaceutically compatible salts are manufactured in accordance with the invention by acylating a compound of the formula which is present in racemic form or in the form of the 3S-enatiomer ![Formula II structure]

II in which $R^{20}$ is equal to $R^2$ or can also represent a 2,2-dimethyl-1,3-dioxolan-4-yl group and $R^3$ is hydrogen or sulpho,
or a salt thereof with a thioester of the formula ![Formula III structure]

III in which Het is as above and $R^{10}$ is equal to $R^1$ except carboxyl-lower alkyl and can also represent a tri-lower alkyl-silyl-lower-alkoxycarbonyl-lower alkyl group or a carboxy-lower alkyl group converted into a readily hydrolyzable ester group, and the groups=NOR$^{10}$ is present at least partially in the syn-form,
to give a compound of the formula which is present in racemic form or in the form of the 3S-enantiomer ![Formula Ib structure]

Ib in which $R^{10}$, $R^{20}$, $R^3$ and Het are as above and the group =NOR$^{10}$ is present at least partially in the syn-form,
subsequently sulphonating a resulting product in which $R^3$ is hydrogen, converting a 2,2-diemthyl-1,3-dioxolan-4-yl group $R^{20}$ which may be present into the hydroxyiminomethyl group, a lower alkoxyiminomethyl group or the carbamoylvinyl group, converting a tri-lower alkyl-silyl-lower-alkoxycarbonyl-lower alkyl group $R^{10}$ into carboxy-lower alkyl, if desired converting a lower alkoxycarbonyl-lower alkyl, phenyl-lower-alkoxycarbonyl-lower alkyl or nitrophenyl-lower alkoxycarbonyl-lower alkyl group denoted by $R^{10}$ or $R^1$ into carboxy-lower alkyl and, if desired, converting a resulting product into a pharmaceutically compatible salt.

The reaction of a compound of formula II with a compound of formula III is conveniently carried out in an inert organic solvent, for example in a chlorinated hydrocarbon such as methylene chloride or chloroform, in an ether such as tetrahydrofuran or dioxan, in an ester such as ethyl acetate, in a ketone such as acetone, in an aprotic solvent such as acetonitrile, dimethylformamide or diemethylacetamide or in a mixture of one of these solvents with water. The reaction is conveniently carried out at a temperature between about −40° C. and +60° C., advantageously betweeen −15° C. and +25° C., especially between 0° C. and 20°C. The reaction is conveniently carried out using about stoichiometric amounts of the reactants or a slight excess of the thioester of formula III. The reaction is advantageously carried out in the presence of a base such as, for example, an organic amine such as triethylamine or N-methylmorpholine or an alkali metal bicarbonate such as sodium bicarbonate.

Products obtained in which $R^3$ is hydrogen are subsequently sulphonated. The sulphonation can be carried out in a manner known per se by reaction with sulphur trioxide or a reactive derivative thereof, for example with complexes of sulphur trioxide and an organic base such as pyridine, dimethylformamide, picoline etc. The reaction is carried out, for example, at about −10° C. to +80° C. in an inert organic solvent, for example in an ether such as dioxan, in an ester such as ethyl acetate, in a chlorinated hydrocarbon such as methylene chloride, in acetonitrile, in dimethylformamide or in pyridine.

Where $R^{20}$ in the reaction product of formula Ib is the 2,2-dimethyl-1,3-dioxolan-4-yl group, this is converted into the hydroxyiminomethyl group or into a lower alkoxyiminomethyl group in accordance with the following Scheme:

VI→VII: In aqueous alkali metal metaperiodate (e.g. sodium metaperiodate) at about room temperature.

VII→VIII: With hydroxylamine in an inert organic solvent such as methylene chloride, preferably in the presence of an organic base such a pyridine and at about room temperature.

VII→IX: With a O-lower-alkylhydroxylamine in analogy to VII→VIII.

VII→XIII: With carbamoylmethylenetriphenylphosphorane in an inert solvent (e.g. methylene chloride) and at about room temperature.

VII→IX: With a lower alkyl iodide in an inert organic solvent such as methylene chloride, preferably in the presence of an organic base such as pyridine or N-ethyldiisopropylamine and at about room temperature.

Where $R^{10}$ in the reaction product of formula IB is a tri-lower alkyl-silyl-lower -alkoxycarbonyl-lower alkyl group, for example the [[2(trimethylsilyl)ethoxy]-carbonyl]methyl group or the 1-methyl-1-[[2-(trimethylsilyl)-ethoxy]carbonyl]ethyl group, this is converted into the corresponding carboxy-lower alkyl group, conveniently by treatment with a quaternary organic fluoride such as tetrabutylammonium fluoride. The temperature preferably lies in the proximity of room temperature and the reaction is conveniently carried out in an inert organic solvent such as tetrahydrofuran or methanol.

Where $R^{10}$ or $R^1$ in the reaction product of formula Ib or I is a lower alkoxycarbonyl-lower alkyl group, for example the t-butoxycarbonylmethyl group or the 1-methyl-1-(t-butoxycarbonyl)-ethyl group, this can be converted, if desired, into the corresponding carboxy-lower alkyl group by treatment with a strong acid such as trifluoroacetic acid (optionally in the presence of anisole), hydrochloric acid or p-toluenesulphonic acid at a low temperature such as −10° C. to room temperature.

Where $R^{10}$ or $R^1$ in the reaction product of formula Ib or I is a phenyl-lower alkoxycarbonyl-lower alkyl

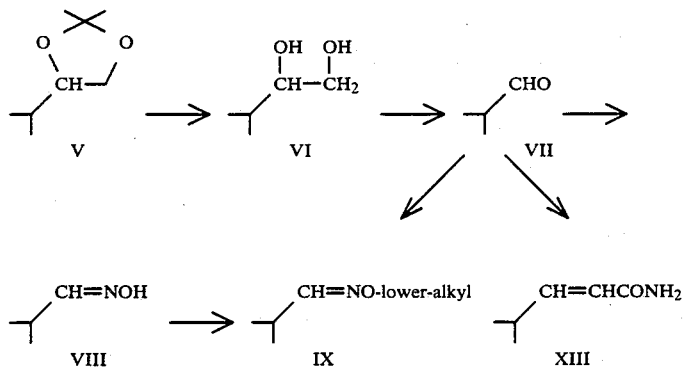

The reactions are preferably carried out as follows:

V→VI: In a lower alkanol such as methanol or in an aqueous ether such as aqueous dioxan or tetrahydrofuran in the presence of an acid catalyst such as a sulphonated ion exchanger, p-toluenesulphonic acid and the like, preferably at room temperature to about 60° C.

group, for example the benzyloxycarbonylmethyl group or the 1-methyl-1-(benzyloxycarbonyl)-ethyl group, or a nitrophenyl-lower-alkoxycarbonyl-lower alkyl group, for example the p-nitrobenzyloxycarbonylmethyl group or the 1-methyl-1-(p-nitrobenzyloxycarbonyl)-ethyl group, this can be converted, if desired, into the corresponding carboxy-lower alkyl group by catalytic hydrogenation with, for example, palladium/- carbon or palladium/diatomaceous earth as the catalyst, for example in a lower alkanol such as ethanol at about 0°–80° C.

The manufacture of the salts of the compounds of formula I can be carried out in a manner known per se; for example, by reacting an acid of formula I with an equivalent amount of the desired base, optionally in the form of an ion exchanger. The reaction is conveniently carried out in a solvent such as water or an organic solvent such as ethanol, methanol, acetone, ethyl acetate and the like. The temperature at which the salt formation is carried out is not critical, but it generally lies in the range of about 0°–50° C., preferably at room temperature.

The thioesters of formula III can be prepared by reacting a carboxylic acid of the formula

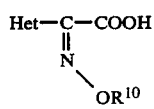    IV in which $R^{10}$ and Het are as above,
with dithio-bis-benzthiazole in the presence of a tri-(lower-alkyl)-phosphite and a base or in the presence of triphenylphosphine. The reaction is conveniently carried out at a temperature between −30° C. and +50° C. advantageously between about −20° C. and +25° C. The esterification is advantageously carried out in an organic solvent, for example in acetonitrile or in methylene chloride. The preferred embodiment comprises carrying out the reaction in the presence of tri-(lower alkyl)-phosphite and a base. Triethyl phosphite is preferably used as the tri-(lower alkyl)-phosphite and an organic base, especially a tertiary organic base such as triethylamine, N-ethyl-diisopropylamine or, preferably, N-methylmorpholine, is preferably used as the base.

The preparation of readily hydrolyzable esters of the thioesters of Formula III can be carried out in a manner known per se by esterifying the carboxy-lower alkyl group $R^{10}$ (as previously described for the products of formula Ib or I) and subsequently reacting the product with an esterifying agent yielding the readily hydrolyzable ester group, for example with the corresponding halide (e.g. the iodide), conveniently in the presence of a base, for example in the presence of an alkali metal hydroxide or alkali metal carbonate or in the presence of an organic amine such as triethylamine. The esterification is preferably carried out in an inert organic solvent such as dimethylacetamide, hexamethylphosphoric acid triamide, diemthyl sulphoxide or diemthylformamide. The esterification is preferably carried out at a temperature in the range of about 0°–40°C.

Preferred thioesters of formula III are those of the formula

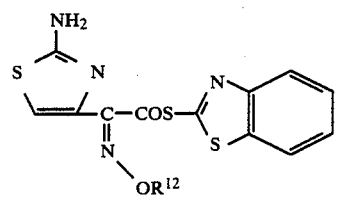   IIIb in which $R^{12}$ is lower alkoxycarbonyl-lower alkyl, phenyl-lower-alkoxycarbonyl-lower alky, nitrophenyl-lower alkoxycarbonyl-lower alkyl or tri-lower alkyl-silyl-lower-alkoxycarbonyl-lower alkyl.

Especially preferred thioesters of formula IIIb are those in which $R^{12}$ is lower alkoxycarbonylmethyl, phenyl-lower-alkoxycarbonylmethyl, nitrophenyl-lower-alkoxycarbonylmethyl or tri-lower alkyl-silyl-lower-alkoxycarbonylmethyl, especially 2-(2-amino-4-thiazolyl)-2-[[(Z)-1-(t-butoxycarbonyl)methoxy]imino]-acetic acid 2-benzthiazolyl thioester and 2-(2-amino-4-thiazolyl)-2-[[(Z)-(p-nitrobenzyloxycarbonyl)methoxy]imino]-acetic acid 2-benzthiazolyl thioester; and also those thioesters of formula IIIb in which $R^{12}$ is lower alkoxycarbonyl-1-methylethyl, 1-(phenyl-lower-alkoxycarbonyl)-1-methylethyl, 1-(nitrophenyl-lower-alkoxycarbonyl)-1-methylethyl or 1-(tri-lower alkyl-silyl-lower-alkoxycarbonyl)-1-methylethyl, especially 2-(2-amino-4-thiazolyl)-2[[(Z) -1-[2-(trimethylsilyl)ethoxycarbonyl]-1-methylethoxy]imino]-acetic acid 2-benzthiazolyl thioester, 2-(2-amino-4-thiazolyl)-2-[[(Z)-1-(p-nitrobenzyloxycarbonyl)-1-methylethoxy]imino]-acetic acid 2-benzthiazolyl thioester and 2-(2amino-4-thiazolyl)-2-[[(Z)-1-(t-butoxycarbonyl)-1-methylethoxy]imino]-acetic acid 2-benzthiazolyl thioester.

A particular problem arises in the preparation of the acids of formula Iv in which $R^{10}$ is t-alkoxycarbonyl-lower alkyl, for example the group —CH$_2$—COOC(R)$_3$ in which R represents $C_{1-3}$ -alkyl. The conventional manner for the preparation of these compounds, namely the reaction of the methyl or ethyl ester of the corresponding hydroxyimino compound with a halo-acetic acid C(R)$_3$-ester and subsequent saponification, does not yield the desired acid of formula IV in which $R^{10}$ is —CH$_2$—COOC(R)$_3$, because the group —COOC(R)$_3$ is saponified. It is therefore necessary to adopt a different procedure.

The aforementioned acid of formula IV in which $R^{10}$ is —CH$_2$—COOC(R)$_3$ can, however, be prepared in good yield when in place of the aforementioned methyl or ethyl ester there is used the allyl or p-nitrobenzyl ester, i.e. by cleaving off the group $R^5$ in an ester of the formula

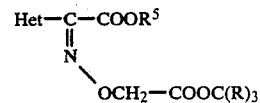   X in which Het is as above, R is $C_{1-3}$-alkyl and $R^5$ is allyl or p-nitrobenzyl.

The term "$C_{1-3}$-alkyl" embraces methyl, ethyl, n-propyl and isopropyl. The preferred group of the formula —COOC(R)$_3$ is that in which R is methyl, i.e. t-butoxycarbonyl.

According to one embodiment of the process provided by the invention, an ester of formula X in which R$^5$ is p-nitrobenzyl is cleaved hydrogenolytically. This cleavage is preferably carried out with the aid of hydrogen and a metal catalyst, preferably Raney-nickel, whereby the reaction can be accelerated by the additon of an organic base such as triethylamine. A lower alkanol such as methanol or ethanol is preferably used as the solvent. The reaction is preferably carried out at a temperature between about 0° C. and 80° C, especially at room temperature.

According to a further embodiment of the process provided by the invention, an ester of formula X in which R$^5$ is allyl is cleaved catalytically. This cleavage can be carried out by the action of a palladium compound in the presence of triphenylphosphine or a tri-(lower-alkyl)-phosphite (e.g. triethyl phosphite). As palladium compounds there come into consideration palladium/carbon and palladium salts, especially salts with hydrochloric acids such as hydrochloric acid or hydrobromic acid or with lower alkanecarboxylic acids such as acetic acid or propionic acid. Palladium-organic complexes with triphenylphosphine or a tri-(lower-alkyl)-phosphite such as triethyl phosphite, also come into consideration, whereby the reaction can also be carried out without the further addition of triphenylphosphine or a tri-(lower-alkyl)-phosphite. A further reaction partner is an alkali metal alkanoate, (e.g. sodium acetate) or, preferably, sodium-2-ethylcaproate, or also an organic base such as triethylamine or N-methylmorpholine. The reaction can be carried out at a temperature between about 0° C. and 100° C., but preferably at room temperature (when palladium/carbon is used the reaction is carried out at a somewhat higher temperature; about 50°–80° C.). The reaction is preferably carried out in an inert organic solvent (e.g. in ethyl acetate or methylene chloride).

The above p-nitrobenzyl esters of formula X can be prepared from a Het-2-(Z)-hydroxyimino-acetic acid by the addition of p-nitrobenzyl bromide or p-nitrobenzyl chloride and an alkali metal iodide and subsequently of a compound of the general formula Hal—CH$_2$—COO—C(R)$_3$  XI in which R has the above significance and Hal represents chlorine, bromine or iodine,
in the presence of a base such as an alkali carbonate, triethylamine or N-ethyldiisopropylamine and an alkali metal iodide. The allyl esters of formula X can be prepared starting from diketene, chlorine gas and allyl alcohol, which are converted into allyl 4-chloroacetoacetate. The latter is nitrosated with nitrous acid and subsequently converted with thiourea into an allyl Het-2-(Z)-hydroxyimino-acetate which is thereupon converted into the allyl ester of formula X by reaction with the above compound of formula XI in the presence of a base such as an alkali carbonate, triethylamine or N-ethyldiisopropylamine.

The starting materials of formula II can be prepared according to various methods. For the preparation of optically uniform compounds of formula II having the 3S-cis configuration, one can start from isopropylidene-L-glyceraldehyde in accordance with the following Formulae Schemes (Schemes I–VII). The preparation of optically uniform compounds of formula II having the 3S-trans configuration is illustrated in Schemes V and VI:

Scheme I

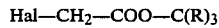

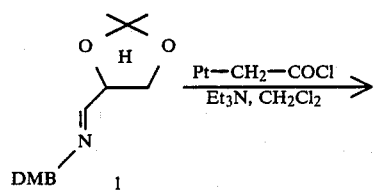

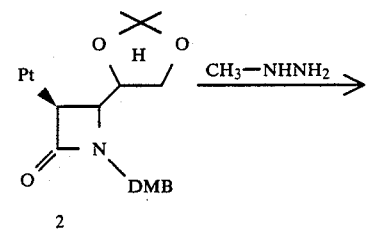

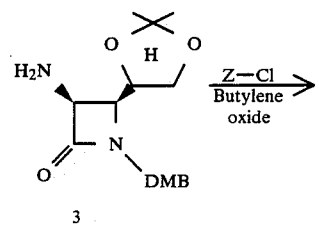

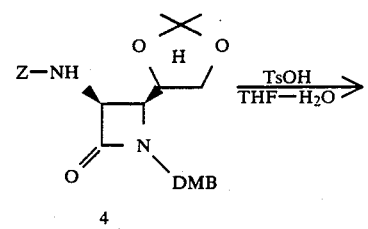

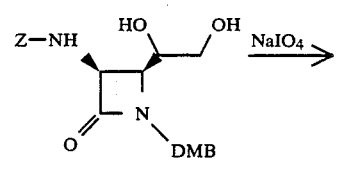

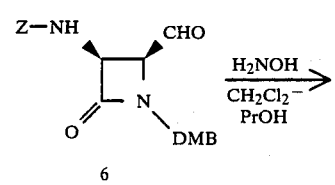

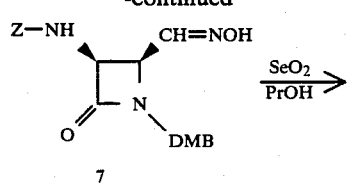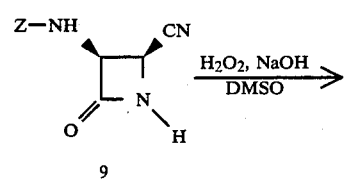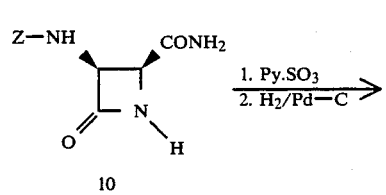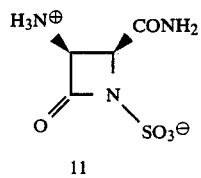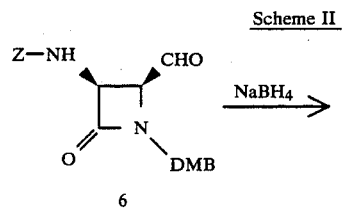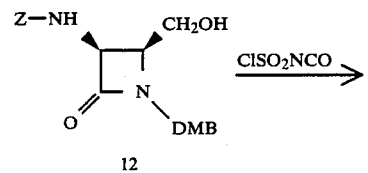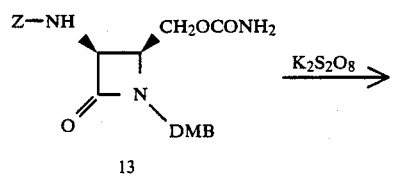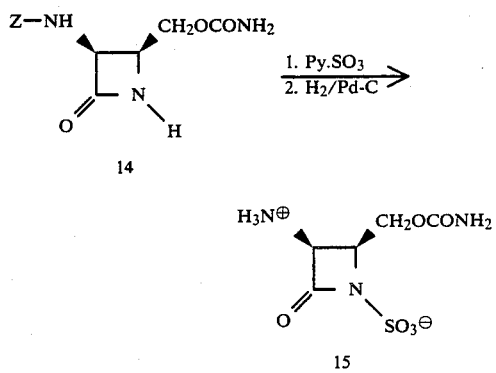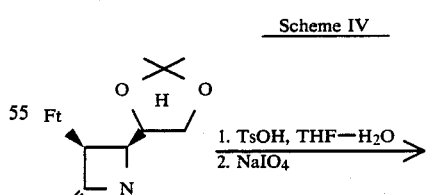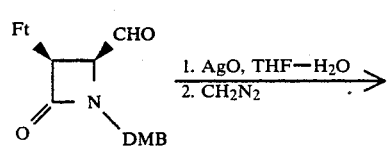

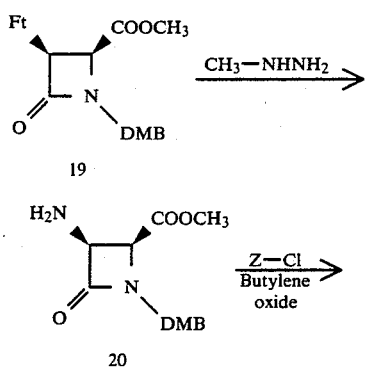
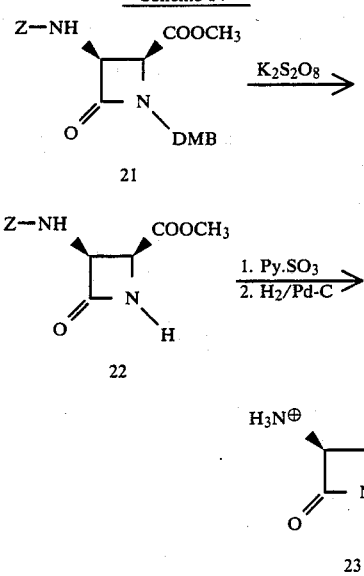
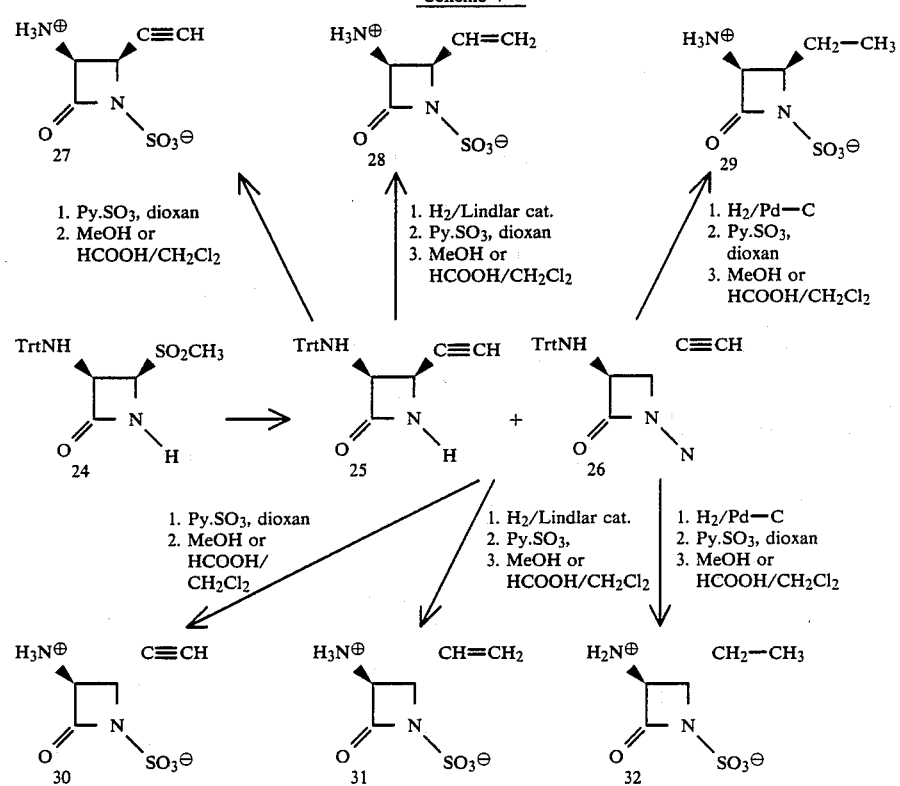

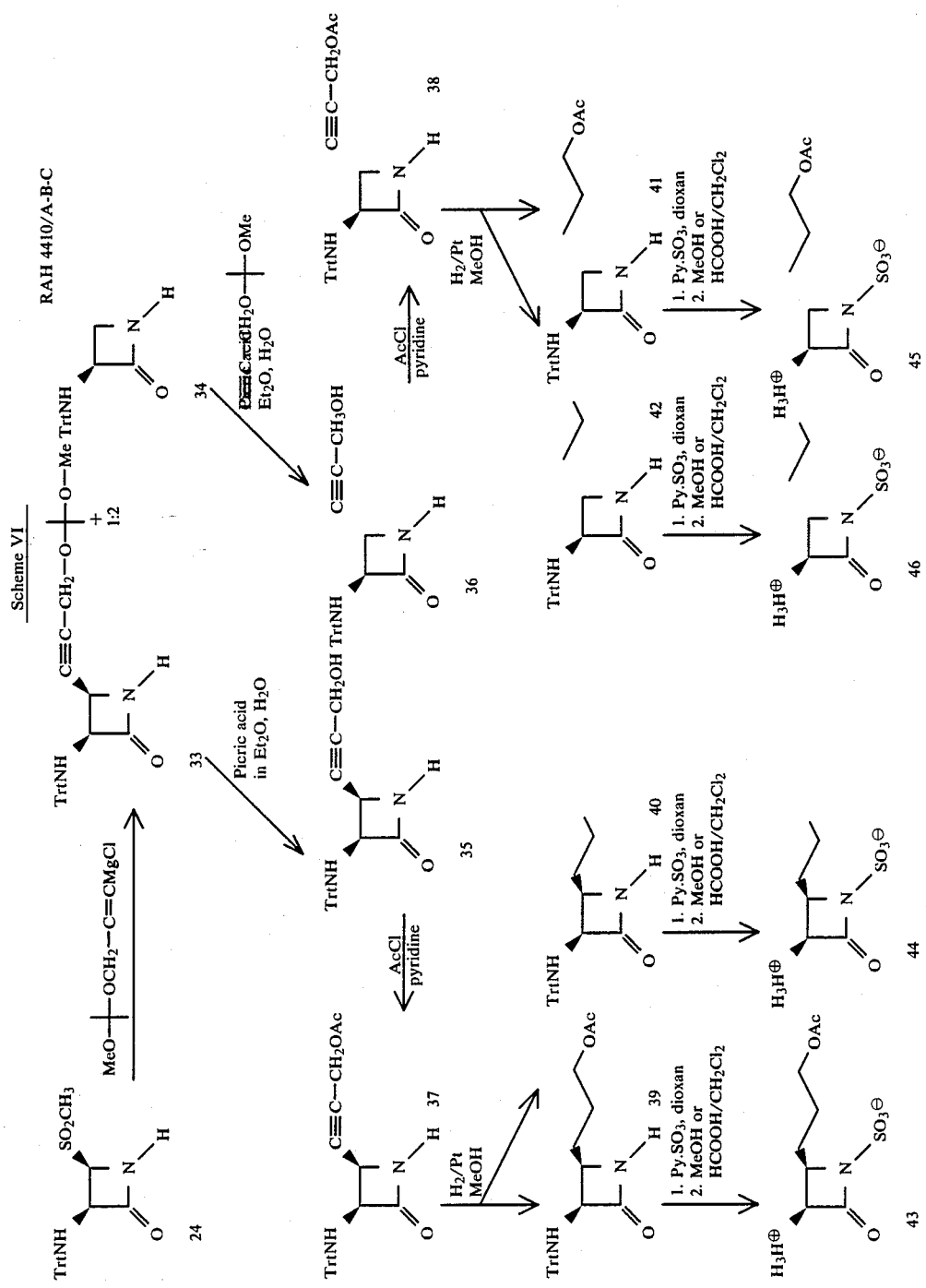

Scheme VII

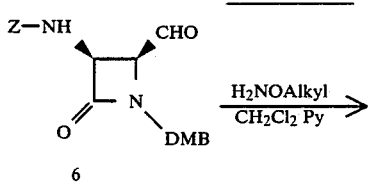

6

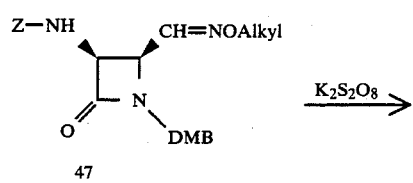

47

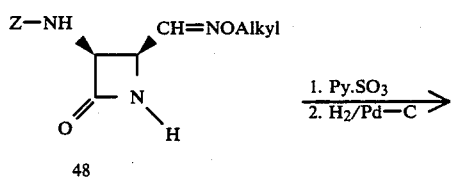

48

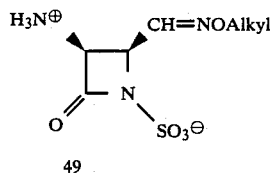

49

| Abbreviations used in Schemes I-VII | | |
|---|---|---|
| DMB | = | 2,4-dimethoxybenzyl |
| Ft | = | phthalimido |
| Et | = | ethyl |
| Me | = | methyl |
| TSOH | = | p-toluenesulphonic acid |
| THF | = | tetrahydrofuran |
| PrOH | = | n-propanol |
| DMSO | = | dimethyl sulphoxide |
| Py | = | pyridine |
| Py.SO$_3$ | = | sulphur trioxide-pyridine complex |
| Z | = | benzyloxycarbonyl |
| Trt | = | trityl |
| Ac | = | lower alkanoyl (e.g. acetyl). |

A sub-group of novel compounds of formula I comprises those of the formula

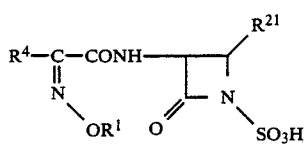

Ic in which R$^1$ is as in formula I, R$^4$ is the same as Het in formula I and R$^{21}$ is the same
of R$^2$ given in formula I, the group =NOR$^1$ being present at least partially in the syn-form, with the proviso that at least one of the following two conditions is fulfilled:
(a) R$^4$ = 2-amino-4-oxazolyl, 2-amino-6-pyridyl, 2-amino-4-imidazolyl, 5-amino-3-(1,2,4-thiadiazolyl) or 2-pyrazol-3-yl, (b) R$^{21}$ = hydroxyiminomethyl, lower alkoxyiminomethyl, lower alkoxycarbonyl-lower alkenyl or carbamoyl-lower alkenyl, in racemic form or in the form of the 3S-enantiomer, and readily hydrolyzable esters and pharmaceutically compatible salts of these compounds.

Sub-groups of compounds of formula Ic comprise those of the formula

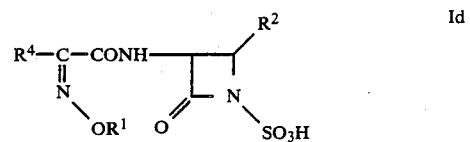

Id in which R$^1$ and R$^2$ are as in formula I above and R$^4$ is 2-amino-4-oxazolyl, 2-amino-6-pyridyl, 2-amino-4-imidazolyl, 5-amino-3-(1,2,4-thiadiazolyl) or 2-pyrazol-3-yl, the group =NOR$^1$ being present at least partially in the syn-form,
in racemic form or in the form of the 3S-enantiomer, and readily hydrolyzable esters and pharmaceutically compatible salts of these compounds; and those of the formula

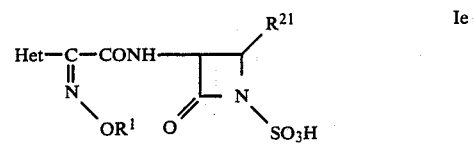

Ie in which R$^1$ and Het are as in formula I and R$^{21}$ is hydroxyiminomethyl, lower alkoxyiminomethyl, lower alkoxycarbonyl-lower alkenyl or carbamoyl-lower alkenyl, the group =NOR$^1$ being present at least partially in the syn-form,
in racemic form or in the form of the 3S-enantiomer, and readily hydrolyzable esters and pharmaceutically compatible salts of these compounds.

The novel 1-sulpho-2-oxoazetidine derivatives of formula Ic and their readily hydrolyzable esters and pharmaceutically compatible salts can be manufactured in accordance with the invention by
(a) reacting a carboxylic acid of the formula

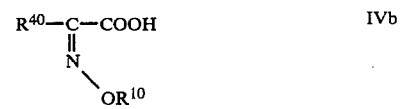

IVb in which R$^{10}$ is as in formula III above and R$^{40}$ is the same as R$^4$ in formula Ic above, whereby, however, an amino group present can be protected, and the group =NOR$^{10}$ is present at least partially in the syn-form,
or a functional derivative thereof with a compound of the formula which is present in racemic form or in the form of the 3S-enantiomer

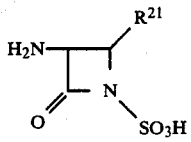

in which $R^{21}$ is as in formula Ic above,
or with a salt thereof and subsequently cleaving off an amino protecting group which may be present, or (b) sulphonating a compound of the formula which is present in racemic or in the form of the 3S-enantiomer

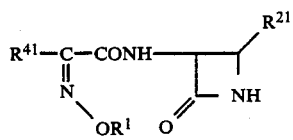

in which $R^1$ and $R^{21}$ are as in formula I or formula Ic above and $R^{41}$ is the same as $R^4$ in formula Ic above, whereby, however, an amino group present is protected, and the group $=NOR^1$ is present at least partially in the syn-form,
or a salt thereof and subsequently cleaving off the amino protecting group,
or (c) for the manufacture of a compound of formula Ic in which $R^{21}$ is hydroxyiminomethyl, lower alkoxyiminomethyl or carbamoylvinyl, reacting a compound of the
formula which is present in racemic form or in the form of the 3S-enantiomer

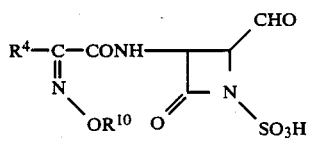

in which $R^4$ is as in formula Ic above and $R^{10}$ is as in formula Ib above, and the group $=NOR^{10}$ is present at least partially in the syn-form,
with hydroxylamine, with a 0-lower-alkylhydroxylamine or with carbamoylmethylenetriphenylphosphorane and, if desired, lower alkylating a product obtained in which $R^{21}$ is hydroxyiminomethyl,
or (d) for the manufacture of a compound of formula Ic in which $R^1$ is carboxy-lower alkyl, converting the group $R^{13}$ in a compound of the formula which is present in racemic form or in the form of the 3S-enantiomer

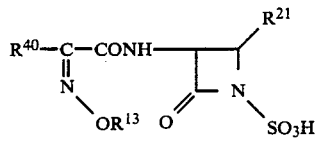

in which $R^{21}$ and $R^{40}$ are as above and $R^{13}$ is tri-lower alkyl-silyl-lower-alkoxycarbonyl-lower alkyl, lower alkoxycarbonyl-lower alkyl, phenyl-lower-alkoxycarbonyl-lower alkyl or nitrophenyl-lower-alkoxycarbonyl-lower alkyl, the group $=NOR^{13}$ being present at least partially in the syn-form, into carboxy-lower alkyl,
or (e) converting a compound of formula Ic or a readily hydrolyzable ester thereof into a pharmaceutically compatible salt.

The reaction of a carboxylic acid of formula IVb or a functional derivative thereof with a compound of formula IIa can be carried out in a manner known per se. Where the free carboxylic acid of formula IVb is used, the reaction is preferably carried out in the presence of a condensation agent which can be, for example, a substituted carbodiimide such as N,N-dicyclohexylcarbodiimide, a quaternary 2-halopyridinium salt such as 2-chloro-1-methylpyridinium iodide or 1-chloro-N,N,2-trimethyl-1-propenamine. As functional derivatives of the carboxylic acids of formula IVb there come into consideration acid halides (e.g. acid chlorides), acid anhydrides (e.g. mixed anhydrides with $C_{1-7}$-alkanecarboxylic acids such as acetic acid), acid azides, active amides (e.g. amides with pyrazole, imidazole, benztriazole), active esters (e.g. a $C_{1-7}$-alkyl, methoxymethyl, 2-propynyl, 4-nitrophenyl or hydroxysuccinimide ester) or active thioesters (e.g. esters with 2-pyridinethiol or 2-benzthiazolylthiol). The 2-benzthiazolyl thioesters are described above.

The reaction of a compound of formula IVb or a functional derivative thereof with a compound of formula IIa is conveniently carried out in an inert organic solvent, for example in a chlorinated hydrocarbon such as methylene chloride or chloroform, in an ether such as tetrahydrofuran or dioxan, in an ester such as ethyl acetate, in a ketone such as acetone, in an aprotic solvent such as acetonitrile, dimethylformamide or dimethylacetamide or in a mixture of one of these solvents with water. The reaction is conveniently carried out at a temperature between about $-40°$ C. and $+60°$ C., advantageously between $-15°$ C. and $+25°$ C., especially between $0°$ C. and $20°$ C. The reaction is conveniently carried out using about stoichiometric amounts of the reactants or using a slight excess of the carboxylic acid of formula IVb or of the functional derivative thereof. The reaction is advantageously carried out in the presence of a base such as, for example, in the presence of an organic amine such as triethylamine or N-methylmorpholine or in the presence of an alkali metal bicarbonate such as sodium bicarbonate.

Where the group $R^{40}$ in the starting material of formula IVa or functional derivative thereof contains an amino substituent, then this can preferably remain unprotected (since thereby one reaction step, namely the subsequent cleavage of the amino protecting group, can be dispensed with). However, $R^{40}$ can also contain a protected amino group. The amino protecting group can be a conventional amino protecting group; for example, a protecting group which is cleavable by acid hydrolysis such as t-butoxycarbonyl, benzhydryl, trityl or formyl, a protecting group which is cleavable by basic hydrolysis such as trifluoroacetyl or a chloroacetyl, bromoacetyl or iodoacetyl group which can be cleaved off using thiourea. The amino group can also be protected by salt formation with a mineral acid (e.g. hydrochloric acid). After the reaction of a carboxylic acid of formula IVb with a compound of formula IIa or of a functional derivative of a carboxylic acid of formula IVb with a compound of formula IIa, an amino protecting group which may be present is cleaved off. Protecting groups which are cleavable by acid hydrolysis are preferably removed with the aid of a lower alkanecarboxylic acid which, if desired, can be halogenated. In particular, there is used hydrochloric acid, formic acid or trifluoroacetic acid (the latter optionally in the presence of anisole) or also pyridinium hydrochloride. This cleavage is usually carried out at room temperature, although it can also be carried out at a slightly higher or slightly lower temperature (e.g. a temperature in the range of about 0° C. to +40° C.). Protecting groups which are cleavable using alkali are generally hydrolyzed using dilute aqueous caustic alkali at 0° C. to 30° C. The chloroacetyl, bromoacetyl and iodoacetyl protecting groups can be cleaved off using thiourea in an acidic, neutral or alkaline medium at about 0°–30° C.

In accordance with variant (b) of the process in accordance with the invention, a compound of formula XII is sulphonated. This sulphonation can be carried out in a manner known per se by reaction with sulphur trioxide or a reactive derivative thereof, for example complexes of sulphur trioxide with an organic base such as pyridine, dimethylformamide, picoline etc. The reaction is carried out, for example, at about −10° C. to +80° C. in an inert organic solvent, for example in an ether such as dioxan, in an ester such as ethyl acetate, in a chlorinated hydrocarbon such as methylene chloride or in acetonitrile, dimethylformamide or pyridine.

In variant (b) of the process in accordance with the invention, the amino group present in $R^{41}$ is protected. The amino protecting groups are of the same kind as the amino protecting groups in the starting materials of formula IVb and they are also cleaved off in the same manner as described earlier.

The reaction of a compound of formula VIIa with hydroxylamine yields a compound of formula Ic in which $R^{21}$ is hydroxyiminomethyl. This reaction is preferably carried out in an inert organic solvent (e.g. methylene chloride), preferably in the presence of an organic base such as pyridine. The reaction is preferably carried out at about 0°–60° C., especially at about room temperature. If an 0-lower-alkylhydroxylamine is used in place of hydroxylamine, there is obtained a compound of formula Ic in which $R^{21}$ represents lower alkoxyiminomethyl.

If the starting material of formula VIIa is reacted with carbamoylmethylenetriphenylphosphorane there is obtained a compound of formula Ic in which $R^{21}$ is carbamoylvinyl. This reaction is preferably carried out in an inert solvent such as methylene chloride, tetrahydrofuran or dioxan and at a temperature between about room temperature and the boiling point of the mixture.

If desired, a thus-obtained compound of formula Ic in which $R^{21}$ is hydroxyiminomethyl can be lower alkylated. This lower alkylation is preferably carried out using a $C_{1-7}$-alkyl iodide, advantageously in an inert organic solvent such as methylene chloride, preferably in the presence of an organic base such as pyridine. The lower alkylation is preferably carried out at a temperature of about 0°–60° C., especially at room temperature.

The conversion of the group $R^{13}$ in a compound of formulae. If into carboxy-lower alkyl is carried out in the same manner as described above in connection with the compounds of formulae Ib and I. This also applies for the manufacture in accordance with the invention of pharmaceutically compatible salts of the compounds of formula Ic.

The compounds of formula I and their readily hydrolyzable esters and pharmaceutically compatible salts have a broad antimicrobial spectrum of activity, especially aqainst gram-negative microorganisms such as, for example, pathogens of the family Enterobacteriacae, for example *Escherichia coli*, Proteus spp., Serratia spp. and *Psuedomonas aeruginosa*.

These proucts can accordingly be used for the treatment and prophylaxis of infectious diseases. A daily dosage of about 10–600 mg/kg body weight comes into consideration for adults.

The minimum inhibitory concentration (MIC, μg/ml) in vitro of some representative products is given in the Tables hereinafter in which specific compounds obtained in the Examples hereinafter are referred to.

TABLE

| Organism | Example 7 | Example 11a | Example 13 | Example 27 | Example 29 | Example 31 | Example 34 | Example 35d |
| --- | --- | --- | --- | --- | --- | --- | --- | --- |
| E. cloacae 15M | 0.4 | 3.1 | 1.6 | 0.5 | 0.12 | 0.25 | 0.4 | 0.2 |
| S. marcescens 80315 | 0.4 | 3.1 | 3.1 | 0.5 | 0.12 | 0.25 | 0.4 | 0.2 |
| Pr. mirabilis 2117 | ≦0.05 | 0.8 | 0.8 | 0.06 | ≦0.03 | 0.06 | 0.2 | 0.1 |
| Pr. vulgaris 1028 | ≦0.05 | 0.8 | 0.4 | ≦0.06 | ≦0.03 | 0.12 | 0.2 | 0.1 |
| Ps. aeruginosa 799/61 | 0.8 | 1.6 | 0.2 | 0.12 | 0.12 | 0.06 | 0.1 | ≦0.1 |
| E. coli UB 1005 | 0.2 | 1.6 | 0.8 | 0.5 | 0.12 | 0.12 | 0.4 | 0.2 |
| K. pneumoniae 418 | 0.1 | 0.8 | 0.8 | 1 | 0.12 | 0.12 | 0.8 | ≦0.1 |
| K. oxytoca 22812 | — | 1.6 | 0.8 | 1 | 0.12 | 0.5 | 0.2 | 0.4 |
| Organism | Example 36a | Example 44 | Example 45 | Example 46 | Example 47 | Example 48 | Example 49 | Example 50 |
| E. cloacae 15M | 0.5 | 4 | 0.5 | 0.25 | 16 | 0.5 | 4 | 16 |
| S. marcescens 80315 | 2 | 8 | 1 | 0.25 | 32 | 0.5 | 8 | 32 |
| Pr. mirabilis 2117 | 0.12 | 4 | 0.5 | 0.12 | 4 | 0.5 | 2 | 16 |
| Pr. vulgaris 1028 | 0.25 | 2 | 0.25 | 0.12 | 2 | 0.5 | 16 | 64 |
| Ps. aeruginosa 799/61 | 0.25 | 1 | 0.12 | 0.5 | 4 | 0.12 | 0.5 | 8 |
| E. coli UB 1005 | 0.5 | 4 | 0.25 | 0.25 | 4 | 0.25 | 2 | 8 |
| K. pneumoniae 418 | 0.25 | 4 | 0.5 | 0.06 | 8 | 0.25 | 4 | 8 |
| K. oxytoca 22812 | 2 | 4 | 0.5 | 4 | 4 | 0.5 | 64 | >128 |

| Organism | Example 27 | Example 29 |
| --- | --- | --- |
| Ent. cloaceae 4W-142 | 2 | 4 |

| | | |
|---|---|---|
| C. freundii 4f52 | 4 | 8 |
| P. vulgaris 10610 | ≦0.25 | 0.25 |
| Ps. aeruginosa 5F 81-1 | 8 | 4 |
| S. marcescens 1 × 172 | 2 | 0.5 |

The products provided by the present invention can be used as medicaments; for example, in the form of pharmaceutical preparations which contain them in admixture with a pharmaceutical, organic or inorganic inert carrier material which is suitable for parenteral administration.

The following Examples illustrate the present invention:

EXAMPLE 1

(a) 18 mg (0.087 mmol) of (3S,4S)-3-amino-2-oxo-4-propyl-1-azetidinesulphonic acid, 32 mg (0.095 mmol) of 2-(2-amino-4-thiazolyl)-2-(Z)-methoxyimino-acetic acid 2-benzthiazolyl thioester and 14.5 mg (0.143 mmol) of triethylamine are stirred in 1 ml of dichloromethane for 2 hours. After evaporation of the solvent, the residue is taken up in 5 ml of water, washed five times with 5 ml of ether each time and lyophilized. There are obtained 35 mg of (3S,4S)-3-[(Z)-2-(2-amino-4-thiazolyl)-2-(methoxyimino)acetamido]-2-oxo-4-propyl-1-azetidinesulphonic acid triethylamine salt as a colourless amorphous product.

IR (KBr, cm$^{-1}$): 3384, 3312, 3207, 1763, 1670, 1621, 1537, 1266, 1230, 1044.

NMR (DMSO, ppm): 9.24 (d, J=8.5 Hz, 1H) 7.17 (s, 2H); 6.64 (s, 1H); 4.50 (dd, J=2.5/8.5 Hz; 1H), 3.79 (s, 3H), 3.59 (m, 2H); 3.07 (q, J=7.5 Hz, 6H), ca. 2 (m, br, 1H); 1.4 (m, br, 1H); 1.17 (t, J=7.5 Hz, 9H); 0.88 (m, 3H).

The 2-(2-amino-4-thiazolyl)-2-(Z)-methoxyiminoacetic acid 2-benzthiazolyl thioester used as the starting material can be prepared as follows:

(b) 3.93 g of triphenylphosphine and 5 g of dithio-bis-benzthiazole are suspended in 50 ml of dichloromethane and the suspension is stirred at room temperature for about 30 minutes. After cooling to 0° C., 2 g of 2-(2-amino-4-thiazolyl)-2-(Z)-methoxyimino-acetic acid are added and the mixture is stirred at 0° C. for 3 to 4 hours. For the working-up, the insoluble material is filtered off under suction and washed with a small amount of cold methylene chloride. The solid is suspended in 25 ml of ethyl acetate, the suspension is stirred at 0° C. for 30 minutes, the solid material is filtered off under suction and washed with ethyl acetate. After recrystallization from tetrahydrofuran/dichloromethane, there is obtained 2-(2-amino-4-thiazolyl)-2-(Z)-methoxyimino-acetic acid 2-benzthiazolyl thioester of melting point 128°–130° C.

The (3S,4S)-3-amino-2-oxo-4-propyl-1-azetidinesulphonic acid used as the starting material can be prepared as follows:

(c) 84 ml of a 1.0N solution of ethylmagnesium bromide in tetrahydrofuran are added dropwise to 10.8 g (84 mmol) of 3-(2-methoxy-2-propoxy)-propyne dissolved in 80 ml of dry tetrahydrofuran. The solution is held at room temperature by cooling with an ice-bath and, after the addition of the ethylmagnesium bromide, the mixture stirred at room temperature for 30 minutes. The mixture is added dropwise at −70° C. to −40° C. to 8.5 g (20.9 mmol) of (3R,4R)-4-methylsulphonyl-3-tritylamino-2-azetidinone dissolved in 50 ml of dry tetrahydrofuran and the resulting mixture is stirred at −30° C. for 30 minutes and at room temperature for 1.75 hours. The brown solution obtained is diluted with 1 l of ether and the ether phase is washed with 300 ml of saturated aqueous ammonium chloride solution and subsequently three times with 300 ml of water each time, dried and evaporated. The residue is chromatographed over 500 g of silica gel with t-butyl methyl ether/n-hexane (1:1). After a forerun of 1.8 l, there are obtained 0.9 l of eluate containing 1.2 g (13%) of substance A, 0.9 l of eluate containing 3.0 g (32%) of a mixture of substance A and substance B and finally 1.8 l of eluate containing 3.2 g (34%) of substance B.

Substance A: Acetone methyl 3-[(3S,4R)-2-oxo-3-tritylamino-4-azetidinyl]-2-propynyl acetal.

NMR (CDCL$_3$, ppm): 1.23 (s, 6H), 3.03 (s, 3H), 3.08 (d, J=10.5 Hz, 1H), 3.57 (d, tr, J=2 Hz or 5 Hz, 1H), 3.94 (d, J=2 Hz, 1H), 4.39 (dd, J=5 or 10.5 Hz, 1H), 5.76 (s, 1H), 7.15–7.6 (m, 15H).

IR (KBr, cm$^{-1}$:) 706, 748, 1034, 1070, 1490, 1956, 1766, 3318, cm$^{-1}$.

Substance B: Acetone methyl 3-[(3S,4S)-2-oxo-3-tritylamino-4-azetidinyl]-2-propynyl acetal.

NMR (CDCl$_3$, ppm): 1.30 (s, 6H), 2.87 (d, J=9 Hz, 1H), 3.14 (s, 3H), 3.39 (q, J=2 Hz, 1H), 4.26 (dd, J=2 or 9 Hz, 1H), 5.82 (s, 1H), 7.15–7.55 (m, 15H).

(d) 2.4 g (5.3 mmol) of acetone methyl 3-[(3S,4S)-2-oxo-3-tritylamino-4-azetidinyl]-2-propynyl acetal are stirred at room temperature for 15 minutes in 50 ml of ether and 50 ml of 1% aqueous picric acid. The aqueous phase is separated and the ether phase is washed with saturated aqueous sodium bicarbonate solution and with water, dried and evaporated. The residue corresponds to 1.8 g (89%) of 3-[(3S,4S)-2-oxo-3-tritylamino-4-azetidinyl]-2-propynol.

NMR (CDCl$_3$, ppm): 2.3 (s, br, 1H), 2.8 (s, br, 1H), 3.35 (1H), 4.0 (2H), 4.2 (1H), 6.45 (s, 1H), 7.0–7.8 (m, 15H).

0.88 g (1.9 mmol) of acetone methyl 3-[(3S,4R)-2-oxo-3-tritylamino-4-azetidinyl]-2-propynyl acetal are converted in the above manner with picric acid into 0.67 g (90%) of 3-[(3S,4R)-2-oxo-3-tritylamino-4-azetidinyl]-2-propynol.

NMR (CDCl$_3$, ppm): 1.56 (1H), 3.0 (d, J=11 Hz, 1H), 3.72 (d, tr, J=1.5 or 5 Hz, 1H), 4.07 (d, J=4.5 Hz, 2H), 4.46 (dd, J=5 and 11 Hz, 1H), 5.84 (s, 1H), 7.2–7.6 (m, 15H).

(e) 2.03 g (5.31 mmol) of 3-[(3S,4R)-2-oxo-3-tritylamino-4-azetidinyl]-2-propynol, 0.65 g (6.37 mmol) of acetic anhydride and 5.04 mg (6.38 mmol) of pyridine are stirred at room temperature for 3.5 hours in 10 ml of methylene chloride. The solution is subsequently diluted with 100 ml of methylene chloride, poured into 50 ml of ice-water, the aqueous phase is separated, the methylene chloride phase is washed twice with 50 ml of water each time, dried and evaporated. The residue consists of 1.15 g (51%) of 3-[(3S,4R)-2-oxo-3-tritylamino-4-acetidinyl]-2-propynyl acetate.

NMR (CDCl$_3$, ppm): 1.91 (s, 3H), 3.01 (d, J=11 Hz, 1H), 3.64 (d, br, J=2 Hz and 5 Hz, 1H), 4.46 (dd, J=5 and 11 Hz, 1H), 4.53 (d, J=2 Hz, 2H), 5.68 (s, 1H), 7.2–7.6 (m, 15H).

IR (KBr, cm$^{-1}$): 705, 744, 1236, 1488, 1595, 1732, 1757, 2239, 2336, 3336.

From 3-[(3S,4S)-2-oxo-3-tritylamino-4-azetidinyl]-2-propynol there is obtained in the same manner 3-[(3S,4S)-2-oxo-3-tritylamino-4-azetidinyl]-2-propynyl acetate.

NMR (CDCl$_3$, ppm): 2.07 (s, 3H), 2.84 (d, J=9 Hz, 1H), 3.39 (q, J=2 Hz, 1H), 4.29 (dd, J=2 and 9 Hz, 1H), 4.50 (d, J=2Hz, 2H), 5.81 (s, 1H), 7.2–7.6 (m, 15H).

IR (KBr, cm$^{-1}$): Identical with 3-[(3S,4R)-2-oxo-3-tritylamino-4-azetidinyl]-2-propynyl acetate.

(f) 410 mg (0.97 mmol) of 3-[(3S,4R)-2-oxo-3-tritylamino-4-azetidinyl]-2-propynyl acetate dissolved in 40 ml of methanol are hydrogenated over 100 mg of platinum oxide for 10 minutes. The catalyst is filtered off under suction and the filtrate is evaporated. The residue is chromatographed over 70 g of silica gel with t-butyl methyl ether/n-hexane (2:1). After a forerun of 200 ml, there are obtained 120 ml of eluate containing 180 mg (50%) of (3S,4R)-4-propyl-3-tritylamino-2-azetidinone. After a further 500 ml, there are obtained 420 ml of eluate containing 67 mg (16%) of 3-[(3S,4R)-2-oxo-3-tritylamino-4-azetidinyl]-propyl acetate.

3-[(3S,4R)-2-Oxo-3-tritylamino-4-azetidinyl]-propyl acetate:

NMR (CDCl$_3$, ppm): 0.9–1.6 (m, 4H), 2.0 (s, 3H), 2.6 (1H), 3.2 (1H), 3.85 (2H), 4.4 (1H), 6.2 (1H), 7.2–7.6 (15H).

(3S,4R)-4-Propyl-3-tritylamino-2-azetidinone:

NMR (CDCl$_3$, ppm): 0.5–1.3 (7H), 2.7 (1H), 3.1 (1H), 4.35 (1H), 6.1 (1H), 7.1–7.7 (15H).

420 mg (1 mmol) of 3-[(3S,4S)-2-oxo-3-tritylamino-4-azetidinyl]-2-propynyl acetate are hydrogenated in the same manner with platinum oxide and the product is chromatographed over 70 g of silica gel with t-butyl methyl ether/n-hexane (1:1). After 125 ml, there are obtained 300 mg of (3S,4S)-4-propyl-3-tritylamino-2-azetidinone and, after 275 ml, there are obtained 87 mg of 3-[(3S,4S)-2-oxo-3-tritylamino-4-azetidinyl]-propyl acetate.

3-[(3S,4S)-2-Oxo-3-tritylamino-4-azetidinyl]-propyl acetate:

NMR (CDCl$_3$, ppm) 0.5–1.4 (4H), 2.0 (s, 3H), 2.7 (1H), 3.0 (1H), 3.8 (1H), 6.15 (1H), 7.0–7.7 (15H).

(3S,4S)-4-Propyl-3-tritylamino-2-azetidinone:

NMR (CDCl$_3$, ppm): 0.4–1.3 (7H), 3.0 (2H, 3.7 (1H), 6.3 (1H), 7.2–7.7 (15H).

(g) 180 mg (0.49 mmol) of (3S,4S)-4-propyl-3-tritylamino-2-azetidinone and 239 mg (1.5 mmol) of sulphur trioxide-pyridinium complex are stirred at room temperature for 21 hours in 2 ml of dry dioxan. The residue is separated by centrifugation, dissolved in 10 ml of water, neutralized with sodium bicarbonate and the aqueous solution is extracted with methylene chloride. The methylene chloride phase is evaporated, the residue is dissolved in 1 ml of methylene chloride and treated with 40 µl of formic acid (98%–100%). The product precipitates and is filtered off under suction. There are obtained 18 mg (18%) of (3S,4S)-3-amino-2-oxo-4-propyl-1-azetidinesulphonic acid which can be used directly for the reaction in accordance with the first paragraph of this Example.

In an analogous manner, from (3S,4R)-4-propyl-3-tritylamino-2-azetidinone there is obtained crude (3S,4R)-3-amino-2-oxo-4-propyl-1-azetidinesulphonic acid which is likewise used directly.

EXAMPLE 2

(a) In the same manner as described in Example 1(a), from 20 mg of (3S,4R)-3-amino-4-(3-acetoxypropyl)-2-oxo-1-azetidine sulphonic acid there are obtained 20 mg of (3S,4R)-3-[(Z)-2-(2-amino-4-thiazolyl)-2-(methoxyimino)acetamido]-4-(3-acetoxypropyl)-2-oxo-1-azetidinesulphonic acid triethylamine salt. For purification, this salt is chromatographed on reverse-phase silica gel using water/methanol (4:1) for the elution. 6 mg of pure products are obtained as a lyophilizate.

IR (KBr, cm$^{-1}$): 3410, 3328, 3240, 1772, 1741, 1681 1545, 1247, 1045.

NMR (DMSO, ppm): 9.27 (d, J=9 Hz), 7.1 (s, br. 2H); 6.69 (s, 1H), 5.10 (dd, J=5 and 9 Hz, 1H); ca. 3.9 (m, 3H); 3.80 (s, 3H); 3.03 (q, J=7 Hz, 6H); 2.00 (s, 3H), 1.3–1.8 (m, 4H); 1.17 (t, J=7 Hz, 9H).

The (3S,4R)-3-amino-4-(3-acetoxypropyl)-2-oxo-1-acetidinesulphonic acid used as the starting material can be prepared as follows:

(b) 67 mg (0.16 mmol) of 3-[(3S,4R)-2-oxo-3-tritylamino-4-azetidinyl]-propyl acetate are converted in an analogous manner to that described in Example 4(d) with sulphur trioxide-pyridinium complex into (3S,4R)-3-amino-4-(3-acetoxypropyl)-2-oxo-1-azetidinesulphonic acid which is acylated directly in the above reaction.

EXAMPLE 3

(a) In the same manner as described in Example 1(a), from 36 mg of (3S,4S)-3-amino-4-(3-acetoxypropyl)-2-oxo-1-azetidinesulphonic acid there are obtained 37 mg of (3S,4S)-3-[(Z)-(2-amino-4-thiazolyl)-2-(methoxyimino)acetamido]-4-(3-acetoxypropyl)-2-oxo-1-azetidinesulphonic acid triethylamine salt as an amorphous lyophilizate.

IR (KBr, cm$^{-1}$): 3404, 3321, 1766, 1735, 1671, 1621, 1538, 1242, 1043.

NMR (DMSO, ppm): 9.29 (d, J=8.5 Hz, 1H), 7.20 (s, br, 1H); 6.68 (s, 1H); 4.51 (dd, J=2.5 and 8.5 Hz, 1H); ca. 4.0 (m, 2H), 3.82 (s, 3H), 3.07 (q, J=ca. 7.5 Hz, 6H); 2.0 (s, 3H); ca. 1.5 (m, 3H); 1.17 (t, J=7.5 Hz, 9H).

The (3S,4S)-3-amino-4-(3-acetoxypropyl)-2-oxo-1-azetidinesulphonic acid used as the starting material can be prepared as follows:

(b) 87 mg (0.20 mmol) of 3-[(3S,4S)-2-oxo-3-tritylamino-4-azetidinyl]-propyl acetate are converted in a manner analogous to that described in Example 1(g) or 4(d) into (3S,4S)-3-amino-4-(3-acetoxypropyl)-2-oxo-1-azetidinesulphonic acid which is used directly as the crude product.

EXAMPLE 4

38 mg (0.2 mmol) of (3S,4R)-3-amino-4-ethynyl-2-oxo-1-azetidinesulphonic acid, 77 mg (0.22 mmol) of 2-(2-amino-4-thiazolyl)-2-(Z)-methoxyimino-acetic acid 2-benzthiazolyl thioester and 56 μl (0.4 mmol) of triethylamine are stirred at room temperature for 2 hours in 1 ml of acetone/water (4:1). The mixture is then filtered and evaporated. The residue is chromatographed over reverse-phase silica gel with water/methanol (2:1). After lyophilization, there are obtained 66 mg of amorphous (3S,4R)-3-[(Z)-2-(2-amino-4-thiazolyl)-2-(methoxyimino)acetamido]-4-ethynyl-2-oxo-1-azetidinesulphonic acid triethylamine salt.

IR (KBr, $cm^{-1}$): 3440, 1771, 1672, 1601, 1531, 1282, 1253, 1055.

NMR (CDCl$_3$, ppm): 9.50 (d, J: 8 Hz; 1H); 7.18 (s, 2H); 6.80 (s, 1H); 5.22 (dd, J=5.5 and 8 Hz; 1H), 4.61 (dd, J=2 and 5.5 Hz, 1H) 3.82 (s, 3H) 3.45 (d, J=2 Hz, 1H).

The (3S,4R)-3-amino-4-ethynyl-2-oxo-1-azetidinesulphonic acid used as the starting material can be prepared as follows:

(b) 30.1 g (0.306 mol) of trimethylsilylacetylene are dissolved in 300 ml of dry tetrahydrofuran. 290 ml of 1.05N ethylmagnesium bromide solution in tetrahydrofuran are added dropwise at 20° C. within 30 minutes while cooling with ice. The solution is stirred at 20° C. for 2 hours and subsequently added dropwise at −70° C. to −40° C. to 31.3 g (0.077 mol) of (3R,4R)-4-methylsulphonyl-3-tritylamino-2-azetidinone in 200 ml of dry tetrahydrofuran. The solution is stirred at −30° C. for 30 minutes and subsequently at 20° C. for 60 minutes and then diluted with ether. The ether phase is washed with saturated aqueous ammonium chloride solution and subsequently with water, dried and evaporated. The residue is chromatographed on 1.5 kg of silica gel with t-butyl methyl ether/n-hexane (2:3). After a forerun of 4 l, there are obtained 1 l of eluate containing substance A and subsequently 4 l of eluate containing substance B. The fractions are evaporated.

Substance A: 10.3 g (32%) of (3S,4R)-3-tritylamino-4-[2-(trimethylsilyl)ethynyl]-2-azetidinone.

NMR (CDCl$_3$, ppm): 0.08 (s, 9H), 3.23 (d, J=10 Hz, 1H), 3.59 (d, J=5 Hz, 1H), 4.30 (dd, J=5 and 10 Hz, 1H), 5.88 (1H), 7.2–7.6 (15H).

Substance B: 15.3 g (47%) of (3S,4S)-3-tritylamino-4-[2-(trimethylsilyl)ethynyl]-2-azetidinone.

NMR (CDCl$_3$, ppm): 0.10 (s, 9H), 2.8 (1H), 3.40 (d, J=2 Hz, 1H), 4.23 (1H), 5.86 (1H), 7.1–7.5 (15H).

(c) 10.0 g (0.024 mol) of (3S,4S)-3-tritylamino-4-[2-(trimethylsilyl)ethynyl]-2-acetidinone and 1.5 g (0.026 mol) of potassium fluoride are stirred at 20° C. for 1.5 hours in 100 ml of ethanol and 100 ml of dimethyl sulphoxide. The solution is diluted with ether, the ether phase is washed with water, dried and evaporated. 8.1 g (85%) of crude (3S,4S)-4-ethynyl-3-tritylamino-2-azetidinone are obtained.

NMR (CDCl$_3$, ppm): 1.8 (1H), 2.16 (d, J=2 Hz, 1H), 3.33 (tr, J=2 Hz, 1H), 4.30 (1H), 5.87 (1H), 7.2–7.5 (15H).

IR (KBr, $cm^{-1}$): 706, 751, 1490, 1599, 1625, 1769, 2.24, 3306.

In an analogous manner, from 9.4 g of (3S,4R)-3-tritylamino-4-[2-(trimethylsilyl)ethynyl]-2-azetidinone there are obtained 8.8 g (91%) of (3S,4R)-4-ethynyl-3-tritylamino-2-azetidinone.

NMR (CDCl$_3$, ppm): 2.35 (d, J=2 Hz, 1H), 3.09 (d, J=10.5 Hz, 1H), 3.58 (dd, J=2 and 5 Hz, 1H), 4.38 (dd, J=5 and 10.5 Hz, 1H), 5.88 (1H), 7.1–7.6 (15H).

IR (KBr, $cm^{-1}$): 705, 732, 1490, 1728, 1770, 2122, 3298.

(d) 3.5 g (10 mmol) of (3S,4R)-4-ethynyl-3-tritylamino-2-azetidinone and 4.0 g (25 mmol) of sulphur trioxide pyridinium complex are stirred at 80° C. for 15 minutes in 40 ml of pyridine. The solution is treated with 200 ml of ether and the resulting precipitate is dissolved in 100 ml of methylene chloride. After the addition of 5 ml of concentrated formic acid, there is obtained an oily precipitate which, after decanting off the solvent and adding ether, changes into white crystals. 1.19 g (58%) of (3S,4R)-3-amino-4-ethynyl-2-oxo-1-azetidinesulphonic acid are isolated.

NMR (DMSO, ppm): 3.75 (d, J=1.5 Hz, 1H), 4.7 (2H, 7–8 (3H).

IR (KBr, $cm^{-1}$): 1197, 1255, 1504, 1525, 1607, 1788, 2130, 3268, 3514.

Elemental analysis: Calculated: C 31.58, H 3.18, N 14.73, S 16.86%. Found: C 32.33, H 3.40, N 13.42, S 16.24 H$_2$O 1.46%.

(e) 530 mg (1.5 mmol) of (3S,4S)-4-ethynyl-3-tritylamino-2-azetidinone and 600 mg (3.75 mmol) of sulphur trioxide-pyridinium complex are stirred at room temperature for 21 hours in 6 ml of dry dioxan. The insoluble residue is filtered off under suction and the filtrate is treated with 30 ml of ether. The product is obtained as a gum-like precipitate which, after decanting off the solvent and scratching in the presence of a small amount of ether, changes into crystals. These crystals are filtered off under suction and correspond to 481 mg of (3S,4S)-4-ethynyl-2-oxo-3-tritylamino-1-azetidinesulphonic acid pyridinium salt. This product is dissolved in 20 ml of methanol, the solution is held at room temperature for 4 days, subsequently evaporated and the residue is filtered off under suction with a small amount of methanol. 180 mg (63%) of (3S,4S)-3-amino-4-ethynyl-2-oxo-1-azetidinesulphonic acid are obtained.

NMR (DMSO, ppm): 3.63 (d, J=2 Hz, 1H), 4.38 (tr, J=2 Hz, 1H), 4.46 (d, J=2 Hz, 1H).

IR (KBr, $cm^{-1}$): 1256, 1621, 2125, 2654, 3217.

EXAMPLE 5

(a) 60 mg (0.31 mmol) of (3S,4R)-3-amino-2-oxo-4-vinyl-1-azetidinesulphonic acid, 120 mg (0.34 mmol) of 2-(2-amino-4-thiazolyl)-2-(Z)-methoxyimino-acetic acid 2-benzthiazolyl thioester and 63 mg (0.62 mmol) of triethylamine are stirred at room temperature for 3 hours in 1.5 ml of acetone/water (4:1). The mixture is evaporated and the residue is chromatographed over reverse-phase silica gel using acetonitrile as the eluting agent. After evaporation, there are obtained 63 mg of (3S,4R)-3-[(Z)-2-(2-amino-4-thiazolyl)-2-(methoxyimino)acetamido]-2-oxo-4-vinyl-1-azetidinesulphonic acid triethylamine salt as an amorphous colourless powder.

IR (KBr, cm$^{-1}$): 3400, 1765, 1671, 1536, 1275, 1044.

NMR (DMSO, ppm): 9.2 (d, J=9 Hz, 1H), 7.18 (s, br, 2H); 6.64 (s, 1H), ca. 5.75 (m, 1H); ca. 5.2 (m, 3H) 4.4 (dd, J=6 and 8 Hz, 1H), 3.80 (s, 3H), 3.08 (q, J=Hz, 6H), 1.17 (t, J=7 Hz, 9H).

The foregoing triethylamine salt is dissolved in 6 ml of water and stirred for 3 hours with 5 ml of Amberlite CG 120 (Na$^+$ form). After filtration, the product is lyophilized to give 26 mg of (3S,4R)-3-[2-(2-amino-4-thiazolyl)-2-(methoxyimino)acetamido]-2-oxo-4-vinyl-1-azetidinesulphonic acid sodium salt.

NMR (DMSO, ppm): 9.22 (d, J=9 Hz, 1H); 7.21 (s, 2H); 6.64 (s, 1H); 5.84 (m, 1H), 5.38 (m, 1H), 5.18 (m, 2H) 4.40 (m, 1H), 3.80 (s, 3H).

The (3S,4R)-3-amino-2-oxo-4-vinyl-1-azetidinesulphonic acid used as the starting material can be prepared as follows:

(b) 1.55 g (4.4 mmol) of (3S,4R)-4-ethynyl-3-tritylamino-2-azetidinone are dissolved in 200 ml of methanol and the solution is hydrogenated for 2 minutes over 5% palladium/calcium carbonate catalyst (deactivated with lead). The catalyst is filtered off under suction, the filtrate is evaporated and the residue is chromatographed over 200 g of silica gel with ether/petroleum ether (2:1). After a forerun of 1.5 l, there are obtained 210 ml of eluate containing 0.50 g of (3S,4R)-3-tritylamino-4-vinyl-2-azetidinone. The next 1.4 l of eluate contain 0.80 g of a mixture of (3S,4R)-3-tritylamino-4-vinyl-2-azetidinone and (3S,4R)-4-ethyl-3-tritylamino-2-azetidinone. This mixture is chromatographed on silica gel impregnated with 30 g of silver nitrate. 0.10 g of (3S,4R)-4-ethyl-3-tritylamino-2-azetidinone is eluted with 400 ml of ether and 0.53 g of (3S,4R)-3-tritylamino-4-vinyl-2-azetidinone is eluted with 700 ml of ethyl acetate and 500 ml of acetone. The total yield is 66% of (3S,4R)-3-tritylamino-4-vinyl-2-acetidinone.

NMR (CDCl$_3$, ppm): 2.58 (d, J=ca. 10 Hz, 1H), 3.71 (d, tr, J=5 Hz and 1 Hz, 1H), 4.35–4.83 (2H), 4.95–5.25 (2H), 5.75 (1H), 7.2–7.6 (15H).

IR (KBr, cm$^{-1}$): 705, 747, 272, 900, 923, 1000, 1489, 1595, 1638, 1764, 3261.

(c) 470 mg (1.33 mmol) of (3S,4R)-3-tritylamino-4-vinyl-2-azetidinone are sulphonated with sulphur trioxidepyridinium complex and subsequently detritylated with formic acid in a manner analagous to that described in Example 4(d). 63 mg (25%) of (3S,4R)-3-amino-2-oxo-4-vinyl-1-azetidinesulphonic acid are obtained.

NMR (DMSO, ppm): 4.44 (tr, H=6.5 Hz, 1H), 4.57 (d, J=6.5 Hz, 1H), 5.39 (dd, J=2 and 10 Hz, 1H), 5.54 (dd, J=2 and 17 Hz, 1H), 5.74–6.13 (m, 1H), 8.51–9 (m, 3H).

IR (KBr, cm$^{-1}$): 951, 994, 1200, 1229, 1254, 1529, 1770, 2640.

EXAMPLE 6

In the same manner as described in Example 5, from 110 mg of (3S,4S)-3-amino-4-ethynyl-2-oxo-1-azetidinesulphonic acid there are obtained 58 mg of (3S,4S)-3-[(Z)-2-(2-amino-4-thiazolyl)-2-(methoxyimino)acetamido]-4-ethynyl-2-oxo-1-azetidinesulphonic acid triethylamine salt.

Elemental analysis for $C_{17}H_{26}N_6O_6S_2$ (474.55): Calculated: C 43.03, H 5.52, N 17.71%. Found: C 42.54, H 5.47, N 17.48%.

IR (KBr, cm$^{-1}$): 3265, 2125, 1776, 1672, 1619, 1535, 1275, 1245, 1046.

NMR (DMSO, ppm): 9.41 (d, J=8 Hz, 1H); 7.21 (s, 2H); 6.73 (s, 1H), 4.72 (dd, J=3 and 8 Hz 1H), 4.21 (dd, J=2 and 3 Hz, 1H), 3.82 (s, 3H), 3.52 (d, J=2 Hz, 1H); 3.09 (q, 7.5 Hz, 6H); 1.17 (t, 7.5 Hz, 9H).

EXAMPLE 7

(a) In the same manner as described in Example 5, from (3S,4R)-3-amino-4-ethyl-2-oxo-1-azetidinesulphonic acid there is obtained sodium (3S,4R)-3-[(Z)-2-(2-amino-4-thiazolyl)-2-(methoxyimino)acetamido]-4-ethyl-2-oxo-1-azetidinesulphonate.

NMR (DMSO, ppm): 9.27 (d, J=9 Hz, 1H), 7.20 (s, 2H), 6.70 (s, 1H), 5.08 (dd, J=6 and 9 Hz, 1H), 3.80 (s, 3H), 3.74 (m, 1H), 1.87 (m, 1H), 1.54 (m, 1H), 0.83 (t, J=6.5 Hz, 3H).

The (3S,4R)-3-amino-4-ethyl-2-oxo-1-azetidinesulphonic acid used as the starting material can be prepared as follows:

(b) 2.0 g (5.7 mmol) of (3S,4R)-4-ethynyl-3-tritylamino-2-azetidinone are dissolved in 250 ml of methanol and the solution is hydrogenated for 15 minutes over 2.0 g of 5% palladium/carbon. The catalyst is filtered off and the filtrate is evaporated. The residue corresponds to 1.4 g (69%) of (3S,4R)-4-ethyl-3-tritylamino-2-acetidinone.

NMR (CDCl$_3$, ppm): 0.65–1.25 (5H), 2.61 (d, J=8 Hz, 1H), 3.08 (1H), 4.38 (dd, J=5 and 8 Hz, 1H), 5.89 (1H), 7.1–7.6 (15H).

IR (KBr, cm$^{-1}$): 703, 755, 1491, 1596, 1752, 3266.

(c) (3S,4R)-4-Ethyl-3-tritylamino-2-azetidinone is converted in a manner analogous to that described in Example 4 into (3S,4R)-3-amino-4-ethyl-2-oxo-1-azetidinesulphonic acid which is reacted directly as the crude product.

EXAMPLE 8

(a) In the same manner as described in Example 5, from 80 mg of (3S,4S)-3-amino-2-oxo-4-vinyl-1-azetidinesulphonic acid there are obtained 88 mg of (3S,4S)-3-[(Z)-2-(2-amino-4-thiazolyl)-2-(methoxyimino)acetamido[-2-oxo-4-vinyl-1-azetidinesulphonic acid triethylamine salt as an amorphous lyophilizate.

Elemental analysis for $C_{17}H_{28}N_6O_6S_2$ (476.57): Calculated: C 42.85, H 5.92, N 17.63%. Found: C 42.38, H 5.82, N 17.41%.

IR (KBr, cm$^{-1}$): 3406, 3318, 3211, 1767, 1670, 1621, 1536, 1271, 1237, 1044.

NMR (DMSO, ppm): 10.33 (d, H=8 Hz, 1H), 7.19 (s, br, 2H), 6.70 (s, 1H), 6.03 (ddd, J=17,10 and 7 Hz 1H), 5.37 (dd, J=1.5 and 17 Hz, 1H), 5.17 (dd, J=1.5 and 10 Hz, 1H), 4.56 (dd, J=3 and 8 Hz, 1H), 4.11 (dd J=3 and 7 Hz, 1H), 3.82 (s, 3H), 3.10 (m, 6H), 1.18 (t, J=7 Hz, 9H).

The (3S,4S)-3-amino-2-oxo-4-vinyl-1-azetidinesulphonic acid used as the starting material can be prepared as follows:

(b) 2.5 g (7.1 mmol) of (3S,4S)-4-ethynyl-3-tritylamino-2-azetidinone are dissolved in 250 ml of methanol and the mixture is hydrogenated for 10 minutes over 1.5 g of 5% palladium/calcium carbonate catalyst (deactivated with lead). The catalyst is filtered off, the filtrate is evaporated and the residue is chromatographed over 200 g of silica gel with N-hexane/t-butyl methyl ether (1:2). 1.86 g (74%) of (3S,4S)-3-tritylamino-4-vinyl-2-acetidinone are obtained from the fraction 600 ml to 900 ml of eluate.

NMR (CDCl$_3$, ppm): 2.8 (1H), 3.40 (1H), 3.76 (1H), 4.78 (d, J=2 Hz, 3H), 5.78 (s, 1H), 7.2–7.6 (15H).

IR (KBr, cm$^{-1}$): 704, 748, 922, 1489, 1595, 1638, 1756, 3316.

(c) 1.0 g (2.82 mmol) of (3S,4S)-3-tritylamino-4-vinyl-2-azetidinone is sulphonated with sulphur trioxide pyridinium complex and detritylated with methanol in a manner analogous to that described in Example 4(d). 87 mg (16%) of (3S,4S)-3-amino-2-oxo-4-vinyl-1-azetidinesulphonic acid are isolated.

NMR (DMSO, ppm): 4.14–4.29 (2H), 5.27 (dd, J=2 and 10 Hz, 1H), 5.44 (dd, J=2 and 17 Hz, 1H), 5.79–6.20 (1H), 8–9 (br, 3H).

IR (KBr, cm$^{-1}$): 924, 981, 1272, 1307, 1513, 1596, 1763, 2604, 2679, 3092.

EXAMPLE 9

In the same manner as described in Example 5, from 70 mg of (3S,4S)-3-amino-4-ethyl-2-oxo-1-azetidinesulphonic acid there are obtained 152 mg of (3S,4S)-3-[(Z)-2-(2-amino-4-thiazolyl)-2-(methoxyimino)acetamido]-4-ethyl-2-oxo-1-azetidinesulphonic acid triethylamine salt as an amorphous lyophilizate.

IR (KBr, cm$^{-1}$): 3403, 3316, 3206, 1763, 1667, 1621, 1537, 1243, 1044.

NMR (DMSO, ppm): 9.27 (d, J=8.5 Hz, 1H), 7.18 (s, br 2H), 6.66 (s, 1H), 4.52 (dd, J=2.5 and 8.5 Hz, 1H), ca. 3.5 (m, 1H), 3.82 (s, 3H), 3.09 (q, J=7.5 Hz, 6H), ca. 1.8 br, 2H), 1.17 (t, J=7.5 Hz, 9H), 0.89 (tr, J=8 Hz, 3H).

The (3S,4S)-3-amino-4-ethyl-2-oxo-1-azetidinesulphonic acid used as the starting material can be prepared as follows:

(b) 2.5 g (7.1 mmol) of (3S,4S)-4-ethynyl-3-tritylamino-2-azetidinone are hydrogenated for 10 minutes over 2.5 g of 5% palladium/carbon, the catalyst is filtered off, the filtrate is evaporated and the residue is chromatographed over 200 g of silica gel with t-butyl methyl ether/n-hexane (1:1). After a forerun of 750 ml, there are isolated with 1 l of eluant 1.63 g (65%) of (3S,4S)-4-ethyl-3-tritylamino-2-azetidinone.

NMR (CDCl$_3$, ppm): 0.53–0.58 (5H), 2.7 (1H), 2.9 (1H), 3.75 (1H), 6.0 (1H), 7.2–7.6 (15H).

IR (KBr, cm$^{-1}$): 705, 747, 1490, 1596, 1753, 3260.

0.94 g (2.64 mmol) of (3S,4S)-4-ethyl-3-tritylamino-2-azetidinone are reacted in a manner analogous to that described in Example 4(d). 176 mg (34%) of (3S,4S)-3-amino-4-ethyl-2-oxo-1-azetidinesulphonic acid are obtained.

NMR (DMSO, ppm): 0.91 (tr, J=7.5 Hz, 3H), 1.44–2.1 (2H), 3.60–3.78 (1H), 4.07 (d, J=2.5 Hz, 1H), 8.69 (3H).

IR (KBr, cm$^{-1}$): 1206, 1268, 1512, 1599, 1760, 3092.

EXAMPLE 10

In a manner analogous to that described in Example 5 there can also be obtained (3S,4R)-3-[(Z)-2-(2-amino-4-thiazolyl)-2-(methoxyimino)acetamido]-2-oxo-4-propyl-1-azetidinesulphonic acid sodium salt.

Elemental analysis for C$_{12}$H$_{16}$N$_5$O$_6$S$_2$Na: Calculated: C 34.87, H 3.90, N 16.94%. Found: C 34.54, H 3.91, N 16.43%.

IR (KBr, cm$^{-1}$): 3423, 3281, 3219, 1762, 1656, 1236.

NMR (DMSO, ppm): 0.9 (3H, t, CH$_3$), 1.10–1.95 (4H, m, —CH$_2$—CH$_2$—), 3.85 (3H, s, OCH$_3$), 3.85 (1H, dt, —CH—CH$_2$—CH$_2$CH$_3$), 5.05 (1H, dd, 6 and 9 Hz, NH—CH) 6.73 (1H, s, S—CH=), 7.15 (2H, s, NH$_2$), 9.25 (1H, d, 9 Hz, CONH)—.

EXAMPLE 11

(a) In the same manner as described in Example 1, from 224 mg of rac,cis-3-amino-4-methoxycarbonyl-2-oxo-1-azetidinesulphonic acid and 367 mg of 2-(2-amino-4-oxazolyl)-2-methoxyimino-acetic acid 2-benzthiazolyl thioester (7:2 mixture of the Z:E isomers) there are obtained 259 mg of rac,cis-3-[2-(2-amino-4-isoxazolyl)-2-(methoxyimino)acetamido[-4-(methoxycarbonyl)-2-oxo-1-azetidinesulphonic acid triethylamine salt as an amorphous lyophilizate (7:2mixture of the Z:E isomers).

IR (KBr, cm$^{-1}$): 3410, 3333, 3288, 3223, 1758, 1658, 1559, 1539, 1285, 1237, 1048.

NMR (DMSO, ppm): 9.41 (d, J=8 Hz, 1H), 7.37 (s, 1H), 6.83 (s, br, 2H), 5.34 (dd, J=5.5 and 8 Hz, 1H), 4.44 (d, J=5.5 Hz, 1H), 3.77 (s, 3H), 3.58 (s, 3H), 3.06 (q, J=7.3 Hz, 6H), 1.16 (t, J=7.3 Hz, 9H).

The 2-(2-amino-4-oxazolyl)-2-methoxyimino-acetic acid 2-benzthiazolyl thioester used as the starting material can be prepared as follows:

(b) A solution of 50.4 g (0.2 mol) of ethyl 2-methoxyimino-4-bromoacetoacetate [M. Ochiai et al., Chem. Pharm. Bull. 25, 3115 (1977)] and 60.1 g (1 mol) of urea in 200 ml of dimethylformamide is heated to 100° C. for 30 minutes. Thereafter, the mixture is evaporated, the residue is taken up in 800 ml of water, neutralized with sodium bicarbonate and extracted with ethyl acetate. The ethyl acetate extract is chromatographed on silica gel with acetonitrile/methylene chloride (1:1). There is obtained ethyl 2-(2-amino-4-oxazolyl)-2-methoxyiminoacetate in a yield of 26%; melting point 120° C. (decomposition).

NMR (DMSO, ppm): 7.77 (s, 1H), 6.93 (s, 2H), 4.15 (q, J=7 Hz, 2H), 3.90 (s, 3H), 1.28 (tr, J=7 Hz, 3H).

(c) 2.13 g (10 mmol) of ethyl 2-(2-amino-4-oxazolyl)-2-methoxyimino-acetate are treated at −20° C. in 20 ml of methanol with 10 ml of 1N aqueous sodium hydroxide solution. After the addition of 10 ml of 1N aqueous hydrochloric acid, 2-(2-amino-4-oxazolyl)-2-methoxyimino-acetic acid precipitates in a yield of 54%; melting point 190° C. (decomposition).

Elemental analysis for C₆H₇N₃O₄: Calculated: C 38.93, H 3.81, N 22.70%. Found: C 38.40, H 4.01, N 22.33%.

(d) 670 mg (4.05 mmol) of triethyl phosphite are added while cooling with ice to a solution of 560 mg (3 mmol) of 2-(2-amino-4-oxazolyl)-2-methoxyimino-acetic acid, 1.2 g (3.6 mmol) of 2,2-dithio-bis-benzthiazole and 360 mg (3.6 mmol) of N-methylmorpholine in 20 ml of absolute acetonitrile. The mixture is stirred at room temperature for 3 hours. The precipitated product is then filtered off under suction, washed with water and dried. There is obtained 2-(2-amino-4-oxazolyl)-2-methoxyimino-acetic acid 2-benzthiazolyl thioester (7:2 mixture of the Z:E isomers) in a yield of 55%; melting point 139° C. (decomposition).

NMR (DMSO, ppm): 4.0 and 4.22 (s, 3H; Z+E-isomer); 6.90 and 7.08 (s, br, 2H; (E÷Z); 7.5–8.5 (m, 5H).

EXAMPLE 12

In a manner analogous to that described in Example 1, from 95 mg of (3S,4R)-3-amino-4-ethynyl-2-oxo-1-azetidinesulphonic acid there are obtained 192 mg of (3S,4R)-3-[2-(2-amino-4-oxazolyl)-2-(methoxyimino)acetamido]-4-ethynyl-2-oxo-1-azetidinesulphonic acid triethylamine salt. The product is a 5:1 mixture of the Z:E-isomers.

IR (KBr, cm⁻¹): 3339, 3263, 2683, 1773, 1659, 1541, 1277, 1254, 1045.

NMR (DMSO, ppm): 9.48÷9.67 (d, J=8.5, 1H; Z÷E); 8.07÷7.49 (s, 1H; E÷Z); 6.97÷6.82 (s, br, 2H; E÷Z); 5.2 (dd, J=6 and 8.5 Hz, 1H); 4.60 (dd, J=2 and 6 Hz, 1H); 4.01÷3.82 (s, 3H; E÷Z); 3.47 (d, J=2 Hz, 1H); 3.06 (q, J=7.5 Hz, 6H); 1.17 (t, J=7.5 Hz, 9H).

EXAMPLE 13

291 mg (1.3 mmol) of rac-cis-3-amino-4-methoxycarbonyl-2-oxo-1-azetidinesulphonic acid, 640 mg (1.8 mmol) of 2-[(5-amino-3-(1,2,4-thiadiazolyl)]-2-(Z)-methoxyimino-acetic acid 1-benzthiazolyl thioester and 263 mg of triethylamine are stirred at room temperature for 30 hours in 6 ml of dichloromethane. After evaporation of the solvent, the residue is taken up in 20 ml of water, washed five times with 10 ml of ether each time and lyophilized. 610 mg of rac-cis-3-[(Z)-2-(5-amino-1,2,4-thiadiazol-3-yl)-2-(methoxyimino)acetamido]-4-(methoxycarbonyl)-2-oxo-1-azetidinesulphonic acid triethylamine salt are obtained.

IR (KBr, cm⁻¹): 3397, 3305, 3204, 1755, 1688, 1622, 1530, 1281, 1235, 1207, 1047.

NMR (DMSO, ppm): 9.37 (d, J=8.5 Hz, 1H), 8.10 (s, br, 2H), 5.37 (dd, J=5.5 and 8.5 Hz, 1H), 4.41 (d, J=5.5 Hz, 1H) 3.86 (s, 3H), 3.61 (s, 3H), 3.04 (q, J=7.2 Hz, 6H), 1.16 (t, J=7.2 Hz, 9H).

EXAMPLE 14

(a) 190 mg (1 mmol) of (3S,4R)-3-amino-4-ethynyl-2-oxo-1-azetidinesulphonic acid, 526 mg (1.1 mmol) of 2-(2-amino-4-thiazolyl)-2-[[(Z)-1-(t-butoxycarbonyl)-1-methylethoxy]imino]-acetic acid 2-benzthiazolyl thioester and 0.280 ml (2 mmol) of triethylamine are stirred at room temperature for 20 hours in 5 ml of acetone/water (4:1). Thereupon, the mixture is concentrated, the residue is taken up in 4 ml of methanol and filtered. The filtrate is chromatographed over reverse-phase silica gel using water/methanol (10:1). After lyophilization there are obtained 213 mg of (3S,4R)-3-[(Z)-2-(2-amino-4-thiazolyl)-2-[[1-tert-butoxycarbonyl)-1-methylethoxy]imino]acetamido]-4-ethynyl-2-oxo-1-azetidinesulphonic acid as an amorphous powder.

IR (KBr, cm⁻¹): 3315, 1773, 1725, 1679, 1621, 1531, 1285, 1257, 1146, 1055.

NMR (DMSO, ppm): 9.17 (d, J=9 Hz, 1H), 7.22 (s, br, 2H), 6.77 (s, 1H), 5.26 (dd, J=6 and 9 Hz, 1H), 4.63 (dd, J=2 and 6 Hz, 1H), 3.40 (d, J=2 Hz, 1H), 1.38 (s, 15H).

The 2-(2-amino-4-thiazolyl)-2-[[(Z)-1-(t-butoxycarbonyl)-1-methylethoxy]imino]-acetic acid 2-benzthiazolyl thioester used as the starting material can be prepared as follows:

(b) 43 g (200 mmol) of ethyl 2-(2-amino-4-thiazolyl)-2-(Z)-hydroxyimino-acetate are dissolved in 1.2 l of dimethylformamide. In a nitrogen atmosphere there are gradually added thereto 89.2 g (400 mmol) of t-butyl 2-bromo-2-methyl-propionate, followed by 110.6 g (800 mmol) of finely powdered potassium carbonate. The mixture is stirred at 45° C. for 12 hours. After cooling to room temperature, there are added thereto 4 l of water and the mixture is extracted with 3.5 l of ethyl acetate. The organic phase is washed three times with 2 l of water. The aqueous phase extracted with 1.5 l of ethyl acetate. The combined ethyl acetate solutions are dried over magnesium sulphate and evaporated to dryness. After recrystallization from ether, there are obtained 61.4 g (85.9%) of ethyl 2-(2-amino-4-thiazolyl)-2-[[(Z)-1-(t-butoxycarbonyl)-1-methylethoxy]imino]-acetate of melting point 172° C.

(c) 240 g (671.5 mmol) of ethyl 2-(2-amino-4-thiazolyl)-2-[[(Z)-1-(t-butoxycarbonyl)-1-methyl-ethoxy]imino]-acetate are stirred at 50° C. for 12 hours in 1.3 l of methanol and 1.34 l of 1N aqueous sodium hydroxide solution. The methanol is removed by evaporation and the aqueous phase is washed twice with 1 l of ethyl acetate. The product crystallizes out after the addition of 1.34 l of 1N aqueous hydrochloric acid. After cooling to 0° C., the crystals are filtered off, washed successively with water, acetonitrile and ether and dried at 40° C. under reduced pressure. The thus-obtained product crystallizes with 12% water and is stirred in acetonitrile for 2 hours in order to remove the water. After filtration and drying under reduced pressure at 40° C., there are obtained 177.7 g (80.3%) of 2-(2-amino-4-thiazolyl)-2-[[(Z)-1-(t-butoxycarbonyl)-1-methylethoxy]imino]-acetic acid of melting point 178°–179° C. The water content is 0.4%.

(d) 28.8 g (86.4 mmol) of 2-(2-amino-4-thiazolyl)-2-[[(Z)-1-(t-butoxycarbonyl)-1-methylethoxy]imino]-acetic acid are dispersed in 360 ml of acetonitrile. 14.4 ml (130.5 mmol) of N-methylmorpholine are added thereto while stirring. After 10 minutes, 34.6 g (103.5 mmol) of 2,2-dithio-bis-benzthiazole are added thereto and the suspension obtained is cooled to 0° C. After the addition of 20.2 ml (117 mmol) of triethyl phosphite (slow addition within 2 hours), the suspension is stirred at 0° C. for 12 hours. The product is filtered off, washed successively with cold acetonitrile, isopropyl ether and petroleum ether and dried at room temperature under reduced pressure. There are obtained 33.7 g (81.5%) of 2-(2-amino-4-thiazolyl)-2-[[(Z)-1-(t-butoxycarbonyl)-1-methylethoxy]imino-acetic acid 2-benzthiazolyl thioester of melting point 139°–140° C.

EXAMPLE 15

66 mg of (3S,4R)-3-[2-(2-amino-4-thiazolyl)-2-[[(Z)-1-(tert-butoxycarbonyl)-1-methylethoxy]imino]acetamido]-4-ethynyl-2-oxo-1-azetidinesulphonic acid are added at −10° C. to 4 ml of trifluoroacetic acid. After 4 hours, the mixture is evaporated, the residue is taken up with a small amount of water and chromatographed over MCI gel using water. After lyophilization, there are obtained 10 mg of amorphous (3S,4R)-3-[2-(2-amino-4-thiazolyl)-2-[(Z)-(1-carboxy-1-methylethoxy)imino]acetamido]-4-ethynyl-2-oxo-1-azetidinesulphonic acid.

IR (KBr, cm$^{-1}$): 3292, 1771, 1679, 1638, 1531, 1276, 1047.

NMR (DMSO, ppm): 9.38 (d, J=8.5 Hz, 1H,), 6.90 (s, 1H), 5.28 (dd, J=5.5 and 8.5 Hz, 1H), 4.67 (dd, J=2 and 5.5 Hz, 1H), 3.44 (d, J=2 Hz, 1H), 1.36 (s, br, 6H).

EXAMPLE 16

In a manner analogous to that described in Example 14, there is obtained sodium (3S,4R)-3-[(Z)-2-(2-amino-4-thiazolyl)-2-[(1-carboxy-1-methylethoxy)imino]acetamido]-4-methyl-2-oxo-1-azetidinesulphonate.

IR (KBr, cm$^{-1}$): 3297, 2984, 2683, 1763, 1675, 1631, 1535, 1276.

NMR (DMSO, ppm): 1.1 and 1.20 (6H, 2s, 2×CH$_3$) 1.45 (3H, d, 3.5 Hz, CH—CH$_3$), 4.0 (1H, m, CH—CH$_3$), 5.05 (1H, dd, 6 and 9 Hz, NH—CH), 6.75 (1H, s, S—CH=), 7.20 (3H, broad NH$_3$), 9.15 (1H, d, 9 Hz, CONH).

EXAMPLE 17

106 mg (0.55 mmol) of (3S, 4S)-3-amino-4-ethyl-2-oxo-1-azetidinesulphonic acid, 288 mg (0.6 mmol) of 2-(2-amino-4-thiazolyl)-2-[[(Z)-1-(t-butoxycarbonyl)-1-methylethoxy]imino]-acetic acid 2-benzthiazolyl thioester and 0.153 ml of triethylamine (1.1 mmol) are stirred at room temperature for 3 hours in 3 ml of acetone/water (4:1). The mixture is evaporated, the residue is taken up in 10 ml of water, washed three times with 20 ml of ether each time and lyophilized. 270 mg of (3S, 4S)-3-[(Z)-2-(2-amino-4-thiazolyl)-2-[[1-(t-butoxycarbonyl)-1-methylethoxy]imino]acetamido]-4-ethyl-2-oxo-1-azetidinesulphonic acid triethylamine salt are obtained.

Elemental analysis for C$_{24}$H$_{42}$N$_6$O$_8$S$_2$ (606.75): Calculated: C 47.51, H 6.98, N 13.85%. Found: C 47.29, H 6.96, N 13.68%.

EXAMPLE 18

250 mg of (3S, 4S)-3-[(Z)-2-(2-amino-4-thiazolyl)-2-[[1-(t-butoxycarbonyl)-1-methylethoxy]imino]acetamido]-4-ethyl-2-oxo-1-azetidinesulphonic acid triethylamine salt are added at −10° C. to 3 ml of trifluoroacetic acid. After 20 hours at −10° C., the mixture is evaporated and the residue is purified by DCCC [droplet counter current chromatography; rising droplets in the mixture chloroform/methanol/water (7:13:8)]. 58 mg of amorphous (3S, 4S)-3-[(Z)-2-(2-amino-4-thiazolyl)-2-[(1-carboxy-1-methylethoxy)imino]acetamido]-4-ethyl-2-oxo-1-azetidinesulphonic acid triethylamine salt are obtained.

IR (KBr, cm$^{-1}$): 1766, 1673, 1539, 1201, 1042.

NMR (DMSO, ppm): 9.13 (d, J=9 Hz, 1H); 6.66 (s, 1H); 4.58 (dd, J=2.5 and 9 Hz); 3.58 (m, 1H); 3.10 ( , J=7 Hz, 6H); 1.42 (s, br, 6H); 1.19 (t, J=7 Hz, 9H); 0.89 (tr, J=7 Hz, 3H).

EXAMPLE 19

224 mg (1 mmol) of rac-cis-3-amino-4-methoxycarbonyl-2-oxo-1-azetidinesulphonic acid, 526 mg (1.1 mmol) of (Z)-2-(2-amino-4-thiazolyl)-2-[[1-(t-butoxycarbonyl)-1-methylethoxy]imino]-acetic acid 2-benzthiazolyl thioester and 281 mg of triethylamine are stirred at room temperature for 4 hours in 5 ml of dichloromethane. After evaporation of the solvent, the residue is taken up in 20 ml of water, washed five times with 20 ml of ether each time and lyophilized. 569 mg of rac-cis-3-[(Z)-2-(2-amino-4-thiazolyl)-2-[[1-(t-butoxycarbonyl)-1-methylethoxy]imino]acetamido]-4-methoxycarbonyl-2-oxo-1-azetidinesulphonic acid are obtained.

EXAMPLE 20

550 mg of rac-cis-3-[(Z)-2-(2-amino-4-thiazolyl)-2-[[1-(t-butoxycarbonyl)-1-methylethoxy]imino]acetamido]-4-methoxycarbonyl-2-oxo-1-azetidinesulphonic acid are added at room temperature to 5.5 ml of trifluoroacetic acid. After 45 minutes, the mixture is evaporated and the residue is purified by chromatography on reverse-phase silica gel using water/methanol (4:1). There are obtained 27 mg of pure rac-cis-3-[(Z)-2-(2-amino-4-thiazolyl)-2-[(1-carboxy-1-methylethoxy)imino]acetamido]-4-methoxycarbonyl-2-oxo-1-azetidinesulphonic acid as an amorphous lyophilizate.

NMR (DMSO, ppm): 9.13 (d, J=8.5 Hz, 1H); 6.67 (s, 1H); 5.44 (dd, J=6 and 8.5 Hz, 1H); 4.48 (d, J=6 Hz, 1H); 3.60 (s, 3H); 1.42 (s, br, 6H).

EXAMPLE 21

(a) 522 mg (1.0 mmol) of 2-(2-amino-4-thiazolyl)-2-[[(Z)-1-[2-(trimethylsilyl)ethoxycarbonyl]-1-methylethoxy]imino]-acetic acid 2-benzthiazolyl thioester and 224 mg (1.0 mmol) of rac-cis-3-amino-4-methoxycarbonyl-2-oxo-1-azetidinesulphonic acid are suspended in 5.0 ml of absolute acetone and the suspension is treated with 0.278 ml (2.0 mmol) of triethylamine. The clear yellow solution obtained is stirred at room temperature for 24 hours and subsequently evaporated. The residue is subjected to DCCC chromatography [droplet counter current chromatography; rising droplets in the mixture chloroform/methanol/water (7:13:8)]. The interesting fractions are combined, concentrated and lyophilized. There are obtained 211 mg (31%) of rac-cis-3-[(Z)-2-(2-amino-4-thiazolyl)-2-[[1-[[2-(trimethylsilyl- )ethoxy]carbonyl]-1-methylethoxy]imino]acetamido]-4-methoxycarbonyl-2-oxo-1-azetidinesulphonic acid triethylamine salt (1:1).

NMR (D$_2$O, ppm): 0.03 (s, 9H), 0.96 (m, 2H), 1.24 (t, J=7.3 Hz, 9H), 1.50 (s, 6H), 3.16 (q, J=7.3 Hz, 6H), 3.74 (s, 3H), 4.23 (m, 2H), 4.92 (d, J=6.0 Hz, 1H), 5.66 (d, J=6.0 Hz, 1H), 6.81 (s, 1H).

IR (KBr, cm$^{-1}$): 3434 (53%), 1783 (30%), 1740 (35%), 1685 (44%), 1624 (56%), 1537 (39%), 1283 (21%), 1250 (27%), 1153 (33%), 1047 (23%), 840 (47%).

(b) 170 mg (0.25 mmol) of rac-cis-3-[(Z)-2-(2-amino-4-thiazolyl)-2-[[1-[[2-(trimethylsilyl)ethoxy]carbonyl]-1-methylethoxy]imino]acetamido]-4-methoxycarbonyl-2-oxo-1-azetidinesulphonic acid triethylamine salt are dissolved in 10 ml of dry tetrahydrofuran and the solution is treated with 130 mg (0.50 mmol) of dry tetrabutylammonium fluoride. The mixture is stirred at room temperature overnight and subsequently evaporated. The residue is dissolved in a small amount of saturated aqueous sodium bicarbonate solution and chromatographed on Amberlite XAD-2 using water and subsequently 30% ethanol in water for the elution. After lyophilization, there are obtained 40 mg (32%) of rac-cis-3-[(Z)-2-(2-amino-4-thiazolyl)-2-[(1-carboxy-1-methylethoxy)imino]acetamido]-4-methoxycarbonyl-2-oxo-1-azetidinesulphonic acid sodium salt.

IR (KBr, cm$^{-1}$): 1771, 1730.

The 2-(2-amino-4-thiazolyl)-2-[[(Z)-1-[2-(trimethylsilyl)ethoxycarbonyl]-1-methylethoxy]imino]-acetic acid 2-benzthiazolyl thioester used as the starting material can be prepared as follows:

(c) 24.9 g (102 mmol) of t-butyl 2-(2-amino-4-thiazolyl)-2-(Z)-hydroxyimino-acetate are dissolved in 400 ml of dimethylformamide. After the addition of 54.7 g (205 mmol) of 2-(trimethylsilyl)ethyl 2-bromo-2-methylpropionate, followed by 56.6 g (410 mmol) of finely ground potassium carbonate, the mixture is stirred at 25° C. for 4 hours in a nitrogen atmosphere. After the addition of 3 l of water, the mixture is extracted with 1.5 l of ethyl acetate. The organic phase is washed twice with 1.5 l of water. The aqueous phase is extracted with 1.5 l of ethyl acetate. The combined ethyl acetate solutions are dried over sodium sulphate and evaporated to dryness. The product is purified by flash chromatography on silica gel [hexane/ethyl acetate (2:1)] and crystallized from methanol/water. There are obtained 28.6 g (65.3%) of t-butyl 2-(2-amino-4-thiazolyl)-2-[(1-(2-(trimethylsilyl)ethoxycarbonyl)-1-methylethoxy]imino]-acetate of melting point 83° C.

(d) 13.4 g (31.2 mmol) of t-butyl 2-(2-amino-4-thiazolyl)-2-[(Z)-(1-(2-(trimethylsilyl)ethoxycarbonyl)-1-methylethoxy]imino]-acetate are stirred at room temperature for 1.5 hours in 210 ml of acetic acid and 13.4 ml (104.5 mmol) of boron trifluoride etherate. The solution is poured into 650 ml of water and the pH is adjusted to 3.0 with sodium bicarbonate. The precipitated crystals are filtered off and dried at room temperature under reduced pressure. There are obtained 7.6 g (65.5%) of 2-(2-amino-4-thiazolyl)-2-[[(Z)-1-[2-trimethylsilyl)ethoxycarbonyl]-1-methylethoxy]imino]-acetic acid of melting point 155° C. (decomposition). (The compound contains 3.3% of water). After digesting the compound twice in 50 ml of dry acetonitrile and evaporation of the solvent, the water content after drying at room temperature (16 hours under reduced pressure -0.1 mm Torr) drops to 0.22%.

(e) 10.9 g (29.2 mmol) of 2-(2-amino-4-thiazolyl)-2-[[(Z)-1-[2-(trimethylsilyl)ethoxycarbonyl]-1-methylethoxy]imino]-acetic acid are dispersed in 195 ml of acetonitrile (dried with molecular sieve 3Å) and the dispersion is treated while stirring with 4.09 ml (37.1 mmol) of N-methylmorpholine, followed by 11.7 g (35 mmol) of 2,2-di-thio-bis-benzothiazole and 6.7 ml (39.7 mmol) of triethyl phosphite. After stirring at room temperature for 1 hour, the clear yellow solution obtained is evaporated to dryness. The amorphous residue is purified by flash chromatography on silica gel [hexane/ethyl acetate 4:1)] and the pure fractions are crystallized from acetonitrile. There are obtained 4.6 g (30%) of 2-(2-amino-4-thiazolyl)-2-[[(Z)-1-[2-(trimethylsilyl)ethoxycarbonyl]-1-methylethoxy]imino]-acetic acid 2-benzthiazolyl thioester of melting point 92° C. (decomposition).

EXAMPLE 22

(a) 201 mg (0.38 mmol) of 2-(2-amino-4-thiazolyl)-2-[[(Z)-(p-nitrobenzyloxycarbonyl)methoxy]imino]-acetic acid 2-benzthiazolyl thioester and 85 mg (0.38 mmol) of rac-cis-3-amino-4-methoxycarbonyl-2-oxo-1-azetidinesulphonic acid are suspended in 1.9 ml of absolute acetone and the suspension is treated with 0.11 ml (0.79 mmol) of triethylamine. The mixture is stirred at room temperature for 3 hours and then evaporated. The residue is subjected to DCCC chromatography [droplet counter current chromatography; rising droplets in the mixture chloroform/methanol/water (7:13:8)]. The interesting fractions are combined, concentrated and lyophilized. There are obtained 56 mg (21%) of rac-cis-3-[2-(2-amino-4-thiazolyl)-2-[[(Z)-(p-nitrobenzyloxycarbonyl)methoxyimino]acetamido]-4-methoxycarbonyl-2-oxo-1-azetidinesulphonic acid triethylamine salt.

NMR (D$_2$O, ppm): 1.26 (t, J=7.0 Hz, 9H), 3.18 (q, J=7.0 Hz, 6H), 3.71 (s, 3H), 4.88 (s, 2H), 4.96 (d, J=6.0 Hz, 1H), 5.31 (s, 2H), 5.64 (d, J=6.0 Hz, 1H), 6.89 (s, 1H), 7.50 (d, J=8.5 Hz, 2H), 8.07 (d, J=8.5 Hz, 2H).

IR (KBr, cm$^{-1}$): 3340 (56%), 1756 (26%), 1683 (43%), 1609 (46%), 1348 (28%), 1281 (22%), 1213 (25%), 1046 (23%).

Elemental analysis for $C_{19}H_{18}N_6O_{12}S_2+C_6H_{15}N$ (687.696): Calculated: C 43.66, H 4.84, N 14.26, S 9.32%. Found: C 43.70, H 4.80, N 14.24, S 9.30%.

The 2-(2-amino-4-thiazolyl)-2-[[(Z)-(p-nitrobenzyloxycarbonyl)methoxy]imino]-acetic acid 2-benzthiazolyl thioester used as the starting material can be prepared as follows:

(b) 6.1 g (25 mmol) of t-butyl 2-(2-amino-4-thiazolyl)-2-(Z)-hydroxyimino-acetate are dispersed in 250 ml of dry acetonitrile. 13.7 g (50 mmol) of p-nitrobenzyl bromoacetate and 12.9 ml (75 mmol) of N-ethyldiisopropylamine are now added thereto at room temperature while stirring. 7.5 g (50 mmol) of sodium iodide are added thereto 5 minutes later. The mixture is stirred at room temperature for 3.5 hours in an argon atmosphere.

The solvent is subsequently removed by evaporation and the residue is diluted with 500 ml of ethyl acetate. The solution obtained is washed four times with a total of 2 l of water. The aqueous phase is extracted with 300 ml of ethyl acetate and the combined ethyl acetate solutions are dried over sodium sulphate and evaporated to dryness. After crystallization from ethyl acetate/hexane, there are obtained 8.2 g (75%) of t-butyl 2-(2-amino-4-thiazolyl)-2-[[(p-nitrobenzyloxycarbonyl)methoxy]imino]-acetate of melting point 146.8° C. (decomposition).

(c) 5.0 g (11.4 mmol) of t-butyl 2-(2-amino-4-thiazolyl)-2-[[(Z)-(p-nitrobenzyloxycarbonyl)methoxy]imino]-acetate are stirred in 86 ml of acetic acid and treated with 5.2 ml (38.4 mmol) of boron trifluoride etherate. The solution obtained is stirred at room temperature for 5 hours and subsequently poured into 260 ml of water. The precipitate obtained is filtered off and dried at 40° C. under reduced pressure. There are obtained 3.5 g (80%) of 2-(2-amino-4-thiazolyl)-2-[[(p-nitrobenzyloxycarbonyl)methoxy]imino]-acetic acid of melting point about 175° C. (decomposition).

(d) 1.9 g (0.5 mmol) of 2-(2-amino-4-thiazolyl)-2-[[(Z)-(p-nitrobenzyloxycarbonyl)methoxy]imino]-acetic acid are dispersed in 30 ml of acetonitrile (dried with a 3Å molecular sieve). This suspension is treated while stirring with 1.4 ml (12.7 mmol) of N-methylmorpholine, followed by 2.0 g (6.0 mmol) of 2,2-dithio-bis-benzthiazole and 1.14 ml (6.7 mmol) of triethyl phosphite. After stirring at room temperature for 1 hour, the mixture is cooled to 0° C. and filtered. The filtrate is evaporated and the residue is crystallized from methylene chloride. There are obtained 1.03 g (39%) of 2-(2-amino-4-thiazolyl)-2-[[(Z)-(p-nitrobenzyloxycarbonyl)methoxy]imino]-acetic acid 2-benzthiazolyl thioester of melting point 124°-126° C.

EXAMPLE 23

343 mg (0.5 mmol) of rac-cis-3-[(Z)-2-(2-amino-4-thiazolyl)-2-[[(p-nitrobenzyloxycarbonyl)methoxy]imino]-acetamido]-4-methoxycarbonyl-2-oxo-1-azetidinesulphonic acid triethylamine salt are dissolved in 20 ml of methanol and the solution is hydrogenated at room temperature with 230 mg of 5% palladium/siliceous earth in an atmosphere of hydrogen for 3 hours. The catalyst is removed by filtration and the solution is evaporated. The residue is taken up in a small amount of saturated aqueous sodium carbonate solution and chromatographed on Amberlite XAD-2 using water and subsequently 30% ethanol in water for the elution. After lyophilization, there are obtained 120 mg (51%) of rac-cis-3-[(Z)-2-(2-amino-4-thiazolyl)-2-[(carboxymethoxy)imino]acetamido]-4-methoxycarbonyl-2-oxo-1-azetidinesulphonic acid sodium salt.

IR (KBr, cm$^{-1}$): 1775, 1730.

EXAMPLE 24

265 mg (0.5 mmol) of (Z)-2-(2-amino-4-thiazolyl)-2-[[(p-nitrobenzyloxycarbonyl)methoxy]imino]-acetic acid 2-benzthiazolyl thioester and 104 mg (0.5 mmol) of (3S,4S)-3-amino-4-carbamoyl-2-oxo-1-azetidinesulphonic acid are suspended in 2.5 ml of absolute acetone and the suspension is treated with 0.15 ml (1.1 mmol) of triethylamine. After 30 minutes, the suspension dissolves to give a yellow solution. After 24 hours at room temperature, the mixture is evaporated and the residue is subjected to DCCC chromatography [droplet counter current chromatography; rising droplets in the mixture chloroform/methanol/water (7:13:8)]. The interesting fractions are evaporated and lyophilized. There is obtained 0.139 g (41%) of (3S,4S)-3-[(Z)-2-(2-amino-4-thiazolyl)-2-[[(p-nitrobenzyloxycarbonyl)methoxy]imino]acetamido]-4-carbamoyl-2-oxo-1-azetidinesulphonic acid triethylamine salt.

NMR (D$_2$O, ppm): 1.31 (t, J=7.5 Hz, 9H) 3.24 (q, J=7.5 Hz, 6H), 4.95 (d, J=6.0 Hz, 1H) 4.95 (s, 2H), 5.34 (s, 2H), 5.69 (d, J=6.0 Hz, 1H), 6.98 (s, 1H), 7.49 (d, J=9.0 Hz, 2H), 8.16 (d, J=9.0 Hz, 2H).

IR (KBr, cm$^{-1}$): 3333 (42%), 1773 (26%), 1687 (20%), 1608 (42%), 1348 (27%), 1277 (22%), 1248 (26%), 1046 (19%).

Elemental analysis for C$_{18}$H$_{17}$N$_7$O$_{11}$S$_2$+C$_6$H$_{15}$N (672.698): Calculated: C 42.85, H 4.80, N 16.66, S 9.53, H$_2$O. Found: C 41.22, H 4.81, N 16.13, S 9.45, H$_2$O 1.84%.

EXAMPLE 25

336 mg (0.5 mmol) of (3S,4S)-3-[(Z)-2-(2-amino-4-thiazolyl)-2-[[(p-nitrobenzyloxycarbonyl)methoxy]imino]acetamido]-4-carbamoyl-2-oxo-1-azetidinesulphonic acid triethylamine salt are dissolved in 20 ml of methanol and the solution is hydrogenated at room temperature for 3-4 hours with 150 mg of 5% palladium-on-siliceous earth. The catalyst is removed by filtration and the solution is evaporated. The residue is dissolved in a small amount of saturated aqueous sodium bicarbonate solution and chromatographed on Amberlite XAD-2 using water and subsequently 40% ethanol in water for the elution. After lyophilization, there are obtained 150 mg (65%) of (3S,4S)-3-[(Z)-2-(2-amino-4-thiazolyl)-2-[(carboxymethoxy)imino]acetamido]-4-carbamoyl-2-oxo-1-azetidinesulphonic acid sodium salt.

IR (KBr, cm$^{-1}$): 3421, 1769, 1731, 1690.

EXAMPLE 26

(a) 1.62 g (6.20 mmol) of (3S,4S)-3-amino-4-carbamoyloxymethyl-2-oxo-1-azetidinesulphonic acid sodium salt are dissolved in 180 ml of acetone/water (2:1) and the solution is treated with 3.27 g (6.83 mmol) of (Z)-2-(2-amino-4-thiazolyl)-2-[[1-[t-butoxycarbonyl]-1-methylethoxy]imino]-acetic acid 2-benzthiazolyl thioester. The mixture is stirred at room temperature for 12 hours. A further 60 mg (0.12 mmol) of the aforementioned thioester are added thereto and the stirring is continued for a further 3 hours. Acetone is removed under reduced pressure and 50 ml of water are added thereto. The crystals obtained are filtered off and washed with water. The mother liquor is partially evaporated (37° C., 15 mmHg) and chromatographed (MCI gel, water). After lyophilization, there are obtained 2.28 g (77%) of (3S,4S)-3-[2-amino-4-thiazolyl)-2-(Z)-[[1-(t-butoxycarbonyl)-1-methylethoxy]imino]acetamido]-4-carbamoyloxymethyl-2-oxo-1-azetidinesulphonic acid sodium salt.

IR (KBr, cm$^{-1}$): 1766, 1723, 1683, 1617, 1531, 1458, 1369.

NMR (DMSO, ppm): 1.35 (15H, s), 4.0–4.15 (3H, H$_4$ and CH$_2$—OCONH$_2$), 5.25 (1H, dd, H$_3$), 6.5 (2H, broad, CONH$_2$), 6.7 (1H, s, H-thiazole), 7.25 (2H, s, NH$_2$), 8.9 (1H, d, CO—NH).

The (3S,4S)-3-amino-4-carbamoyloxymethyl-2-oxo-1-azetidinesulphonic acid sodium salt used as the starting material can be prepared as follows:

(b) To a solution, stirred at room temperature, of 0.9 g (5.4 mmol) of 2,4-dimethoxybenzylamine in 100 ml of methylene chloride are added 3 g of molecular sieve 4Å and, after 20 minutes, 0.7 g (5.4 mmol) of isopropylidene-L-glyceraldehyde and 5 g of anhydrous magnesium sulphate. The mixture is subsequently stirred at room temperature for 1 hour. The organic solution of isopropylidene-L-glyceraldehyde (2,4-dimethoxybenzyl)imine obtained is cooled to −20° C. under argon and treated while stirring with 0.88 ml (5.4 mmol) of triethylamine. A solution of 1.25 g (5.6 mmol) of phthaloylglycyl chloride in 20 ml of dry methylene chloride is then added dropwise within 1 hour and the mixture is subsequently stirred at room temperature overnight. The mixture is washed three times with 100 ml of water each time and with 100 ml of sodium chloride solution and then dried over sodium sulphate. The organic solution is evaporated and the residue is chromatographed on silica gel (230–400 mesh) while eluting with hexane/ethyl acetate (1:1). There are obtained 1.77 g (70%) of N-[(3S,4S)-cis-1-(2,4-dimethoxybenzyl)-4-[(R)-2,2-dimethyl-1,3-dioxolan-4-yl]-2-oxo-3-azetidinyl]phthalimide as a foam; $[\alpha]_D$=+41° (c=0.8 in chloroform); MS: 466 (M+).

(c) A solution of 149.3 g (0.32 mol) of N-[(3S,4S)-cis-1-(2,4-dimethoxybenzyl)-4-[(R)-2,2-dimethyl-1,3-dioxolan-4-yl]-2-oxo-3-azetidinyl]phthalimide in 2.5 l of methylene chloride is treated with 34 ml (0.64 mol) of methylhydrazine. The mixture is stirred at 20° C. overnight, precipitated material is filtered off and the filtrate is evaporated under reduced pressure. The residue is taken up in 1.2 l of ethyl acetate and the suspension obtained is filtered. The filtrate is washed three times with 500 l of water each time and with 500 ml of sodium chloride solution and then dried over sodium sulphate. After evaporation of the solvent, there are obtained 104.3 g (86.8%) of crude (3S,4S)-cis-3-amino-1-(2,4-dimethoxybenzyl)-4-[(R)-2,2-dimethyl-1,3-dioxolan-4-yl]-2-azetidinone which is used in the next step without further purification.

(d) A stirred solution of 104 g (3.0 mol) of (3S,4S)-3-amino-1-(2,4-dimethoxybenzyl)-4-[(R)-2,2-dimethyl-1,3-dioxolan-4-yl]-2-azetidinone and 104 ml (1.2 mol) of butylene oxide in 1.5 l of methylene chloride is treated dropwise with 57.6 ml (0.4 mol) of carbobenzoxy chloride, the mixture is stirred for 1 hour and subsequently evaporated under reduced pressure. The crude material obtained is treated with 2 l of dry ether, a crystalline material being obtained. There are obtained 122.6 g (84%) of benzyl (3S,4S)-cis-1-(2,4-dimethoxybenzyl)-4-[(R)-2,2-dimethyl-1,3-dioxolan-4-yl]-2-oxo-3-azetidinecarbamate of melting point 115°–116° C.; $[\alpha]_D$=÷48° (c=0.3 in methanol).

(e) A solution of 160 g (0.34 mol) of benzyl (3S,4S)-cis-1-(2,4-dimethoxybenzyl)-4-[(R)-2,2-dimethyl-1,3-dioxolan-4-yl]-2-oxo-2-azetidinecarbamate in 1000 ml of tetrahydrofuran and 400 ml of water is stirred at about 60° C. overnight in the presence of 8 g of p-toluenesulphonic acid. The mixture is neutralized with saturated sodium bicarbonate solution and the tetrahydrofuran is removed by evaporation. The aqueous solution is then extracted with 2 l of ethyl acetate. After drying over sodium sulphate and evaporation, there are obtained 142 g (97.2%) of pure benzyl (3S,4S)-cis-4-[(R)-1,2-dihydroxyethyl]-1-(2,4-dimethoxybenzyl)-2-oxo-3-acetidinecarbamate of melting point 177°–178° C. (from methanol).

(f) A solution of 142 g (0.33 mol) of benzyl (3S,4S)-cis-4-[(R)-1,2-dihydroxyethyl]-1-(2,4-dimethoxybenzyl)-2-oxo-3-azetidinecarbamate in 1000 ml of tetrahydrofuran is treated dropwise while stirring with a solution of 76.8 g (0.359 mol) of sodium metaperiodate in 600 ml of water. The mixture is stirred for 1 hour, filtered and the filtrate is evaporated under reduced pressure. The residue is taken up in 400 ml of ethyl acetate and washed twice with 100 ml of water each time and with 50 ml of sodium chloride solution. After drying and evaporation, there are obtained 105 g (87.8%) of pure benzyl (3S,4S)-cis-1-(2,4-dimethoxybenzyl)-4-formyl-2-oxo-3-azetidinecarbamate of melting point 145°–147° C. (from ethyl acetate/hexane); $[\alpha]_D$=÷13.7° (c=1 in chloroform).

(g) 4.27 g (113 mmol) of sodium borohydride are dissolved in 1.6 l of absolute ethanol and the solution is cooled to 0° C. This solution is treated dropwise with a solution of 90 g (226 mmol) of benzyl (3S,4S)-cis-1-(2,4-dimethoxybenzyl)-4-formyl-2-oxo-3-azetidinecarbamate in 720 ml of ethanol/tetrahydrofuran (1:1). The mixture is stirred at 0° C. for 2 hours, subsequently treated with 350 ml of saturated aqueous sodium sulphate solution and then stirred for 45 minutes. After filtration and evaporation of the solvent, the residue is taken up in 1.5 l of ethyl acetate and washed until neutral. After drying over sodium sulphate and partial evaporation, there are obtained 72.2 g (79.6%) of (3S,4S)-cis-3-benzyloxycarboxamido-1-(2,4-dimethoxybenzyl)-4-hydroxymethyl-2-azetidinone in the form of colourless crystals of melting point 138° C.; $[\alpha]_D$=÷41.6° (c=1 in methanol).

Elemental analysis for C$_{21}$H$_{24}$N$_2$O$_6$: Calculated: C 62.99, H 6.04, N 7.00%. Found: C 62.76, H 6.09, N 6.96%.

IR (KBr, cm$^{-1}$): 1718, 1698, 1615, 1589.

NMR (CDCl$_3$, ppm): 2.45 (1H, dd, OH), 3.55–3.75 (3H, broad, CH—CH$_2$—), 3.79 (6H, s, 2×OCH$_3$), 4.35 (2H, s, N—CH$_2$), 5.05 (2H, s, Φ—CH$_2$), 5.11 (1H, dd, 5 and 9 Hz, H$_3$), 6.06 (1H, d, 9 Hz NH), 6.43 (2H, m, Ar), 7.15 (1H, m, Ar), 7.31 (5H, m, C$_6$H$_5$).

MS: 292 (M-BzOH).

(h) A solution of 30 g (74.9 mmol) of (3S,4S)-cis-3-benzyloxycarboxamido-1-(2,4-dimethoxybenzyl)-4-hydroxymethyl-2-azetidinone in 600 ml of methylene chloride is treated at 0°–5° C. with 21.22 g (2 equivalents) of chlorosulphonyl-isocyanate. After 15 minutes, the mixture is added dropwise to an aqueous solution, cooled to 5° C., of 20.9 g (2.7 equivalents) of sodium sulphite. The mixture is stirred for 2 hours, subsequently diluted with methylene chloride and the organic phase is separated, washed with aqueous sodium chloride solution and dried over sodium sulphate for 12 hours. The organic phase is subsequently treated with magnesium sulphate and stirred for a further 2 hours. After filtration and evaporation of the solvent, the residue is treated with ether, the crystals obtained are filtered off and washed with ether. There are obtained 32.6 g (97%) of (3S,4S)-cis-3-benzyloxycarboxamido-4-carbamoyloxymethyl-1-(2,4-dimethoxybenzyl)-2-azetidinone of melting point 178°–179° C.; $[\alpha]_D = \div 84.7°$ (c=0.8 in chloroform).

Elemental analysis for $C_{22}H_{25}N_3O_7$: Calculated: C 59.59, H 5.68, N 9.48%. Found: C 59.17, H 5.69, N 9.37%.

IR (KBr, cm$^{-1}$): 1761, 1708, 1618, 1587.

(i) A suspension of 11.9 g (26.8 mmol) of (3S,4S)-cis-3-benzyloxycarboxamido-4-carbamoyloxymethyl-1-(2,4-dimethoxybenzyl)-2-azetidinone, 14.5 g (53.5 mmol) of potassium peroxydisulphate, 13.98 g (80.3 mmol) of dipotassium hydrogen phosphate and 1.33 g (5.36 mmol) of copper sulphate pentahydrate in 270 ml of acetonitrile and 130 ml of water is heated to 95° C. for 3.5 hours in an argon atmosphere at a pH between 6.5 and 7.0 (occasional addition of 10 g of dipotassium hydrogen sulphate). After cooling and filtration, the aqueous phase is discarded and the organic phase is evaporated. The residue is taken up in ethyl acetate and washed with water and sodium chloride solution. After drying over sodium sulphate, filtration and evaporation of the solvent, the residue is taken up in ether and filtered. The crude crystals (8.9 g) are chromatographed on silica gel [300 g, 40–63 μm, chloroform/methanol/ethyl acetate 85:10:5]. There are obtained 5.5 g (70%) of (3S,4S)-cis-3-benzyloxycarboxamido-4-carbamoyloxymethyl-2-azetidinone as colourless crystals, $[\alpha]_D = \div 61.2°$ (c=1 in methanol). Melting point 193°–195° C.

Elemental analysis for $C_{13}H_{15}N_3O_5$: Calculated: C 53.24, H 5.16, N 14.33%. Found: C 53.40, H 5.24, N 14.35%.

IR (KBr, cm$^{-1}$): 3414, 3315, 1757, 1701, 1610, 1540, 1498.

NMR (DMSO, ppm): 3.31–4.06 (3H, m, CH—CH$_2$—), 4.95 (1H, dd, 4.5 and 9 Hz, H$_3$), 5.06 (2H, s, $\phi$—CH$_2$), 6.53 (2H, broad, NH$_2$), 7.35 (5H, s, C$_6$H$_5$), 7.95 (1H, d, 9 Hz, CH$_3$—NH—CO), 8.35 (1H, s, NH—CO).

MS (CI with NH$_3$): 251 (M÷H)$^+$—CONH.

(k) 5.4 g (18.4 mmol) of (3S,4S)-cis-3-benzyloxycarboxamido-4-carbamoyloxymethyl-2-acetidinone in 200 ml of absolute dioxan are treated at room temperature with 4.3 g (1.3 equivalents) of pyridine/sulphur trioxide complex. The suspension obtained is stirred for 3 hours, subsequently treated with a further 0.99 g (0.3 equivalents) of pyridine-sulphur trioxide complex and the mixture is stirred for a further hour. After the addition of a further 1.37 g (0.4 equivalents) of pyridine-sulphur trioxide complex and stirring for a further 2 hours, the solvent is partially removed under reduced pressure and the residue is treated with 110 ml of saturated aqueous sodium bicarbonate solution. The brown solution obtained is left to stand in a refrigerator for 12 hours and the crystals obtained are filtered off. The mother liquor is chromatorgraphed [MCI gel, water/ethanol (1:1 to 9:1)]. After lyophilization, there are obtained 3.5 g (49%) of (3S,4S)-cis-3-benzyloxycarboxamido-4-carbamoyloxymethyl-2-azetidinone-1-sulphonic acid sodium salt as a colourless powder; $[\alpha]_D = \div 29.6°$ (c=0.5 in water).

Elemental analysis for $C_{13}H_{14}N_3O_8SNa$: Calculated: C 39.50, H 3.57, N 10.63%. Found: C 39.41, H 3.45, N 10.36%.

IR (KBr, cm$^{-1}$): 1798, 1758, 1739, 1693, 1584, 1547.

NMR (DMSO, ppm): 3.9–4.4 (3H, CH—CH$_2$), 4.9 (dd, 1H, NH—CH), 5.1 (s, 2H, $\phi$—CH$_2$), 6.4 (2H, broad, NH$_2$), 7.4 (5H, S, C$_6$H$_5$), 8.0 (1H, d, NH).

(l) 3.065 g (7.75 mmol) of (3R,4S)-cis-benzyloxycarboxamido-4-carbamoyloxymethyl-2-azetidinone-1-sulphonic acid sodium salt are dissolved in 180 ml of absolute methanol and the solution is hydrogenated for 1 hour in the presence of 1.5 g of 10% palladium/carbon. The catalyst is removed by filtration and the solution obtained is evaporated. 2.02 g (100%) of (3S,4S)-cis-3-amino-4-carbamoyloxymethyl-2-oxo-1-azetidinesulphonic acid sodium salt are obtained.

IR (KBr, cm$^{-1}$): 3444, 3207, 1754, 1725, 1611, 1249.

EXAMPLE 27

2.28 g (3.98 mmol) of (3S,4S)-3-[2-amino-4-thiazolyl)-2-(Z)-[[1-(t-butoxycarbonyl)-1-methylethoxy]imino]acetamido]-4-carbamoyloxymethyl-2-oxo-1-azetidinesulphonic acid sodium salt are treated with 5 ml of trifluoroacetic acid while cooling with ice. The ice-bath is removed and the mixture is stirred at room temperature for 30 minutes. Excess trifluoroacetic acid is removed under reduced pressure (20° C., 15 mmHg) and the oil obtained is treated with 100 ml of ether. The crystals obtained are filtered off, washed with ether and dried under greatly reduced pressure. After aqueous reverse-phase chromatography, there are obtained, after lyophilization, 1.51 g (76.6%) of (3S,4S)-3[(Z)-2-(2-amino-4-thiazolyl)-2-[[1-carboxy-1-methylethoxy]imino]acetamido]-4-carbamoyloxymethyl-2-oxo-1-azetidinesulphonic acid; $[\alpha]_D = \div 35.7°$ (c=0.3 in water).

Elemental analysis for $C_{14}H_{18}N_6O_{10}S_2$: Calculated: C 34.01, H 3.67, N 17.00%. Found: C 34.52, H 3.72, N 16.63%.

IR (KBr, cm$^{-1}$): 1764, 1722, 1680, 1637.

NMR (DMSO, ppm): 1.50 (6H, s, 2×CH$_3$), 4.00–4.20 (3H, CH—CH$_2$), 5.35 (1H, dd, 4.5 and 9 Hz, Hz), 6.50 (3H, broad, NH$_3^+$ or COCH, COHN$_2$), 6.90 (1H, s, thiazole-5H), 9.15 (1H, d, 9 Hz, CONH).

EXAMPLE 28

In a manner analogous to that described in Example 26, from 2-(2-amino-4-thiazolyl)-2-[[(Z)-(p-nitrobenzyloxycarbonyl)methoxy]imino]-acetic acid 2-benzthiazolyl thioester and (3S,4S)-3-amino-4-carbamoyloxymethyl-2-oxo-1-azetidinesulphonic acid there is obtained (3S,4S)-3-[(Z)-2-(2-amino-4-thiazolyl)-2-[[(p-nitrobenzyloxycarbonyl)methoxyimino]acetamido]-4-carbamoyloxymethyl-2-oxo-1-acetidinesulphonic acid sodium salt.

Elemental analysis for $C_{19}H_{18}N_7O_{12}S_2Na$: Calculated: C 36.60, H 2.91, N 15.73, S 10.28%. Found: C 37.00, H 2.88, N 15.74, S 10.45%.

IR (KBr, cm$^{-1}$): 3353, 1761, 1729, 1524, 1348.

NMR (DMSO, ppm): 4.0–4.2 (3H, m, CH—CH$_2$), 4.3 (2H, s, φ—CH$_2$), 5.30 (1H, dd, NH—CH—), 5.32 (2H, s, O—CH$_2$), 6.70 (2H, broad, NH$_2$), 6.9 (1H, s, S—CH=), 7.10 (2H, broad, NH$_2$), 7.70 and 8.2 (2×2H, 2d, 2×3 Hz, Ar), 9.5 (1H, d, 9 Hz, NHCO).

EXAMPLE 29

270 mg (0.43 mmol) of (3S,4S)-3-[(Z)-2-(2-amino-4-thiazolyl)-2[[(p-nitrobenzyloxycarbonyl)methoxy]imino]acetamido]-4-carbamoyloxymethyl-2-oxo-1-azetidinesulphonic acid sodium salt are dissolved in 30 ml of methanol and the solution is hydrogenated over 150 mg of 5% palladium-on-silica gel. The catalyst is filtered off and the solvent is evaporated. The residue is taken up in 2.5 ml of water and washed twice with ethyl acetate. The aqueous phase is chromatographed (reverse-phase using water as the eluting agent). There are obtained 115 mg (54%) of (3S,4S)-3-[(Z)-2-(2-amino-4-thiazolyl)-2-[(carboxymethoxy)imino]acetamido]-4-carbamoyloxymethyl-2-oxo-1-azetidinesulphonic acid sodium salt.

Elemental analysis for $C_{12}H_{13}N_6O_{10}S_2Na$: Calculated: C 29.51, H 2.68, N 17.21%. Found: C 27.09, H 2.35, N 15.33%.

IR (KBr, cm$^{-1}$): 3434, 1766, 1718, 1669, 1613, 1533, 1278, 1251.

NMR (DMSO, ppm): 3.90–4.15 (3H, m, CH—CH$_2$), 4.30 (2H, s, CH$_2$—COOH), 5.20 (1H, dd, 5 and 9 Hz, NH—CH), 6.6 (2H, broad, NH$_2$), 6.78 (1H, s, S—CH=), 7.13 (2H, s, NH$_2$), 10.90 (1H, d, 9 Hz, CONH).

EXAMPLE 30

In a manner analogous to that described in Example 26 there is likewise obtained:

(a) (3S,4S)-3-[(5-amino-3-(1,2,4-thiadiazolyl)]-2-(Z)-methoxyimino)acetamido]-4-carbamoyloxymethyl-2-oxo-1-azetidinesulphonic acid sodium salt.

Elemental analysis for $C_{10}H_{12}N_7O_8S_2Na$: Calculated: C 26.97, H 2.72, N 22.02, S 14.40%. Found: C 27.06, H 2.62, N 21.60, S 14.28%.

IR (KBr, cm$^{-1}$): 3330, 1767, 1720, 1675, 1617, 1524, 1276, 1252.

NMR (DMSO, ppm): 3.90 (3H, s, OCH$_3$), 3.90–4.30 (3H, m, CH—CH$_2$), 5.20 (1H, dd, 6 and 9 Hz, NH—CH), 6.35, (2H, s, NH$_2$), 8.10 (2H, s, NH$_2$), 9.04 (1H, d, 9 Hz, CONH).

$[\alpha]_{589}^{20}$ = +32.5° (c=0.4 in water).

The 2-[(5-amino-3-(1,2,4-thiadiazolyl)]-2-(Z)-methoxyimino-acetic acid 2-benzthiazolyl thioester used as the starting material can be prepared as follows:

(b) 2.0 g of 2-[5-amino-3-(1,2,4-thiadiazol-yl)]-2-(Z)-methoxyimino-acetic acid in 60 ml of acetonitrile are treated at room temperature with 1.3 ml of N-methylmorpholine. After 5 minutes, 3.6 g of dithio-bis-benzthiazol are added thereto, followed by dropwise addition of 2.2 ml of triethyl-phosphite in 10 ml of acetonitrile within 1 hour. The mixture is stirred at room temperature for 12 hours and subsequently filtered, washed with acetonitrile and low-boiling petroleum ether, dried and crystallized from tetrahydrofuran/low-boiling petroleum ether. There are obtained 1.4 g (40%) of 2-[5-amino-3-(1,2,4-thiadiazolyl)]-2-(Z)-methoxyiminoacetic acid 2-benzthiazolyl thioester of melting point above 160° C. (decomposition).

EXAMPLE 31

In a manner analogous to that described in Example 26 there is obtained (3S, 4S)-3-(2-amino-4-thiazolyl)-2-(Z)-methoxyimino]acetamido]-4-carbamoyloxymethyl-2-oxo-1-azetidinesulphonic acid sodium salt.

Elemental analysis for $C_{11}H_{13}N_6O_8S_2Na$: Calculated: C 29.73, H 2.95, N 18.91%. Found: C 29.91, H 3.30, N 19.00%.

IR (KBr, cm$^{-1}$): 3364, 1775, 1739, 1680, 1625, 1537, 1284, 1256.

NMR (DMSO, ppm): 3.90 (3H, s, OCH$_3$), 4.10 (3H, m, CH—CH$_2$), 5.25 (1H, dd, 4.5 and 9 Hz, CH—NH), 6.45 (2H, s, NH$_2$), 6.70 (1H, s, S—CH=), 7.10 (2H, s, NH$_2$), 9.10 (1H, d, 9 Hz, CONH).

EXAMPLE 32

(a) In a manner analogous to that described in Example 26 there is obtained (3S, 4S)-3-[(Z)-2-(2-amino-4-thiazolyl)-2-(methoxyimino)acetamido]-4-carbamoyl-2-oxo-1-azetidinesulphonic acid sodium salt.

Elemental analysis for $C_{10}H_{11}N_6O_7S_2Na$: Calculated: C 28.99, H 2.68, N 20.68%. Found: C 31.20, H 3.26, N 16.41%.

IR (KBr, cm$^{-1}$): 3282, 1790, 1640, 1612, 1527, 1260, 1230.

NMR (DMSO, ppm): 3.85 (3H, s, OCH$_3$), 4.3 (1H, d, 6 Hz, CH—CONH$_2$), 5.30 (1H, dd, 6 and 9 Hz, NH—CH), 6.95 (1H, s, S—CH=), 7.40 (2H, d, 18 Hz, CONH$_2$) 9.25 (1H, d, 9 Hz, NH—CO).

The (3S, 4S)-cis-3-amino-4-carbamoyl-2-azetidinone-1-sulphonic acid sodium salt used as the starting material can be prepared as follows:

(b) 17 g (42.7 mmol) of benzyl (3S, 4S)-cis-1-(2,4-dimethoxybenzyl)-4-formyl-2-oxo-3-azetidinecarbamate are dissolved in 100 ml of methylene chloride and 100 ml of n-propanol. This solution is treated with 3.5 g (50.3 mmol) of hydroxylamine hydrochloride, followed by 4.2 ml (52 mmol) of pyridine. The mixture is heated under reflux for 2 hours. The methylene chloride is subsequently distilled off and a solution of 6.3 g (57 mmol) of selenium dioxide in 100 ml of n-propanol is added dropwise. The mixture is heated under reflux for 2 hours and then cooled to room temperature and filtered. The solution obtained is evaporated under reduced pressure. The oil obtained is dissolved in 100 ml of n-propanol and evaporated. This procedure is repeated twice. The partially crystalline residue obtained is taken up in 250 ml of methylene chloride and washed successively twice with in each case 200 ml of water and sodium chloride solution. After drying over sodium sulphate, filtration and evaporation of the solvent, the residue is taken up in 70 ml of n-propanol. The solution is left to stand in a refrigerator for 12 hours. There are obtained 16.4 g (97%) of benzyl (3S, 4S)-cis-1-(2,4-dimethoxybenzyl)-4-cyano-2-oxo-3-acetidinecarbamate of melting point 152°–153° C.; $[\alpha]_D = +10.6°$ (c=1 in chloroform).

MS: 395 (M+).

(c) 15.72 g (58.2 mmol) of potassium peroxydisulphate and 9.5 g (54.8 mmol) of potassium hydrogen sulphate are dissolved in 480 ml of water. The solution is heated to 80° C. and treated with a solution of 1.2 g of copper sulphate in 10 ml of water. The suspension obtained is diluted with 180 ml of acetonitrile and treated dropwise with a solution of 14.4 g of benzyl (3S, 4S)-cis-1-(2,4-dimethoxybenzyl)-4-cyano-2-oxo-3-azetidinecarbamate in 300 ml of acetonitrile. The mixture is heated under reflux for 2.5 hours, subsequently cooled, filtered and partially evaporated. The oily aqueous solution obtained is extracted with ethyl acetate and the organic phase is washed successively three times with aqueous saturated sodium bicarbonate solution, water and sodium chloride solution. After drying and evaporation of the solvent, the oil obtained is chromatographed on silica gel [230–400 mesh, eluting agent ethyl acetate/n-hexane (1:1)]. There are obtained 6.1 g (68.3%) of benzyl (3S, 4S)-cis-4-cyano-2-oxo-3-azetidinecarbamate of melting point 163°–165° C.

MS: 245 (M+).

(d) 6.16 g (25 mmol) of benzyl (3S, 4S)-cis-4-cyano-2-oxo-3-azetidinecarbamate are dissolved in 45 ml of dimethyl sulphoxide and the solution is treated with 5.58 ml of 30% aqueous hydrogen peroxide. After the temperature has returned to 25° C., the mixture is treated with 5 ml of aqueous 1N sodium hydroxide solution. The temperature rises to 55° C. A precipitate results after stirring for 45 minutes. 20 ml of ethyl acetate are added thereto and the crystals obtained are filtered off. The crystals are washed with aqueous ethanol and absolute ether. There are obtained 2.48 g (37.5%) of benzyl (3S, 4S)-4-carbamoyl-2-oxo-3-azetidinecarbamate of melting point 248°–249° C.; $[\alpha]_D = +13°$ (c=1 in dimethyl sulphoxide).

The mother liquor is partially evaporated, a further 0.33 g of product being isolated. The thus-obtained mother liquor is diluted with water and chromatographed on MCI gel using ethanol/water (3:7) for the elution. The total yield of product amounts to 3.0 g (45.4%).

(e) 7.9 g (30 mmol) of benzyl (3S, 4S)-4-carbamoyl-2-oxo-3-azetidinecarbamate are dispersed in 470 ml of absolute dioxan and treated with 6.2 g (39 mmol) of pyridine-sulphur trioxide complex. The suspension obtained is stirred at room temperature for 2 hours, subsequently treated with 1.41 g (8.8 mmol) of pyridine-sulphur trioxide complex and stirred for a further hour. After the addition of 1.90 g (12 mmol) of pyridine-sulphur trioxide complex and stirring for a further 2 hours, the solvent is removed by evaporation under reduced pressure and the residue is taken up in 200 ml of water. The aqueous solution obtained is treated with 15 g (44.24 mmol) of tetrabutylammonium hydrogen sulphate. The aqueous solution is extracted twice with 250 ml of methylene chloride each time and the methylene chloride extract is dried over sodium sulphate. After evaporation of the solvent, the oily residue obtained is dissolved in 150 ml of absolute methanol and the solution is hydrogenated over 2.5 g of 10% palladium/carbon. The catalyst is filtered off, the solution is evaporated and the residue is dissolved in a solution of 70 ml of formic acid in 100 ml of methylene chloride. After 2 hours, the solvent is removed by evaporation and the residue is treated with 25 ml of water 2.3 g (36%) of (3S, 4S)-3-amino-4-carbamoyl-2-oxo-1-azetidinesulphonic acid are obtained. The mother liquor is chromatographed on MCI gel using water/ethanol (1:0 to 9:1) for the elution, a further 420 mg of product being obtained. The total yield is 2.7 g (43.3%).

IR (KBr, cm$^{-1}$): 1779, 1696, 1633, 1485, 1288, 1250.

NMR (DMSO, ppm): 4.43 and 4.72 (2×1H, 2d, 6 Hz, CH—CH), 7.88 (2H, d, br, NH$_2$), 8.59 (3H, br, NH$_3^+$).

EXAMPLE 33

In a manner analogous to that described in Example 32 or Example 26 there is obtained (3S, 4S)-3-[(Z)-2-[5-amino-3-(1,2,4-thiadiazolyl)]-2-methoxyimino)acetamido]-4-carbamoyl-2-oxo-1-azetidinesulphonic acid sodium salt.

Elemental analysis for C$_9$H$_{10}$N$_7$O$_7$S$_2$Na: Calculated: C 26.03, H 2.43, N 23.61%. Found: C 26.02, H 2.59, N 23.32%.

IR (KBr, cm$^{-1}$): 3424, 3334, 1776, 1688, 1618, 1524, 1278.

NMR (DMSO, ppm): 3.90 (3H, s, OCH$_3$), 4.45 (1H, d, 6 Hz, CH—CONH$_2$), 5.40 (1H, dd, 6 and 9 Hz, NH—CH, 7.30 (2H, br, NH$_2$), 8.10 (2H, br, NH$_2$), 8.8 (1H, d, 9 Hz, NH—CO).

EXAMPLE 34

In an manner analogous to that described in Example 32 or Examples 26 and 27 there is obtained (3S, 4S)-3-[(Z)-2-(2-amino-4-thiazolyl)-2-[[1-carboxy-1-methylethoxy]-imino]acetamido]-4-carbamoyl-2-oxo-1-azetidinesulphonic acid.

Elemental analysis for C$_{13}$H$_{16}$N$_6$O$_9$S$_2$: Calculated: C 33.62, H 3.47, N 18.10%. Found: C 33.24, H 3.18, N 17.94%.

IR (KBr, cm$^{-1}$): 3332, 3208, 2552, 1780, 1684, 1638, 1279, 1188.

NMR (DMSO, ppm): 1.44 (6H, s, 2×CH$_3$), 4.34 (1H, d, 6 Hz, CH—CONH$_2$), 5.33 (1H, dd, 6 and 9 Hz, NH—CH—), 6.96 (1H, s, S—CH=), 7.40 (2H, br, d, 7 Hz, CONH$_2$), 8.95 (1H, d, 9 Hz, CONH).

UV (EtOH): 292 nm (6846), 240 nm (12232).

EXAMPLE 35

(a) In a manner analogous to that described in Example 32, from (3S, 4S)-3-amino-4-[(R)-2,2-dimethyl-1,3-dioxolan-4-yl]-2-oxo-1-azetidinesulphonic acid and 2-(2-amino-4-thiazolyl)-2-(Z)-methoxyimino-acetic acid 2-benzthiazolyl thioester there is obtained (3S, 4S)-3-[(Z)-2-(2-amino-4-thiazolyl)-2-(methoxyimino)acetamido]-4-

(2,2-dimethyl-1,3-dioxolan-4-yl)-2-oxo-1-azetidinesulphonic acid sodium salt.

IR (KBr, cm$^{-1}$): 3429, 3345, 1770, 1673, 1620, 1531, 1253.

NMR (DMSO, ppm): 1.23 and 1.33 (2×3H, 2×CH$_3$), 3.83 (3H, s, OCH$_3$), 3.8–4.15 (4H, m, CH—CH—CH$_2$—), 5.22 (1H, dd, 5.5 and 9 Hz, NH—CH), 6.75 (1H, s, S—CH=), 7.19 (2H, br, NH$_2$), 8.68 (1H, d, 9 Hz, NH—CO).

(b) 740 mg (1.57 mmol) of (3S, 4S)-3-[(Z)-2-(2-amino-4-thiazolyl)-2-(methoxyimino)acetamido]-4-[(Z)-2,2-dimethyl-1,3-dioxolan-4-yl]-2-oxo-1-azetidinesulphonic acid sodium salt are dissolved in 40 ml of methanol/water (1:1) and the solution is stirred for 12 hours in the presence of 15 g of Amberlite IR 120 (previously washed in methanol). The catalyst is filtered off and the solvent is removed by evaporation. There are obtained 300 mg (0.7 mmol), (44%) of (3S, 4S)-2-[(Z)-2-(2-amino-4-thiazolyl)-2-(methoxyimino)acetamido]-4-[(R)-1,2-dihydroxyethyl]-2-oxo-1-azetidinesulphonic acid sodium salt.

Elemental analysis for C$_{11}$H$_{14}$N$_5$O$_8$S$_2$Na: Calculated: C 30.63, H 3.27, N 16.24%. Found: C 32.03, H 3.98, N 15.89%.

IR (KBr, cm$^{-1}$): 3290, 1772, 1742, 1678, 1638, 1270, 1227, 1045.

NMR (DMSO, ppm): 3.2–4.15 (4H, m, CH—CH—CH$_2$), 3.52 (3H, s, OCH$_3$), 5.19 (1H, dd, 6 and 9 Hz, NH—CH), 6.98 (1H, s, S—CH=), 7.1 (4H, br, NH$_2$, 2×OH), 9.23 (1H, d, 9 Hz, CONH).

(c) From (3S, 4S)-2-[(Z)-2-(2-amino-4-thiazolyl)-2-(methoxyimino)acetamido]-4-[(R)-1,2-dihydroxyethyl]-2-oxo-1-azetidinesulphonic acid sodium salt there is obtained in a manner analogous to that described in Example 26 (3S, 4S)-3-[(Z)-2-(2-amino-4-thiazolyl)-2-(methoxyimino)acetamido]-4-formyl-2-oxo-1-azetidinesulphonic acid sodium salt.

Elemental analysis for C$_{10}$H$_{10}$N$_5$O$_7$S$_2$Na: Calculated: C 30.08, H 2.52, N 17.54%. Found: C 31.27, H 3.02, N 17.67%.

IR (KBr, cm$^{-1}$): 3177, 1771, 1636, 1524, 1271.

NMR (DMSO, ppm): 3.93 (3H, s, OCH$_3$), 4.30 (1H, dd, 4.0 and 6 Hz, CH—CHO), 5.14 (1H, dd, 6.0 and 8.0 Hz, NH—CH), 5.5 (2H, br, NH$_2$), 6.77 (1H, s, S—CH=), 9.61 (1H, d, 8 Hz, NH—CO), 9.65 (1H, d, 4.0 Hz, CHO).

(d) 400 ml (1 mmol) of (3S, 4S)-3-[(Z)-2-(2-amino-4-thiazolyl)-2-(methoxyimino)acetamido]-4-formyl-2-oxo-1-azetidinesulphonic acid sodium salt are dissolved in 400 ml of methanol and the solution is treated with 100 mg (1.4 mmol) of hydroxylamine hydrochloride and 0.1 ml (1.24 mmol) of pyridine. After stirring for 2 hours, the mixture is evaporated and the product is chromatographed on silica gel [230–400 mesh, eluting agent methanol/ethyl acetate (3:7)]. The partially purified product is subsequently chromatographed on MCI gel using water as the eluting agent. There are obtained 45 mg (10%) of (3S, 4S)-3-[(Z)-2-(2-amino-4-thiazolyl)-2-(methoxyimino)acetamido]-4-[(E/Z)-(hydroxyimino)methyl]-2-oxo-1-azetidinesulphonic acid.

Elemental analysis for C$_{10}$H$_{11}$N$_6$O$_7$S$_2$Na: Calculated: C 28.99, H 2.68, N 20.28%. Found: C 30.06, H 3.34, N 18.68%.

IR (KBr, cm$^{-1}$): 3430, 1775, 1655, 1622, 1531, 1286, 1216.

NMR (DMSO, ppm): 3.82 (3H, s, OCH$_3$), 4.46 (1H, dd, 5.5 and 8.0 Hz, CH—CH=), 5.22 (1H, dd, 6 and 9 Hz, NH—CH), 6.57 (1H, s, S—CH=), 7.18 (2H, br, NH$_2$), 7.32 (1H, d, 8.0 Hz, CH=N), 9.29 (1H, 9 Hz, NH—CO), 11.0 (1H, s, CH).

The (3S, 4S)-3-amino-4-[(R)-2,2-dimethyl-1,3-dioxolan-4-yl ]-2-oxo-1-azetidinesulphonic acid used as the starting material can be prepared as follows:

(e) 0.25 g (0.78 mmol) of benzyl (3S, 4S)-cis-4-[(R)-2,2-dimethyl-1,3-dioxolan-4-yl]-2-oxo-3-azetidinecarbamate are dispersed in 4 ml of pyridine and treated with 0.5 g (3.1 mmol) of sulphur trioxide pyridinium complex. The mixture is heated for 1 hour. The solution is cooled and subsequently treated with 50 ml of ether. The ether is decanted off and the residue is treated with 300 ml of water. The solution is stirred at room temperature for 12 hours in the presence of ion exchanger Dowex 50 W (sodium form). The ion exchanger is filtered off and the solution is evaporated under reduced pressure. There are obtained 325 mg (100%) of crude (3S, 4S)-cis-3-benzyloxyformamido-4-[(R)-2,2-dimethyl-1,3-dioxolan-4-yl]-2-oxo-1-azetidinesulphonic acid sodium salt.

IR (KBr, cm$^{-1}$): 3329, 1775, 1724, 1698, 1526, 1257.

NMR (DMSO, ppm): 1.28 and 1.35 (2×3H, 2s, 2 CH$_3$), 3.8–4.4 (4H, m, CH—CH—CH$_2$), 4.99 (1H, dd, 6 and 10 Hz, NH—CH), 5.15 (2H, s, N—CH$_2$), 7.45 (5H, s, C$_6$H$_5$), 7.5 (1H, d, 10 Hz, CONH).

(f) The (3S, 4S)-cis-3-benzyloxyformamido-4-[(R)-2,2-dimethyl-1,3-dioxolan-4-yl]-2-oxo-1-azetidinesulphonic acid sodium salt is hydrogenated with palladium/carbon in a manner analogous to that described in Example 33, there being obtained (3S, 4S)-3-amino-4-[(R)-2,2-dimethyl-1,3-dioxolan-4-yl]-2-oxo-1-azetidinesulphonic acid.

EXAMPLE 36

(a) From (3S, 4S)-3-amino-4-methoxyiminomethyl-2-oxo-1-azetidinesulphonic acid and 2-(2-amino-4-thiazolyl)-2-(Z)-methoxyimino-acetic acid 2-benzthiazolyl thioester there is obtained in a manner analogous to that described in Example 1 (3S, 4S)-3-[(Z)-2-(2-amino-4-thiazolyl)-2-(methoxyimino)acetamido]-4-methoxyiminomethyl-2-oxo-1-azetidinesulphonic acid sodium salt.

Elemental analysis for C$_{11}$H$_{13}$N$_6$O$_7$S$_2$Na: Calculated: C 30.84, H 3.06, N 19.62%. Found: C 30.88, H 3.19, N 19.52%.

IR (KBr, cm$^{-1}$): 3424, 3336, 1772, 1671, 1622, 1532, 1274.

The (3S, 4S)-3-amino-4-methoxyiminomethyl-2-oxo-1-azetidinesulphonic acid used as the starting material can be prepared as follows:

(b) 3.0 g (7.5 mmol) of benzyl (3S, 4S)-[1-(2,4-dimethoxybenzyl)-4-formyl-2-oxo-3-azetidinyl]carbamate are dissolved in 40 ml of methylene chloride and the solution is treated with 0.7 g (8.5 mmol) of O-methylhydroxylamine hydrochloride and 0.73 ml (9.0 mmol) of pyridine. The mixture is stirred at room temperature for 2 days and subsequently washed with water and sodium chloride solution. After drying over sodium sulphate and evaporation of the solvent, the material is chromatographed [230–400 mesh, ethyl acetate/n-hexane (6:4)]. There are obtained 2.6 g (82%) of benzyl (2S, 4S)-1-(2,4-dimethoxybenzyl)-4-[(methoxyimino)methyl]-2-oxo-3-azetidinecarbamate (mixture of the E and Z isomers).

IR (KBr, cm$^{-1}$): 3290, 1772, 1686, 1210.

MS: 319 (M—φ—CH$_2$OH).

(c) 11.9 g (44 mmol) of potassium peroxydisulphate and 9.6 g of dipotassium hydrogen phosphate are dispersed in 110 ml of acetonitrile and 350 ml of water. The mixture is heated to 78° C. and a solution of 11.8 g (27.6 mmol) of benzyl (3S, 4S)-1-(2,4-dimethoxybenzyl)-4-[(methoxyimino)-methyl]-2-oxo-3-azetidinecarbamate (mixture of the E and Z isomers) in 300 ml of acetonitrile is added dropwise thereto. The pH of the solution is held at 7 by the addition of dipotassium hydrogen phosphate. After boiling for 6 hours, the mixture is cooled, the aqueous phase is discarded, the organic phase is diluted with ethyl acetate and washed successively with water, aqueous sodium bicarbonate solution and sodium chloride solution. After drying over sodium sulphate, the solvent is removed by evaporation and the crude mixture is chromatographed [230–400 mesh, ethyl acetate/n-hexane (8:2)], there being obtained 1.7 g (27%) of benzyl (3S, 4S)-4-[(methoxyimino)methyl]-2-oxo-3-azetidinecarbamate (mixture of the E and Z isomers); melting point 170°–171° C.

IR (KBr, cm$^{-1}$): 3310, 3210, 1790, 1732, 1533, 1258.

(d) 1.7 g (6.13 mmol) of benzyl (3S, 4S)-4-[(methoxyimino)methyl]-2-oxo-3-azetidinecarbamate (mixture of the E and Z isomers) are dissolved in 100 ml of absolute dioxan, the solution is treated with 1.26 g (7.9 mmol) of sulphur dioxide pyridinium complex and the mixture is stirred at room temperature for 1.5 hours. After the addition of a further 0.29 g (1.8 mmol) of sulphur trioxide pyridinium complex, the suspension is stirred for a further 1.5 hours. After the addition of 0.39 g (2.45 mmol) of sulphur trioxide pyridinium complex and stirring for a further 1 hour, the solvent is removed by evaporation under reduced pressure and the residue is treated with 30 ml of saturated aqueous sodium bicarbonate solution. The aqueous solution obtained is extracted twice with ethyl acetate and the organic phase is discarded. The aqueous phase is evaporated to 10 ml and chromatographed [(MCI gel; water/ethanol (1:0 to 9:1 to 7:3)]. There are obtained 1.36 g (58.5%) of (3S, 4S)-3-[(benzyloxy)formamido]-4-[(methoxyimino)methyl]-2-oxo-1-azetidinesulphonic acid (mixture of the E and Z isomers).

Elemental analysis for C$_{13}$H$_{14}$N$_3$O$_7$SNa: Calculated: C 41.16, H 3.72, N 11.08%. Found: C 40.21, H 3.81, N 10.72%.

IR (KBr, cm$^{-1}$): 3396, 3347, 1774, 1708, 1256.

(e) The thus-obtained (3S, 4S)-3-[(benzyloxy)formamido]-4-[(methoxyimino)methyl]-2-oxo-1-azetidinesulphonic acid is hydrogenated in a manner analogous to that described in the last paragraph of Example 26. In this manner there is obtained (3S, 4S)-3-amino-4-methoxyiminomethyl-2-oxo-1-azetidinesulphonic acid.

EXAMPLE 37

In a manner analogous to that described in Example 1, from (3S, 4S)-3-amino-4-methoxyiminomethyl-2-oxo-1-azetidinesulphonic acid (mixture of the E and Z isomers) and 2-[(5-amino-3-(1,2,4-thiadiazolyl)]-2-(Z)-methoxyiminoacetic acid 2-benzthiazolyl thioester there is obtained as the end product (3S, 4S)-3-[(5-amino-3-(1,2,4-thiadiazolyl)]-2-](Z)-(methoxyimino)acetamido]-4-methoxyiminomethyl-2-oxo-1-azetidinesulphonic acid sodium salt.

Elemental analysis for C$_{10}$H$_{12}$N$_7$O$_7$S$_2$Na: Calculated: C 27.97, H 2.82, N 22.84, S 14.93%. Found: C 28.50, H 3.37, N 24.07, S 14.79%.

IR (KBr, cm$^{-1}$): 3419, 1771, 1671, 1622, 1523, 1278.

EXAMPLE 38

(a) 378 mg (2.1 mmol) of (3S, 4S)-3-amino-4-methyl-2-oxo-1-azetidinesulphonic acid are dissolved in 60 ml of acetone/water (1:1) and the solution is treated with 1.3 g (2.3 mmol) of 2-(2-amino-4-thiazolyl)-2-[[(Z)-1-(p-nitrobenzyloxycarbonyl)-1-methylethoxy]imino]-acetic acid 2-benzthiazolyl thioester and 176 mg (2.1 mmol) of sodium bicarbonate. The mixture is stirred at room temperature for 12 hours. The acetone is removed by evaporation under reduced pressure and the residue is filtered. The aqueous solution obtained is evaporated. There are obtained 115 mg (10% of (3S, 4R)-3-[(Z)-2-(2-amino-4-thiazolyl)-2-[[1-(p-nitro-benzyloxycarbonyl)-1-methylethoxy]-imino]acetamido]-4-methyl-2-oxo-1-azetidinesulphonic acid sodium salt as an amorphous material.

IR (KBr, cm$^{-1}$): 3380, 1753, 1678, 1620, 1523, 1286, 1236.

NMR (DMSO, ppm): 1.24 (3H, d, J=6 Hz, CH—CH$_3$), 1.46 and 1.50 (2×3H, 2s, (CH$_3$)$_2$C), 3.99 (1H, m, CH—CH$_3$), 5.10 (1H, dd, J=6 and 9 Hz, NH—CH), 5.33 (2H, s, O—CH$_2$), 6.69 (1H, s, S—CH=), 7.30 (2H, br, NH$_2$), 7.59—8.18 (4H, m, Ar), 9.26 (1H, d, 9 Hz, NHCO).

The 2-(2-amino-4-thiazolyl)-2-[[(Z)-1-(p-nitrobenzyloxycarbonyl)-1-methylethoxy]imino]-acetic acid 2-benzthiazolyl thioester used as the starting material can be prepared as follows:

(b) 33.0 g (136 mmol) of t-butyl 2-(2-amino-4-thiazolyl)-2-(Z)-hydroxyimino-acetate are dissolved in 500 ml of dimethylformamide. After the addition of 84.5 g (272 mmol) of p-nitrobenzyl 2-bromo-2-methylpropionate and 75.2 g (544 mmol) of finely powdered potassium carbonate, the mixture is stirred at 45° C. for 5 hours in a nitrogen atmosphere. The mixture is cooled to room temperature and poured into a mixture of 5 l of water and 2.5 l of ethyl acetate. The organic phase is washed three times with a total of 2.5 l of water. The aqueous phase is extracted with 2.5 l of ethyl acetate. The combined ethyl acetate solutions are dried over sodium sulphate and evaporated to dryness. There are obtained 42 g (66.4%) of t-butyl-2-(2-amino-4-thiazolyl)-2-[[(Z)-(p-nitrobenzyloxycarbonyl)-1-methylethoxy]imino]-acetate of melting point 150.3° C.

(c) 23.4 g (50.4 mmol) of t-butyl 2-(2-amino-4-thiazolyl)-2-[[(Z)-1-(p-nitrobenzyloxycarbonyl)-1-methylethoxy]imino]-acetate are dispersed in 60 ml of trifluoroacetic acid and stirred at room temperature for 30 minutes. The solution obtained is evaporated, the residue is dissolved in 200 ml of toluene and the solution is evaporated. After the addition of 700 ml (280 mmol) of a 0.4M aqueous sodium bicarbonate solution, the pH is adjusted to 3.8 with acetic acid. The precipitated crystals are filtered off and dried at 50° C. under reduced pressure (0.05 mm). There are obtained 17.3 g (84%) of 2-(2-amino-4-thiazolyl)-2-[[(Z)-1-(p-nitrobenzyloxycarbonyl)-1-methylethoxy]imino]-acetic acid of melting point 194° C. (decomposition).

The water content of the product is reduced to 0.26%, which is advantageous for the following reaction, by two-fold suspension in 100 ml of dry acetonitrile each time and evaporation of the solvent, followed by drying for 20 hours at room temperature under reduced pressure (0.1 mm).

(d) 16.4 g (40.2 mmol) of 2-(2-amino-4-thiazolyl)-2-[[(Z)-1-(p-nitrobenzyloxycarbonyl)-1-methylethoxy]imino]-acetic acid are dispersed in 250 ml of acetonitrile (dried with molecular sieve 3 Å. After the addition of 5.6 ml (50.8 mmol) of N-methylmorpholine while stirring, there are added thereto, likewise while stirring, 16.0 g (48 mmol) of 2,2-dithio-bis-benzthiazole and 9.2 ml (44.4 mmol) of triethylphosphite. The suspension obtained has an intense yellow colour. After stirring at room temperature for 1 hour, the mixture is cooled to 0° C., the crystals obtained are filtered off after 1 hour and dried at 50° C. under reduced pressure (0.1 mm). There are obtained 16.1 g (72.2%) of 2-(2-amino-4-thiazolyl)-2-[[(Z)-1-(p-nitrobenzyloxycarbonyl)-1-methylethoxy]imino]-acetic acid 2-benzthiazolyl thioester of melting point 162°–164° C.

EXAMPLE 39

115 mg (0.19 mmol) of (3S, 4R)-3-[(Z)-2-(2-amino-4-thiazolyl)-2-[[1-(p-nitro-benzyloxycarbonyl)-1-methylethoxy]imino]acetamido]-4-methyl-2-oxo-1-azetidinesulphonic acid sodium salt are dissolved in 40 ml of water/tetrahydrofuran (1:1) and the solution is hydrogenated for 12 hours over 300 ml of 10% palladium/carbon. The catalyst is filtered off and the solvent is evaporated under reduced pressure. The oil obtained is chromatographed (230–400 mesh, chloroform/methanol/n-propanol/water (4:6:1:4) as the solvent]. There are obtained 28.6 mg (33%) of (3S, 4R)-3-[(Z)-2-(2-amino-4-thiazolyl)-2-[(1-carboxy-1-methylethoxy)imino]acetamido]-4-methyl-2-oxo-1-azetidindsulphonic acid sodium salt.

IR (KBr, cm$^{-1}$): 3297, 2984, 2683, 1763, 1675, 1631, 1535, 1276.

NMR (DMSO, ppm): 1.1 and 1.20 (6H, 2s, 2×CH$_3$), 1.45 (3H, d, 3.5 Hz, CH—CH$_3$), 4.0 (1H, m, CH—CH$_3$), 5.05 (1H, dd, 6 and 9 Hz, NH—CH), 6.75 (1H, s, S—CH=), 7.20 (3H, br, NH$_3^+$), 9.15 (1H, d, 9 Hz, CONH).

EXAMPLE 40

In the same manner as described in Example 1, from (3S, 4S)-3-amino-4-carbamoyloxymethyl-2-oxo-1-azetidinesulphonic acid and 2-(2-amino-4-thiazolyl)-2-[[(Z(-t-butoxycarbonyl)methoxy]imino]-acetic acid 2-benzthiazolyl thioester there is obtained as the end product (3S, 4S)-3-[(Z)-2-(2-amino-4-thiazolyl)-2-[[(t-butoxycarbonyl)methoxy]imino]acetamido]-4-carbamoyloxymethyl-2-oxo-1-azetidinesulphonic acid triethylamine salt. This salt is brought into solution in ethanol (about 4%). The product is precipitated as the sodium salt by adding an equivalent amount of a 2N solution of sodium 2-ethyl caproate in ethyl acetate, 2 volumes of acetone and 4 volumes of diethyl ether.

$^1$H-NMR (DMSO, ppm): 9.15 (d, J=9.5 Hz, 1H); 7.20 (s, br, 2H); 6.75 (s, 1H); 6.46 (s, br, 2H); 5.28 (dd, J=4 Hz, J=9 Hz, 1H); 4.53 (s, 2H); 4.0–4.3 (m, 3H); 1.43 (s, 9H).

The 2(2-amino-4-thiazolyl)-2-[[(Z)-(t-butoxycarbonyl)methoxy]imino]-acetic acid 2-benzthiazolyl thioester used as the starting material can be prepared as follows:

(A) 245 g (1.0 mol) of 2-(2-amino-4-thiazolyl)-2-(Z)-(hydroxyimino)-acetic acid are dispersed at room temperature in 2.2 l of dimethylformamide and treated with 245 g (1.13 mol) of p-nitrobenzyl bromide and 170 g (1.13 mol) of sodium iodide. The mixture is stirred in a nitrogen or argon atmosphere for 12 hours. The brown solution obtained is treated with 190 ml (1.29 mol) of t-butyl bromoacetate and 386 ml (2.25 mol) of N-ethyldiisopropylamine. After stirring at room temperature for 1 hour, the mixture is poured into 8 l of water and the resulting mixture is extracted with 4 l of ethyl acetate. The ethyl acetate phase is washed with 3 l of water. The aqueous phases are extracted in two portions with 5 l of ethyl acetate. The combined ethyl acetate phases are concentrated to 1 l and cooled in an ice-bath. The crystals which thereby result are filtered off, washed with cold ethyl acetate and ether and dried at 50° C. under reduced pressure. There are obtained 248 g (57%) of p-nitrobenzyl 2-(2-amino-4-thiazolyl)-2-[[(Z)-(t-butoxycarbonyl)methoxy]imino]-acetate.

Elemental analysis for C$_{18}$H$_{20}$N$_4$O$_7$S (436.447): Calculated: C 49.54, H 4.62, N 12.84, S 7.35%. Found: C 49.57, H 4.69, N 12.73, S 7.30%.

109 g (0.25 mol) of p-nitrobenzyl 2-(2-amino-4-thiazolyl)-2-[[(Z)-(t-butoxycarbonyl)methoxy]imino]-acetate are dispersed in 2 l of methanol. After the addition of 42 ml (0.30 mol) of triethylamine and 55 g of Raney-nickel, the mixture is shaken in a hydrogen atmosphere for 2.5 hours. 20.5 l of hydrogen are consumed. The catalyst is removed by filtration over siliceous earth and the filtrate is evaporated. The residue is dissolved in 600 ml of water and extracted with two 1000 ml portions of ethyl acetate. The ethyl acetate phase is washed with two 200 ml portions of water. The aqueous phases are combined and filtered, the filtrate then being adjusted to pH 3 by treatment with about 250 ml of 1N aqueous hydrochloric acid while stirring. The crystals obtained are filtered off, washed with acetonitrile and water and dried under reduced pressure at 45° C. for 16 hours. The thus-obtained crystalline material contains about 5% of water. Treatment with isopropanol reduces the water content 0.9%. Therefore, the crystals containing the 5% of water are dispersed in 100 ml of dry isopropanol, stirred at room temperature for 12 hours and dried at 45° C. for 16 hours under reduced pressure. 67 g (89%) of 2-(2-amino-4-thiazolyl)-2-[[(Z)-(t-butoxycarbonyl)methoxy]imino]-acetic acid are obtained.

Elemental analysis for $C_{11}H_{15}N_3O_5S$ (301.324): Calculated: C 43.85, H 5.02, N 13.95, S 10.64%. Found: C 43.73, H 5.06, N 13.73, S 10.42, $H_2O$ 0.89%.

The starting material can also be prepared as follows:

(B) 84 g of diketene are dissolved in 250 ml of carbon tetrachloride and the solution is cooled to −27° C. The solution is turbid. 71 g of chlorine gas are introduced slowly within 5 hours while stirring, the temperature being held at −20° C. to −30° C. by cooling. The clear solution obtained is added slowly within 1 hour while stirring at 0° C. to −5° C. to a solution of 58 g of allyl alcohol in 250 ml of carbon tetrachloride and 80.5 ml of pyridine. After stirring for a further 15 minutes without cooling, the precipitated pyridine hydrochloride is filtered off and washed with 100 ml of carbon tetrachloride. The carbon tetrachloride solution is washed with two 300 ml portions of water, dried over sodium sulphate and evaporated under reduced pressure. The residue is distilled, there being obtained 136 g (77%) of allyl 4-chloro-acetoacetate as a colourless liquid of boiling point 61°–69° C./0.1 mmHg.

A solution of 35.2 g of allyl 4-chloro-acetoacetate in 34 ml of acetic acid is treated dropwise within 45 minutes while stirring and cooling with a solution of 14.6 g of sodium nitrite in 21 ml of water. During the addition the temperature falls gradually from 0° C. to −15° C. The mixture is subsequently stirred at −15° C. for 2 hours.

A solution of 15.2 g of thiourea in 120 ml of water, pre-warmed to 30° C., is treated with the resulting solution at such a rate that the temperature remains at about 30°–35° C. After stirring for an additional 7 hours, the crystalline precipitate obtained is filtered off, washed successively with water, acetonitrile and ether and crystallized from acetonitrile. There are obtained 21.8 g (48%) of allyl 2-(2-amino-4-thiazolyl)-2-(Z)-hydroxyimino-acetate of melting point 184°–185° C.

A solution of 20.4 g of allyl 2-(2-amino-4-thiazolyl)-2-(Z)-hydroxyimino-acetate in 100 ml of dimethyl sulphoxide and 100 ml of acetone is stirred at room temperature for 5 hours together with 30 g of potassium carbonate and 19.5 ml of t-butyl bromoacetate. After removal of the acetone by evaporation under reduced pressure (bath temperature 50° C.), 600 ml of ethyl acetate are added thereto and the solution is washed with ice-water until neutral, dried and evaporated under reduced pressure. There is obtained a yellowish crystalline residue which is dispersed in diisopropyl ether, filtered and dried under reduced pressure. There are obtained 20.1 g (65.5%) of allyl 2-(2-amino-4-thiazolyl)-2-[[(Z)-(t-butoxycarbonyl)methoxy]imino]-acetate of melting point 135°–136° C.

19 g of allyl 2-(2-amino-4-thiazolyl)-2-[[(Z)-(t-butoxycarbonyl)methoxy]imino]-acetate in 500 ml of ethyl acetate are treated successively while stirring with 0.9 g of palladium chloride, 0.46 ml of triethyl phosphite and 30 ml of sodium 2-ethyl caproate solution (2N solution in ethyl acetate). After stirring at room temperature for 4 hours, 500 ml of water and 100 ml of saturated aqueous sodium bicarbonate solution are added thereto. The aqueous solution is separated, washed with 100 ml of ethyl acetate and acidified to pH 2 with 2N aqueous hydrochloric acid. The crystalline precipitate is filtered off, washed successively with water, acetonitrile and ether and dried under reduced pressure. There are obtained 14.6 g (87%) of 2-(2-amino-4-thiazolyl)-2-[[(Z)-(t-butoxycarbonyl)methoxy]imino]-acetic acid of melting point 175°–176° C. (decomposition).

The following are further methods for the preparation of the starting material:

(C) The allyl 2-(2-amino-4-thiazolyl)-2[[(Z)-(t-butoxycarbonyl)methoxy]imino]-acetate is reacted in the same manner as described in section (B), but using 0.12 g of palladium acetate in place of palladium chloride. After identical working-up, there are obtained 14.5 g (86.3%) of 2-(2-amino-4-thiazolyl)-2-[[(Z)-(t-butoxycarbonyl)methoxy]imino]-acetic acid of melting point 171°–172° C.

(D) The allyl 2-(2-amino-4-thiazolyl)-2-[[(Z)-(t-butoxycarbonyl)methoxy]imino]-acetate is reacted in a manner analogous to that described in section (C), but using 0.695 g of triphenylphosphine in place of triethyl phosphite. There are obtained 13.4 g (79.7%) of 2-(2-amino-4-thiazolyl)-2-[[(Z)-(t-butoxycarbonyl)methoxy]imino]-acetic acid of melting point 167°–169° C.

(E) A suspension of 1.4 g of allyl 2-(2-amino-4-thiazolyl)-2-[[(Z)-(t-butoxycarbonyl)methoxy]imino]-acetate, 86 mg of 5% palladium/carbon, 0.033 ml of triethyl phosphite and 2.25 ml of sodium 2-ethylcaproate solution (2N solution in ethyl acetate) in 50 ml of ethyl acetate is stirred at 60° C. for 12 hours. After cooling to room temperature, the mixture is worked-up as described in section (B) above. There is obtained 0.81 g (65.5%) of 2-(2-amino-4-thiazolyl)-2-[[(Z)-(t-butoxycarbonyl)methoxy]imino]-acetic acid of melting point 174°–175° C.

(F) 3.41 g of allyl 2-(2-amino-4-thiazolyl)-2-[[(Z)-(t-butoxycarbonyl)methoxy]imino]-acetate are dispersed in 100 ml of ethyl acetate and treated with 250 mg of triphenylphosphine and 250 mg of tetrakis-(triphenylphosphine)-palladium. The solution obtained is treated with 5.5 ml of sodium 2-ethylcaproate solution (2N solution in ethyl acetate). A thick pulp-like mass which can not be stirred results within a short time. After standing at room temperature for 15 minutes, this mass is shaken once with 100 ml of water and once with 30 ml of saturated aqueous sodium carbonate solution. The aqueous solutions are combined and washed once with 50 ml of ethyl acetate. The combined aqueous solutions are adjusted to pH 2 with 2N aqueous hydrochloric acid. The crystalline precipitate is filtered off and washed successively with water, acetonitrile and ether. There are obtained 2.4 g of 2-(2-amino-4-thiazolyl)-2-[[(Z)-(t-butoxycarbonyl)methoxy]imino]-acetic acid of melting point 167°–169° C. (decomposition).

(G) 3.41 g of allyl 2-(2-amino-4-thiazolyl)-2-[[(Z)-(t-butoxycarbonyl)methoxy]imino]-acetate are dispersed in 100 ml of ethyl acetate and treated with 18 mg of palladium chloride and 0.084 ml of triethyl phosphite. After the addition of 1.2 ml of N-methylmorpholine, the mixture is stirred at room temperature for 48 hours, crystallization occurring slowly. The mixture is left to stand for 4 days, the precipitate is filtered off under suction, washed with ethyl acetate and dried in vacuo. There are obtained 3.52 g of the N-methylmorpholine salt of 2-(2-amino-4-thiazolyl)-2-[[(Z)-(t-butoxycarbonyl)methoxy]imino]-acetic acid.

The crude salt is suspended in 100 ml of dry acetonitrile. 0.49 ml of N-methylmorpholine and 3.32 g of 2,2-dithio-bis-benzthiazole are successively added thereto while stirring and the suspension obtained is cooled to 5° C. A solution of 2.5 ml of triethyl phosphite in 30 ml of dry acetonitrile is now added dropwise within 4 hours. After stirring for a further 30 minutes, the yellow suspension obtained is cooled to −10° C. The crystals are filtered off under suction and washed with cold acetonitrile and ether. There are obtained 1.9 g of 2-(2-amino-4-thiazolyl)-2-[[(Z)-(t-butoxycarbonyl)methoxy]imino]-acetic acid 2-benzthiazolyl thioester of melting point 142°–143° C. (decomposition).

54.2 g (180 mmol) of 2-(2-amino-4-thiazolyl)-2-[[(Z)-(t-butoxycarbonyl)methoxy]imino]-acetic acid are dispersed in 1.4 l of dry acetonitrile. There are added thereto 29.6 ml (270 mmol) of N-methylmorpholine, followed by 72.1 g (216 mmol) of 2,2-dithio-bis-benzthiazole. The suspension obtained is cooled to 0° C. Within 4.5 hours there is now added thereto a solution of 53.8 ml (314 mmol) of triethyl phosphite in 350 ml of dry acetonitrile. After stirring for a further 30 minutes, the yellow suspension obtained is cooled to −10° C. The crystals are filtered off and washed with cold acetonitrile and ether. There are obtained 59.7 g (73.6%) of 2-(2-amino-4-thiazolyl)-2-[[(Z)-(t-butoxycarbonyl)methoxy]imino]-acetic acid 2-benzthiazolyl thioester.

Elemental analysis for $C_{18}H_{18}N_4O_4S_3$ (450.561): Calculated: C 47.99, H 4.03, N 12.44, S 21.35%. Found: C 47.88, H 4.34, N 12.34, S 21.02%.

EXAMPLE 41

71.8 g (0.3 mol) of (3S, 4S)-3-amino-4-carbamoyloxymethyl-2-oxo-1-azetidinesulphonic acid are dispersed in 1.5 l of methylene chloride and treated while stirring with 45.6 g (0.45 mol) of triethylamine and 148.6 g (0.33 mol) of 3-(2-amino-4-thiazolyl)-2-[[(Z)-(t-butoxycarbonyl)methoxy]imino]-acetic acid 2-benzthiazolyl thioester. The mixture is stirred at room temperature for 5 hours. 1.5 l of water are subsequently added thereto, the aqueous phase is separated, extracted twice with 250 ml of methylene chloride and acidified by the addition of 850 ml of 37% aqueous hydrochloric acid. After stirring at room temperature for 2 hours, the suspension obtained is cooled to 0° C. and stirred for a further 0.5 hour. The precipitate is filtered off, washed successively with 1000 ml of cold water, 1000 ml of methanol and 1000 ml of ether and dried at 40° C/10 mmHg for 12 hours. There are obtained 111 g (79.3%) of crude (3S, 4S)-3-[(Z)-2-(2-amino-4-thiazolyl)-2-[(carboxymethoxy)imino]acetamido]-4-carbamoloxymethyl-2-oxo-1-azetidinesulphonic acid of melting point 207° C.; $[\alpha]_D^{20} = -46.2°$ (c=1 in dimethyl sulphoxide).

Elemental analysis for $C_{12}N_{14}N_6O_{10}S_2$: Calculated: C 30.90, H 3.03, N 18.02, S 13.75%. Found: C 28.23, H 3.81, N 16.18, S 12.26, $H_2O$ 3.61%. Corrected for anhydrous substance C 29.29, H 3.53, N 16.79, S 12.72%.

An analytical sample gives the following data:

$[\alpha]_D^{20} = +39°$ (c=1 in water); corrected for anhydrous substance +42.5° (c=0.9 in water).

$[\alpha]_D^{20} = -43.5°$ (c=1 in dimethyl sulphoxide); corrected for anhydrous substance −47.4° (c=0.9 in water).

IR (KBr, $cm^{-1}$): 3458, 3428, 3354, 3291, 1777, 1712, 1648, 1617, 1557, 1531.

$^1$H-NMR (DMSO, ppm): 3.9–4.4 (3H, m, CH—CH$_2$—O) 4.79 (2H, s, O—CH$_2$—COOH), 5.30 (1H, dd, 5 and 9 Hz, NH—CH—CH); 6.5 (6H, br, $NH_3^+$, $NH_2$, COOH), 6.90 (1H, s, H-thiazole), 9.45 (1H, d, 9 Hz, CO—NH).

Elemental analysis for $C_{12}H_{14}N_6O_{10}S_2$: Calculated: C 30.90, H 3.03, N 18.02, S 13.75%. Found: C 28.39, H 3.43, N 16.44, S 12.47, $H_2O$ 8.14%. Corrected for anhydrous substance C 30.91, H 2.74, N 17.90, S 13.58%.

EXAMPLE 42

110 g (0.235 mol) of crude (3S,4S)-3-[(Z)-2-(2-amino-4-thiazolyl)-2-[(carboxymethoxy)imino]acetamido]-4-carbamoyloxymethyl-2-oxo-1-azetidinesulphonic acid (obtained according to Example 41) are dispersed in 4.7 l of methanol and treated with 72.3 ml (0.518 mol) of triethylamine and 282.9 ml (0.566 mol) of a 2N solution of sodium 2-ethylcaproate in ethyl acetate. The solution obtained is stirred for 10 minutes, diluted with 9 l of acetone and concentrated to 3 l. The residual suspension is diluted with 3 l of acetone, filtered and the crystalline salt is washed with ether and dried. 108.59 g (90.5%) of (3S,4S)-3-[(Z)-2-(2-amino-4-thiazolyl)-2-[(carboxymethoxy)-imino]acetamido]-4-carbamoyloxymethyl-2-oxo-1-azetidinesulphonic acid disodium salt are obtained. This crude salt is dissolved in 420 ml of water. 1050 ml of ethanol are added thereto and subsequently (after a few minutes) a further 210 ml of ethanol are added. The solution is turbid and is stirred for 1 hour. 1770 ml of ethanol are now added dropwise thereto within 2 hours. After stirring for a further 1 hour and cooling to 0° C., the precipitate is filtered off and washed with ethanol. The crystals obtained are dispersed in 170 ml of ethanol and 680 ml of ether, filtered off and washed with ether. After drying under greatly reduced pressure at 40° C., there obtained 102.9 g (85.5%) of (3S,4S)-3-[(Z)-2-(2-amino-4-thiazolyl)-2-[(carboxymethoxy)imino]acetamido]-4-carbamoyloxymethyl-2-oxo-1-azetidinesulphonic acid disodium salt.

Elemental analysis for $C_{12}H_{12}N_6O_{10}S_2Na_2$: Calculated: C 28.24, H 2.37, N 16.47, S 12.56%. Found: C 28.18, H 2.63, N 16.34, S 12.21, $H_2O$ 1.02%. Corrected for anhydrous substance C 28.48, H 2.65, N 16.50, S 12.33%.

$[\alpha]_D^{20} = +19°$ (c=1 in water)

IR (KBr, $cm^{-1}$): 1777, 1712, 1648, 1617, 1557, 1417.

UV [$H_2O$; λ max (ε)]: 295 nm (6850), 233 nm (12330).

¹H-NMR (D₂O, ppm): 4.2–4.8 (5H, m, CH—CH₂—O—CO, O—CH₂—COONa), 5.6 (1H, d, 5.5 Hz, O=C—CH), 7.05 (1H, s, H-thiazole).

EXAMPLE 43

In the same manner as described in Example 1, from 191 mg of (3S,4S)-3-amino-4-carbamoyloxymethyl-2-oxo-1-azetidinesulphonic aicd and 2-[5-(1-t-butoxyformamido)-3-(1,2,4-thiadiazolyl)]-2-[[(Z)-(t-butoxycarbonyl)-methoxy]imino]-acetic acid 2-benzthiazolyl thioester there are obtained as the end product 355 mg of (3S,4S)-3-[(Z)-2-[[(t-butoxycarbonyl)methoxy]imino]-2-[5-(1-t-butoxyformamido)-1,2,4-thiadiazol-3-yl]acetamido]-4-carbamoyloxymethyl-2-oxo-1-azetidinesulphonic acid triethylamine salt.

¹H-NMR (DMSO, ppm): 9.1 (d, J=9 Hz, 1H), 6.30 (s, br, 2H); 5.24 (dd, J=4 Hz, J=9 Hz, 1H); 4.63 (s, 2H); 4.0–4.3 (m, 3H); 3.04 (q, J=7.3 Hz, 6H); 1.53 (s, 9H); 1.44 (s, 9H); 1.16 (t, J=7.3 Hz, 9H).

The 2-[5-(1-t-butoxyformamido)-3-(1,2,4-thiadiazolyl)]-2-[[(Z)-(t-butoxycarbonyl)methoxy]imino]-acetic acid 2-benzthiazolyl thioester used as the starting material can be prepared as follows:

2 g of 2-[5-(1-t-butoxyformamido)-3-(1,2,4-thiadiazolyl)]-2-[[(Z)-(t-butoxycarbonyl)methoxy]imino]-acetic acid and 2 g of 2,2-dithio-bis-benzthiazole are suspended in 50 ml of acetonitrile and 0.7 ml of N-methylmorpholine and treated while stirring within 1 hour with 1.1 ml of triethyl phosphite in 10 ml of acetonitrile. The product is taken up in ethyl acetate, washed with water, dried and concentrated. The residual yellow oil is chromatographed on silica gel. The thioester crystallizes from hexane (0.8 g). There is obtained 2-[5-(1-t-butoxyformamido)-3-(1,2,4-thiadiazolyl)]-2-[[(Z)-(t-butoxycarbonyl)methoxy]imino]-acetic acid 2-benzthiazolyl thioester of melting point 115°–120° C.

Elemental analysis: Calculated: C 47.96, H 4.57, N 12.70, S 17.43%. Found: C 48.06, H 4.83, N 12.46, S 17.77%.

EXAMPLE 44

804 mg (2 mmol) of 2-[5-(1-t-butoxyformamido)-3-(1,2,4-thiadiazolyl)]-2-[[(Z)-(t-butoxycarbonyl)methoxy]imino]-acetic acid 2-benzthiazolyl thioester are dissolved in 30 ml of methylene chloride and the solution is treated with 0.25 ml (2.05 mmol) of 1-chloro-N,N,2-trimethyl-1-propenamine, followed by 0.57 ml (2.05 mmol) of triethylamine and 478 mg (2 mmol) of (3S,4S)-3-amino-4-carbamoyloxymethyl-2-oxo-1-azetidinesulphonic acid. The mixture is stirred for 12 hours and subsequently evaporated. The residue is treated with a solution of 370 mg of sodium bicarbonate in 30 ml of water. The crude mixture is chromatographed on MCI gel using 25% aqueous methanol for the elution, there being obtained 406 mg (34%) of (3S,4S)-3-[(Z)-2-(5-amino-1,2,4-thiadiazol-3-yl)-2-[[(t-butoxycarbonyl)methoxy]imino]acetamido]-4-carbamoyloxymethyl-2-oxo-1-azetidinesulphonic acid triethylamine salt.

Elemental analysis for $C_{21}H_{36}N_8O_{10}S_2$: Calculated: C 40.38, H 5.81, N 17.94%. Found: C 40.31, H 5.70, N 17.99%.

¹H-NMR (DMSO, ppm): 1.17 (9H, t, 7.5 Hz, 3×CH₂CH₃), 1.42 (9H, s, 3×CH₃), 3.09 (6H, q, J=7.5 Hz, 3×CH₂), 4.10 (3H, m, CH—CH₂), 4.60 (2H, s, N—O—CH₂), 5.25 (1H, dd, J=5 and 9 Hz, NH—CH), 6.30 (2H, s, NH₂), 8.10 (2H, s, NH₂), 9.0 (1H, d, J=9 Hz NH—CH).

EXAMPLE 45

314 mg (0.502 mmol) of (3S,4S)-3-[(Z)-2-(5-amino-1,2,4-thiadiazol-3-yl)-2-[[(t-butoxycarbonyl)methoxy]imino]-acetamido]-4-carbamoyloxymethyl-2-oxo-1-azetidinesulphonic acid triethylamine salt are dissolved at 0° C. in 5 ml of 3.5N aqueous hydrochloric acid. The mixture is stirred at 0° C. for 2 days. The solvent is removed by evaporation under reduced pressure, the residue is taken up in 15 ml of ethanol/water (2:1) and treated with 2 ml of 2N sodium 2-ethylcaproate in ethyl acetate. The mixture is concentrated and the residue is chromatographed on MCI gel using water for the elution. There are obtained 135 mg (53%) of (3S,4S)-3-[(Z)-2-(5-amino-1,2,4-thiadiazol-3-yl)-2-[(carboxymethoxy)imino]acetamido]-4-carbamoyloxymethyl-2-oxo-1-azetidinesulphonic acid disodium salt.

Elemental analysis for $C_{11}H_{11}N_7O_{10}S_2Na_2$. NaCl: Calculated: C 23.41, H 1.81, N 17.20, S 11.03, Cl 6.52%. Found: C 23.19, H 1.95, N 17.21, S 11.15, Cl 6.22%.

IR (KBr, cm⁻¹): 1767, 1664, 1614.

¹H-NMR (DMSO, ppm): 4–4.20 (3H, m, CH—CH₂), 4.30 (2H, s, N—O—CH₂), 5.26 (1H, dd, J=5 and 10 Hz, NH—CH), 6.50 (2H, br, NH₂), 8.11 (2H, s, NH₂), 10.90 (1H, d, J=10 Hz, NH—CH).

EXAMPLE 46

In the same manner as described in Example 1, from 352 mg (1.5 mmol) (3S,4S)-3-amino-4-[(E)-2-carbamoylvinyl] -2-oxo-1-azetidinesulphonic acid and 2-(2-amino-4-thiazolyl)-2-(Z)-methoxyimino-acetic acid 2-benzthiazolyl thioester there are obtained 180 mg (27%) of (3S,4S)-3-[(Z)-2-(2-amino-4-thiazolyl)-2-(methoxyimino)acetamido]-4-[(E)-carbamoylvinyl]-2-oxo-1-azetidinesulphonic acid sodium salt.

Elemental analysis for $C_{12}H_{13}N_6O_7S_2Na$: Calculated: C 32.72, H 2.98, N 19.08%. Found: C 32.68, H 2.91, N 18.93%.

IR (KBr, cm⁻¹): 1769, 1675, 1648, 1613.

¹H-NMR (DMSO, ppm): 3.80 (3H, s, OMe), 4.55 (1H, dd, J=6 and 7.5 Hz, NH—CH—CH), 5.30 (1H, dd, J=6 and 9 Hz, NH—CH—CH), 6.20 (1H, d, J=16 Hz, =CH—CONH₂), 6.70 (1H, dd, J=7.5 and 16 Hz, CH=CH—CONH₂) 6.80 (1H, s, H-thiazole), 7.0–7.5 (4H, br, 2×NH₂), 9.40 (1H, d, J=9 Hz, NH—CH).

The (3S,4S)-3-amino-4-[(E)-2-carbamoylvinyl]-2-oxo-1-azetidinesulphonic acid used as the starting material can be prepared as follows:

59.08 g (0.175 mmol) of (3S,4S)-3-amino-1-(2,4-dimethoxybenzyl)-4-[(R)-2,2-dimethyl-1,3-dioxolan-4-yl]-2-azetidinone in 1 l of dioxan are treated with 46.9 g (0.215 mol) of di-t-butyl dicarbonate in the presence of 16.4 g of potassium carbonate. After stirring at room temperature for 4 hours, the precipitate obtained is filtered off and the filtrate is evaporated under reduced pressure. The residual oily residue is recrystallized from methylene chloride/n-hexane. 64.5 g (84.4%) of t-butyl (3S,4S)-1-(2,4-dimethoxybenzyl)-4-[(R)-2,2-dimethyl-1,3-dioxolan-4-yl]-3-azetidinecarbamate are obtained.

76.8 g (0.176 mol) of t-butyl (3S,4S)-1-(2,4-dimethoxybenzyl)-4-[(R)-2,2-dimethyl-1,3-dioxolan-4-yl]-3-azetidinecarbamate are dissolved in 500 ml of tetrahydrofuran and 350 ml of water and the solution is heated to 60° C. for 24 hours with 13.0 g of p-toluenesulphonic acid. The mixture is cooled, neutralized with 10% aqueous potassium bicarbonate solution and evaporated. The residue is taken up in 300 ml of dioxan and treated with 21.8 g (0.1 mol) of di-t-butyl dicarbonate and 7.63 g of potassium carbonate. The mixture is stirred at room temperature for 24 hours and filtered. The solvent is then removed by evaporation. The crude product is recrystallized from acetonitrile. 61.3 g (88%) of t-butyl (3S, 4S)-1-(2,4-dimethoxybenzyl)-4-[(R)-1,2-dihydroxyethyl]-2-oxo-3-azetidinecarbamate are obtained.

5.0 g (12.6 mmol) of t-butyl (3S,4S)-1-(2,4-dimethoxybenzyl)-4-[(R)-1,2-dihydroxyethyl]-2-oxo-3-azetidinecarbamate are dissolved in 50 ml of methanol and the solution is treated with a solution of 2.95 g (13.8 mmol) of sodium metaperiodate in 30 ml of water. The pH of the solution is held at 6.0 by the addition of aqueous saturated sodium bicarbonate solution. After stirring at room temperature for 30 minutes, the sodium iodate formed is filtered off and the filtrate is evaporated. The residue is taken up in ethyl acetate and washed with aqueous sodium chloride solution, dried over magnesium sulphate and evaporated. The oily residue is crystallized from ether, there being obtained 2.70 g (58.8%) of t-butyl (3S,4S)-1-(2,4-dimethoxybenzyl)-4-formyl-2-oxo-3-azetidinecarbamate.

Elemental analysis for $C_{18}H_{24}N_2O_6$: Calculated: C 59.33, H 6.64, N 7.69%. Found: C 59.08, H 6.91, N 7.38%.

4.0 g (11 mmol) of t-butyl (3S,4S)-1-(2,4-dimethoxybenzyl)-4-formyl-2-oxo-3-azetidinecarbamate are dissolved in 300 ml of methylene chloride and the solution obtained is treated dropwise with a solution of 3.9 g (12 mmol) of carbamoylmethylene-triphenylphosphorane in 100 ml of methylene chloride. After 1 hour, the mixture is filtered and the crystals obtained are washed with methylene chloride. There are obtained 3.6 g (81%) of t-butyl (3R,4S)-1-(2,4-dimethoxybenzyl)-4-[(E)-2-carbamoylvinyl]-2-oxo-3-azetidinecarbamate of melting point 270° C.

IR (KBr, cm$^{-1}$): 1767, 1719, 1684, 1644.

3.6 g (8.9 mmol) of t-butyl (3R,4S)-1-(2,4-dimethoxybenzyl)-4-[(E)-2-carbamoylvinyl]-2-oxo-3-azetidinecarbamate are dissolved in 80 ml of acetonitrile and 150 ml of water and the solution is treated dropwise under reflux with a solution of 4.9 g (17.8 mmol) of potassium peroxydisulphate in 50 ml of water. The pH is held at 6.5 by the addition of saturated aqueous sodium bicarbonate solution. After 4 hours 40 ml of acetonitrile are distilled off. The crude mixture is subsequently partially evaporated and cooled to +5° C. The crystals obtained are filtered off. The filtrate is washed twice with 100 ml of ether each time. The aqueous phase is saturated with sodium chloride and extracted three times with 300 ml of ethyl acetate each time. The combined organic phases are dried over sodium sulphate and evaporated. There is obtained a brown residue which yields 920 mg (41%) of t-butyl (3R,4S)-4-[(E)-2-carbamoylvinyl]-2-oxo-3-azetidinecarbamate after recrystallization from methanol.

IR (KBr, cm$^{-1}$): 1784, 1732, 1689, 1673.

Elemental analysis for $C_{11}H_{17}N_3O_4$: Calculated: C 51.76, H 6.71, N 16.46%. Found: C 51.88, H 6.81, N 16.41%.

1.45 g (5.68 mmol) of t-butyl (3R,4S)-4-[(E)-2-carbamoylvinyl]-2-oxo-3-azetidinecarbamate are dissolved in 80 ml of acetonitrile and the solution is treated with 1.86 g (11.6 mmol) of pyridine-sulphur trioxide complex. The mixture is stirred at 40° C. for 20 hours. The solvent is subsequently removed by evaporation and the residue is taken up in 100 ml of water. The pH is adjusted to 7-8 by the addition of saturated aqueous sodium bicarbonate solution. The volume is reduced to 30 ml by evaporation and the solution obtained is chromatographed on MCI gel using water for the elution. 1.61 g (67.5%) of (3R,4R)-3-(1-t-butoxyformamido)-4-[(E)-2-carbamoylvinyl]-2-oxo-1-azetidinesulphonic acid sodium salt are obtained.

Elemental analysis for $C_{11}H_{16}N_3O_7SNa$: Calculated: C 36.98, H 4.51, N 11.76%. Found: C 37.31, H 4.89, N 11.19%.

IR (KBr, cm$^{-1}$): 1768, 1692, 1645.

1.55 g (4.34 mmol) of (3R,4R)-3-(1-t-butoxyformamido)-4-[(E)-2-carbamoylvinyl]-2-oxo-1-azetidinesulphonic acid sodium salt are dissolved in 5 ml of anisole, the solution is cooled to 0° C. and then treated with 5 ml of trifluoroacetic acid. The suspension obtained is stirred at 0° C. for 1 hour and subsequently at room temperature for 2 hours. The mixture is diluted with 100 ml of ether and 20 ml of n-hexane. The crystals obtained are filtered off and dried. The thus-obtained crude material is dissolved in 10 ml of water and chromatographed on MCI gel using water for the elution. 1.04 g (100%) of (3S,4S)-3-amino-4-[(E)-2-carbamoylvinyl]-2-oxo-1-azetidinesulphonic acid are obtained.

IR (KBr, cm$^{-1}$): 1779, 1683, 1648, 1608.

EXAMPLE 47

278 mg (1 mmol) of rac-cis-3-amino-4-[(Z)-2-(ethoxycarbonyl)-1-methylvinyl]-2-oxo-1-azetidinesulphonic acid are dissolved in 10 ml of water and 10 ml of acetone and the solution is treated with 290 mg (1.1 mmol) of sodium bicarbonate and 386 mg (1.1 mmol) of 2-(2-amino-4-thiazolyl)-2-(Z)-methoxyimino-acetic acid 2-benzthiazolyl thioester. The mixture is stirred at room temperature for 48 hours. The organic solvent is removed under reduced pressure and the resulting crystals are filtered off. The filtrate is chromatographed on MCI gel using water for the elution. 161 mg (43%) of rac-cis-3-[(Z)-2-(2-amino-4-thiazolyl)-2-(methoxyimino)acetamido]-4-[(Z)-2-(ethoxycarbonyl)-1-methylvinyl]-2-oxo-1-azetidinesulphonic acid sodium salt are obtained.

Elemental analysis for $C_{15}H_{18}N_5O_8S_2Na$: Calculated: C 37.27, H 3.75, N 14.49%. Found: C 37.52, H 3.84, N 14.51%.

IR (KBr, cm$^{-1}$): 1771, 1688, 1620, 1533.

$^1$H-NMR (DMSO, ppm): 1.21 (3H, t, J=7 Hz, CH$_3$CH$_2$), 2.03 (3H, d, J=1 Hz, CH$_3$—C=), 3.76 (3H, s, OCH$_3$), 4.08 (2H, q, J=7 Hz, CH$_3$—CH$_2$), 4.54 (1H, dd, J=6 and 1 Hz, NH—CH—CH), 5.28 (1H, dd, J=6 and 9 Hz, NH—CH), 6.05 (1H, t, J=1 Hz, =CH), 6.57 (1H, s, H-thiazole), 7.17 (2H, br, NH$_2$), 9.28 (1H, d, J=9 Hz, NH—CH).

The rac-cis-3-amino-4-[(Z)-2-(ethoxycarbonyl)-1-methyvinyl]-2-oxo-1-azetidinesulphonic acid used as the starting material can be prepared as follows:

6.68 g (0.042 mol) of 2,4-dimethoxybenzylamine in 150 ml of methylene chloride are treated with 5.97 g (0.04 mol) of ethyl 3-formylcrotonate in the presence of magnesium sulphate. After stirring for 30 minutes, the precipitate obtained is filtered off. The imine solution obtained is cooled to 0° C., treated with 6.7 ml of triethylamine and then dropwise with a solution of 10.2 g (0.046 mmol) of phthalimidoacetyl chloride in 50 ml of methylene chloride. The mixture is stirred at 0° C. for 1 hour, then warmed to room temperature and subsequently washed successively with dilute aqueous hydrochloric acid, water and aqueous sodium chloride solution. After drying and evaporation, the crude mixture is recrystallized from methylene chloride/n-hexane. There are obtained 15.6 g (81.6%) of pure ethyl rac-cis-1-(2,4-dimethoxybenzyl)-β-methyl-4-oxo-3-phthalimido-2-azetidineacrylate of melting point 159°-160° C.

IR (KBr, cm$^{-1}$): 1766, 1723, 1656.

37.0 g (77.3 mmol) of ethyl rac-cis-1-(2,4-dimethoxybenzyl)-β-methyl-4-oxo-3-phthalimido-2-azetidineacrylate are dissolved in 500 ml of methylene chloride and the solution is treated with 8.2 ml (0.15 mmol) of N-methylhydrazine at 30° C. for 48 hours. The mixture is filtered and the filtrate is evaporated. The residue is taken up in ethyl acetate and filtered. The filtrate is extracted with 200 ml of aqueous hydrochloric acid and the aqueous phase is separated, neutralized with saturated aqueous sodium bicarbonate solution and extracted twice with 200 ml of methylene chloride each time. After drying and evaporation, the crude colourless product is isolated. There are obtained 25.1 g (93%) of ethyl rac-cis-3-amino-1-(2,4-dimethoxybenzyl)-β-methyl-2-oxo-4-azetidineacrylate of melting point 89°-93° C.

IR (KBr, cm$^{-1}$): 1741, 1708, 1651, 1616.

18.4 g (0.053 mol) of ethyl rac-cis-3-amino-1-(2,4-dimethoxybenzyl)-β-methyl-2-oxo-4-azetidineacrylate are dissolved in 350 ml of dioxan and the solution is treated with 15 ml (0.068 mol) of di-t-butyl dicarbonate in the presence of 5 g of potassium carbonate. The mixture is stirred at room temperature for 12 hours, subsequently filtered and the filtrate is evaporated. The residue is taken up in methylene chloride and washed with water and sodium chloride solution. After drying and evaporation, the crude material is recrystallized from methylene chloride/n-hexane. There are obtained 18.4 g (77.5%) of colourless ethyl rac-cis-3-(1-t-butoxyformamido)-1-(2,4-dimethoxybenzyl)-β-methyl-2-oxo-4-azetidineacrylate of melting point 150°-152° C.

4.0 g (8.9 mmol) of ethyl rac-cis-3-(1-t-butoxyformamido)-1-(2,4-dimethoxybenzyl)-β-methyl-2-oxo-4-azetidineacrylate are dissolved in 300 ml of acetonitrile and the solution is treated at 90°-95° C. with 3.86 g (14.3 mmol) of potassium peroxydisulphate and 2.31 (13.3 mmol) of potassium hydrogen sulphate for 2 hours. The organic solvent is removed by evaporation and the aqueous phase is extracted with chloroform. The combined organic phases are washed with aqueous sodium chloride solution and dried over sodium sulphate. The solution is evaporated and the residue is chromatographed on silica gel using ethyl acetate for the elution. 990 mg (37%) of t-butyl 4-[2-(ethoxycarbonyl)-1-methylvinyl]-2-oxo-3-azetidinecarbamate are obtained.

IR (KBr, cm$^{-1}$): 1783, 1758, 1712, 1703, 1690.

2.25 g (7.5 mmol) of t-butyl-4-[2-(ethoxycarbonyl)-1-methylvinyl]-2-oxo-3-azetidinecarbamate are dissolved in 20 ml of acetonitrile and the solution is treated at room temperature with 3.0 g (18.8 mmol) of sulphur trioxide-pyridine complex. The mixture is stirred at room temperature for 12 hours. The acetonitrile is removed by evaporation and the residue is treated with 3.16 g (36 mmol) of sodium bicarbonate in 60 ml of water. The solution is concentrated to 30 ml by evaporation and cooled to 6° C. 1.92 g (63%) of crystalline rac-cis-3-(1-t-butoxyformamido)-4-[(Z)-2-(ethoxycarbonyl)-1-methylvinyl]-2-oxo-1-azetidinesulphonic acid sodium salt are obtained.

Elemental analysis for C$_{14}$H$_{21}$N$_2$O$_8$SNa: Calculated: C 42.00, H 5.29, N 7.00%. Found: C 42.07, H 5.27, N 7.23%.

IR (KBr, cm$^{-1}$): 1774, 1715, 1692, 1668.

1.755 g (4.38 mmol) of rac-cis-3-(1-t-butoxyformamido)-4-[(Z)-2-(ethoxycarbonyl)-1-methylvinyl]-2-oxo-1-azetidinesulphonic acid sodium salt are dissolved in 7.5 ml of anisole and the solution is treated at −20° C. with 10 ml of trifluoroacetic acid. After stirring at −20° C. for 30 minutes and then at room temperature for a further 3 hours, the solution is diluted with 300 ml of ether/n-hexane (1:1). The crystals obtained are filtered off, dissolved in 10 ml of water and chromatographed on MCI gel. 808 mg (60%) of rac-cis-3-amino-4-[(Z)-2-(ethoxycarbonyl)-1-methylvinyl]-2-oxo-1-azetidinesulphonic acid are obtained.

EXAMPLE 48

717 mg (3 mmol) of (3S,4S)-3-amino-4-carbamoyloxymethyl-2-oxo-1-azetidinesulphonic acid are dispersed in 75 ml of methylene chloride and treated at room temperature while stirring with 0.46 ml (3.3 mmol) of triethylamine and 2.70 g (3.3 mmol) of 2-(tritylamino-4-thiazolyl)-2-(Z)-trityloxyimino-acetic acid 2-benzthiazolyl thioester. The solvent is removed by evaporation and the residue is chromatographed on silica gel using methylene chloride/methanol (92:8) for the elution. 1.58 g (53%) of (3S,4S)-3-[(Z)-2-(2-tritylamino-4-thiazolyl)-2-(trityloxyimino)-acetamido]-4-carbamoyloxymethyl-3-oxo-1-azetidinesulphonic acid are obtained.

1.42 g (1.43 mmol) of (3S, 4S)-3-[(Z)-2-(2-tritylamino-4-thiazolyl)-2-(trityloxyimino)acetamido]-4-carbamoyloxymethyl-3-oxo-1-azetidinesulphonic acid in 15 ml of formic acid are stirred at room temperature for 4 hours with 0.01 ml of water. The solvent is removed by evaporation, the residue is taken up in water and azeotropically distilled with toluene. The residue is recrystallized from water/ethanol (4:1). 296 mg (51%) of (3S,4S)-3-[(Z)-2-(2-amino-4-thiazolyl)-2-(hydroxyimino)acetamido]-4-carbamoyloxymethyl-2-oxo-1-azetidinesulphonic acid are obtained.

The 2-(2-tritylamino-4-thiazolyl)-2-(Z)-trityloxyiminoacetic acid 2-benzthiazolyl thioester used as the starting material can be prepared as follows:

67.2 g of 2-(2-tritylamino-4-thiazolyl)-2-(Z)-trityloxyimino-acetic acid and 40 g of 2,2-dithio-bis-benzthiazole are suspended in 1.6 l of acetonitrile and 16.5 ml of N-methylmopholine and the suspension is treated at 0° C. while stirring with 30 ml of triethyl phosphite in 200 ml of acetonitrile. A small amount of insoluble material is removed by filtration. The solution is concentrated to a small volume and treated with isopropanol. The mixture is again concentrated to a small volume. The thioester which crystallizes out is filtered off and dried. There are obtained 75.0 g of 2-(2-tritylamino-4-thiazolyl)-2-(Z)-trityloxyimino-acetic acid 2-benzthiazolyl thioester of melting point 111°–112° C.

EXAMPLE 49

478 mg of (3S,4S)-3-amino-4-carbamoyloxymethyl-2-oxo-1-azetidinesulphonic acid, 338 mg of 2-(pyrazol-3-yl)-2-(Z)-methoxyimino-acetic acid and 0.892 ml of triethylamine are dissolved in 5 ml of dimethylformamide and the solution is reacted for 1 hour with 613 mg of 2-chloro-1-methylpyridinium iodide. The mixture is evaporated at 25° C. under reduced pressure. The residue is taken up in water and chromatographed over reverse-phase silica gel with water. After lyophilization, there are obtained 645 mg of (3S,4S)-4-carbamoyloxymethyl-3-[[2-(methoxyimino)-2-pyrazol-3-yl]acetamido]-2-oxo-1-azetidinesulphonic acid triethylamine salt.

Elemental analysis for $C_{17}H_{29}N_7O_8S$ (491.52): Calculated: C 41.54, H 5.95, N 19.95, S 6.52%. Found: C 41.47, H 5.57, N 19.11, S 6.71%.

EXAMPLE 50

In the same manner as described in Example 49, from 360 mg of (3S,4S)-trans-3-amino-4-methyl-2-oxo-1-azetidinesulphonic acid and 2-(pyrazol-3-yl)-2-(Z)-methoxyimino-acetic acid there are obtained 423 mg of (3S,4S)-trans-3-[[2-(methoxyimino)-2-(pyrazol-3-yl)]acetamido]-4-methyl-2-oxo-1-azetidinesulphonic acid triethylamine salt.

$^1$H-NMR (DMSO, ppm): 9.25 (d, J=8 Hz, 1H), 7.77 (m, 1H), 6.45 (m, 1H), 4.41 (dd, J=2, 5 Hz and 8 Hz, 1H), 3.85 (s, 3H), 3.64 (dd, J=2.5 Hz and 6 Hz, 1H), 3.69 (q, J=7 Hz, 6H), 1.40 (d, J=6 Hz, 3H), 1.16 (t, J=7 Hz, 9H).

EXAMPLE 51

Manufacture of dry ampoules for intramuscular administration:

A lyophilizate of 1 g of (3S,4S)-3-[(5-amino-3-(1,2,4-thiadiazolyl)]-2-(Z)-(methoxyimino)acetamido]-4-methoxyiminomethyl-2-oxo-1-azetidinesulphonic acid sodium salt is prepared in the usual manner and filled into an ampoule. Prior to the administration the lyophilizate is treated with 2.5 ml of a 2% aqueous lidocaine hydrochloride solution.

What is claimed is:

1. A compound of the formula

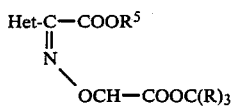

in which Het is selected from the group consisting of pyrazolyl, amino-pyridyl, amino-imidazolyl and amino-oxazolyl groups, R is $C_{1-3}$-alkyl, $R^5$ is allyl, and the group =NOCH$_2$COOC(R)$_3$ is present at least partially in the syn-form.

2. The compound of claim 1, in which the pyrazolyl group is 2-pyrazol-3-yl.

3. The compound of claim 1, in which the amino-pyridyl group is 2-amino-6-pyridyl.

4. The compound of claim 1, in which the amino-imidazolyl group is 2-amino-4-imidazolyl.

5. The compound of claim 1, in which the amino-oxazolyl group is 2-amino-4-oxazolyl.

* * * * *

UNITED STATES PATENT AND TRADEMARK OFFICE
CERTIFICATE OF CORRECTION

PATENT NO. : 4,948,898

DATED : August 14, 1990

INVENTOR(S) : FURLENMEIER ET AL.

It is certified that error appears in the above-identified patent and that said Letters Patent is hereby corrected as shown below:

On the title page, after "[22] Filed: Feb. 28, 1989" and before "Related U.S. Application Data" insert the following:

-- [30] Foreign Application Priority Data

June 3, 1982 [CH] Switzerland ......... 3416/82

June 3, 1982 [CH] Switzerland ......... 3417/82

Apr. 25, 1983 [CH] Switzerland ......... 2201/83 --

Signed and Sealed this

Twenty-ninth Day of December, 1992

Attest:

DOUGLAS B. COMER

Attesting Officer      Acting Commissioner of Patents and Trademarks